United States Patent
Suzuki et al.

(10) Patent No.: US 8,470,555 B2
(45) Date of Patent: Jun. 25, 2013

(54) PROTEIN SUBSTANCE HAVING TRIPLE HELIX STRUCTURE AND MANUFACTURING METHOD THEREFOR

(75) Inventors: Yusuke Suzuki, Osaka (JP); Hiroshi Tahara, Osaka (JP); Keiichi Yamamoto, Osaka (JP); Yuzuru Kitahara, Osaka (JP); Yasuhiko Suzuki, Sapporo (JP)

(73) Assignees: National University Corporation Hokkaido University, Hokkaido (JP); Fuso Pharmaceutical Industries, Ltd., Osaka (JP)

( * ) Notice: Subject to any disclaimer, the term of this patent is extended or adjusted under 35 U.S.C. 154(b) by 71 days.

(21) Appl. No.: 13/141,138

(22) PCT Filed: Dec. 22, 2009

(86) PCT No.: PCT/JP2009/071327
§ 371 (c)(1),
(2), (4) Date: Nov. 10, 2011

(87) PCT Pub. No.: WO2010/074081
PCT Pub. Date: Jul. 1, 2010

(65) Prior Publication Data
US 2012/0059152 A1    Mar. 8, 2012

(30) Foreign Application Priority Data
Dec. 22, 2008  (JP) ................................ 2008-325691

(51) Int. Cl.
C12P 21/06 (2006.01)
C12N 15/00 (2006.01)
C07H 21/02 (2006.01)
C07K 14/00 (2006.01)

(52) U.S. Cl.
USPC ....... 435/69.1; 435/320.1; 536/23.1; 530/350

(58) Field of Classification Search
USPC .............. 530/350; 536/23.1; 435/69.1, 320.1
See application file for complete search history.

(56) References Cited

U.S. PATENT DOCUMENTS

| | | | |
|---|---|---|---|
| 5,405,757 | A | 4/1995 | Prockop et al. |
| 2002/0058339 | A1 | 5/2002 | Takezawa et al. |
| 2007/0154530 | A1 | 7/2007 | Cullen et al. |
| 2009/0203886 | A1 | 8/2009 | Uchiyama et al. |
| 2011/0123993 | A1 | 5/2011 | Suzuki et al. |

FOREIGN PATENT DOCUMENTS

| | | |
|---|---|---|
| CN | 1487839 | 4/2004 |
| EP | 0 856 580 | 8/1998 |
| EP | 1870460 | 12/2007 |
| JP | 7-501939 | 3/1995 |
| JP | 8-23979 | 1/1996 |
| JP | 10-500298 | 1/1998 |
| JP | 2001-316282 | 11/2001 |
| JP | 2002-142753 | 5/2002 |
| JP | 2005-000314 | 1/2005 |
| JP | 2005-14774 | 1/2005 |
| JP | 2007-160092 | 6/2007 |
| JP | 2007-204881 | 8/2007 |
| WO | 95/31540 | 11/1995 |
| WO | 97/07210 | 2/1997 |
| WO | 02/41913 | 5/2002 |
| WO | 2006/106970 | 10/2006 |
| WO | 2007/102230 | 9/2007 |
| WO | 2009/107775 | 9/2009 |

OTHER PUBLICATIONS

Kishore et al. 2006; Surfactant proteins SP-A and SP-D: Structure, function, and receptors. Molecular Immunology. 43: 1293-1315.*
International Search Report for PCT/JP2009/071327 completed Mar. 31, 2010 and mailed Apr. 13, 2010.
Chen et al., "Development and Characterization of a Recombinant Truncated Type VII Collagen "Minigene"" The Journal of Biological Chemistry, 275(32):24429-24435 (Aug. 11, 2000).
Ellingsworth et al., "The Human Immune Response to Reconstituted Bovine Collagen" The Journal of Immunology, 136(3):877-882 (Feb. 1, 1986).
Meade et al., "Immunogenicity of collagenous implants" Biomaterials, 11(3):176-180 (Apr. 1990).
Peacock et al., "The Effect of Hydroxyproline and Reconstituted Collagen Upon Wound Healing in Protein Depleted Rats" Surg. Forum., 10:303-307 (1960).
Shoshan et al., "Acceleration of Wound Healing Induced by Enriched Collagen Solutions" J. Surg. Res., 10 (10):485-491 (Oct. 1970).
Trentham et al., "Effects of Oral Administration of Type II Collagen on Rheumatoid Arthritis" Science, 261 (5129):1727-1730 (Sep. 24, 1993).
Unpublished U.S. Appl. No. 13/140,905, filed Jan. 24, 2012 entitled "Expression Vector for Producing Protein Derived from Foreign Gene in Large Quantity Using Animal Cells, and use thereof" and assigned to National University Corporation and Fuso Pharmaceutical Industries, Ltd.
Genbank Accession No. NM-003019, "*Homo sapiens* surfactant, pulmonary-associated protein D (SFTPD), mRNA," May 24, 1999.
Genbank Accession No. NM-000242, "*Homo spaiens* mannose-binding lectin (protein C) 2, soluble (opsonic defect) (MBL2), mRNA," Apr. 1, 1999.
Genbank Accession No. NM-000088, "*Homo sapiens* collagen, type 1, alpha 1 (COL1A1), mRNA," May 24, 1999.

* cited by examiner

*Primary Examiner* — Karen Cochrane Carlson
(74) *Attorney, Agent, or Firm* — Karl Bozicevic; Bozicevic, Field & Francis LLP

(57) ABSTRACT

As a result of dedicated research, the present inventors have successfully invented a collagen gene construct which can be easily purified and maintains a triple helix structure equivalent to that of naturally-occurring collagen while having a low molecular weight. Specifically, one-step purification by affinity purification is enabled because CR-D (a signal peptide) has a carbohydrate recognition domain. By substituting a portion of a human collagen structural gene of the present invention with the collagen-like structural gene portion of MBL, a low-molecular-weight collagen which maintains a triple helix structure and is thermally stable can be obtained with high purity and in large quantities.

20 Claims, 25 Drawing Sheets

SEQUENCE LISTING

```
<160> NUMBER OF SEQ ID NOS: 15

<210> SEQ ID NO 1
<211> LENGTH: 385
<212> TYPE: PRT
<213> ORGANISM: Homo sapiens

<400> SEQUENCE: 1

Met Leu Leu Phe Leu Leu Ser Ala Leu Val Leu Leu Thr Gln Pro Leu
1               5                   10                  15

Gly Tyr Leu Glu Ala Glu Met Lys Thr Tyr Ser His Arg Thr Met Pro
            20                  25                  30

Ser Ala Cys Thr Leu Val Met Cys Ser Ser Val Glu Ser Gly Lys Ala
        35                  40                  45

Gly Glu Arg Gly Val Pro Gly Pro Pro Gly Ala Val Gly Pro Ala Gly
    50                  55                  60
```

Lys Asp Gly Glu Ala Gly Ala Gln Gly Pro Pro Gly Pro Ala Gly Pro
65                  70                  75                  80

Ala Gly Glu Arg Gly Glu Gln Gly Pro Ala Gly Ser Pro Gly Phe Gln
            85                  90                  95

Gly Leu Pro Gly Pro Ala Gly Pro Pro Gly Glu Ala Gly Lys Pro Gly
            100                 105                 110

Glu Gln Gly Val Pro Gly Asp Leu Gly Ala Pro Gly Pro Ser Gly Ala
            115                 120                 125

Arg Gly Glu Arg Gly Phe Pro Gly Glu Arg Gly Val Gln Gly Pro Pro
            130                 135                 140

Gly Pro Ala Gly Pro Arg Gly Ala Asn Gly Ala Pro Gly Asn Asp Gly
145                 150                 155                 160

Ala Lys Gly Asp Ala Gly Ala Pro Gly Ala Pro Gly Ser Gln Gly Ala
            165                 170                 175

Pro Gly Leu Gln Gly Met Pro Gly Glu Arg Gly Ala Ala Gly Leu Pro
            180                 185                 190

Gly Pro Lys Gly Asp Arg Gly Asp Ala Gly Pro Lys Gly Ala Asp Gly
            195                 200                 205

Ser Pro Gly Lys Asp Gly Val Arg Gly Leu Thr Gly Pro Ile Gly Pro
210                 215                 220

Pro Gly Pro Pro Gly Pro Pro Gly Pro Pro Gly Pro Pro Pro Asp Gly
225                 230                 235                 240

Asp Ser Ser Leu Ala Ala Ser Glu Arg Lys Ala Leu Gln Thr Glu Met
            245                 250                 255

Ala Arg Ile Lys Lys Trp Leu Thr Phe Ser Leu Gly Lys Gln Val Gly
            260                 265                 270

Asn Lys Phe Phe Leu Thr Asn Gly Glu Ile Met Thr Phe Glu Lys Val
            275                 280                 285

Lys Ala Leu Cys Val Lys Phe Gln Ala Ser Val Ala Thr Pro Arg Asn
290                 295                 300

Ala Ala Glu Asn Gly Ala Ile Gln Asn Leu Ile Lys Glu Glu Ala Phe
305                 310                 315                 320

Leu Gly Ile Thr Asp Glu Lys Thr Glu Gly Gln Phe Val Asp Leu Thr
            325                 330                 335

Gly Asn Arg Leu Thr Tyr Thr Asn Trp Asn Glu Gly Glu Pro Asn Asn
            340                 345                 350

Ala Gly Ser Asp Glu Asp Cys Val Leu Leu Leu Lys Asn Gly Gln Trp
            355                 360                 365

Asn Asp Val Pro Cys Ser Thr Ser His Leu Ala Val Cys Glu Phe Pro
            370                 375                 380

Ile
385

<210> SEQ ID NO 2
<211> LENGTH: 6078
<212> TYPE: DNA
<213> ORGANISM: Artificial
<220> FEATURE:
<223> OTHER INFORMATION: An artificially synthesized vector sequence

<400> SEQUENCE: 2
cgatgtacgg gccagatata cgcgttgaca ttgattattg actagttatt aatagtaatc    60
aattacgggg tcattagttc atagcccata tatggagttc cgcgttacat aacttacggt    120
aaatggcccg cctggctgac cgcccaacga cccccgccca ttgacgtcaa taatgacgta    180

```
tgttcccata gtaacgccaa tagggacttt ccattgacgt caatgggtgg agtatttacg      240
gtaaactgcc cacttggcag tacatcaagt gtatcatatg ccaagtacgc ccctattga       300 cgtcaatgac ggtaaatggc ccgcctggca ttatgcccag tacatgacct tatgggactt     360
tcctacttgg cagtacatct acgtattagt catcgctatt accatggtga tgcggttttg    420
gcagtacatc aatgggcgtg gatagcggtt tgactcacgg ggatttccaa gtctccaccc    480
cattgacgtc aatgggagtt tgttttggca ccaaaatcaa cgggactttc caaaatgtcg     540
taacaactcc gccccattga cgcaaatggg cggtaggcgt gtacggtggg aggtctatat    600
aagcagagct ctctggctaa ctagagaacc cactgttaac tggcttatcg aaattgtcga    660
ggagaacttc agggtgagtt tggggaccct tgattgttct ttcttttcg ctattgtaaa     720 attcatgtta tatggagggg gcaaagtttt cagggtgttg tttagaatgg aagatgtcc      780 cttgtatcac catggaccct catgataatt ttgtttcttt cactttctac tctgttgaca    840
accattgtct cctcttattt tcttttcatt ttctgtaact ttttcgttaa actttagctt    900
gcatttgtaa cgaatttta aattcacttt tgtttatttg tcagattgta agtactttct      960
ctaatcactt ttttttcaag gcaatcaggg tatattat tgtacttcag cacagttta       1020 gagaacaatt gttataatta aatgataagg tagaatattt ctgcatataa attctggctg    1080
gcgtggaaat attcttattg gtagaaacaa ctacatcctg gtcatcatcc tgcctttctc    1140
tttatggtta caatgatata cactgtttga gatgaggata aaatactctg agtccaaacc    1200
gggcccctct gctaaccatg ttcatgcctt cttcttttc ctacagctcc tgggcaacgt     1260
gctggcggcc gccttctaga gcctcgactg tgccttctag ttgccagcca tctgttgttt    1320
gcccctcccc cgtgccttcc ttgaccctgg aaggtgccac tcccactgtc ctttcctaat    1380
aaaatgagga aattgcatcg cattgtctga gtaggtgtca ttctattctg ggggtgggg     1440 tggggcagga cagcaagggg gaggattggg aagacaatag caggcatgct ggggaggatc    1500
tccgcggtgt ggaatgtgtg tcagttaggg tgtggaaagt ccccaggctc cccagcaggc    1560
agaagtatgc aaagcatgca tctcaattag tcagcaacca tagtcccgcc cctaactccg    1620
cccatcccgc ccctaactcc gcccagttcc gcccattctc cgccccatgg ctgactaatt    1680
ttttttattt atgcagaggc cgaggccgcc tcggcctctg agctattcca gaagtagtga    1740
ggaggctttt ttggaggcct aggcttttgc aaaaaagctg cagatgattg aacaagatgg    1800
attgcacgca ggttctccgg ccgcttgggt ggagaggcta ttcggctatg actgggcaca    1860
acagacaatc ggctgctctg atgccgccgt gttccggctg tcagcgcagg ggcgcccggt    1920
tctttttgtc aagaccgacc tgtccggtgc cctgaatgaa ctgcaggacg aggcagcgcg    1980
gctatcgtgg ctggccacga cgggcgttcc ttgcgcagct gtgctcgacg ttgtcactga    2040
agcgggaagg gactggctgc tattgggcga agtgccgggg caggatctcc tgtcatctca    2100
ccttgctcct gccgagaaag tatccatcat ggctgatgca atgcggcggc tgcatacgct    2160
tgatccggct acctgcccat tcgaccacca agcgaaacat cgcatcgagc gagcacgtac    2220
tcggatggaa gccggtcttg tcgatcagga tgatctggac gaagagcatc aggggctcgc    2280
gccagccgaa ctgttcgcca ggctcaaggc gcgcatgccc gacggcgagg atctcgtcgt    2340
gacccatggc gatgcctgct tgccgaatat catggtggaa aatggccgct tttctggatt    2400
catcgactgt ggccggctgg gtgtggcgga ccgctatcag gacatagcgt tggctacccg    2460
tgatattgct gaagagcttg gcggcgaatg ggctgaccgc ttcctcgtgc tttacggtat    2520
cgccgctccc gattcgcagc gcatcgcctt ctatcgcctt cttgacgagt tcttctgaga    2580
```

-continued

```
tccgtgacat aattggacaa actacctaca gagatttaaa gctctaaggt aaatataaaa    2640
tttttaagtg tataatgtgt taaactactg attctaattg tttgtgtatt ttagattcca    2700
acctatggaa ctgatgaatg ggagcagtgg tggaatgcct ttaatgagga aaacctgttt    2760
tgctcagaag aaatgccatc tagtgatgat gaggctactc tgactctcca acattctact    2820
cctccaaaaa agaagagaaa ggtagaagac cccaaggact ttccttcaga attgctaagt    2880
tttttgagtc atgctgtgtt tagtaataga actcttgctt gctttgctat ttacaccaca    2940
aaggaaaaag ctgcactgct atacaagaaa attatggaaa atattctgt aacctttata     3000 agtaggcata acagttataa tcataacata ctgttttttc ttactccaca caggcataga    3060
gtgtctgcta ttaataacta tgctcaaaaa ttgtgtacct ttagcttttt aatttgtaaa    3120
ggggttaata aggaatattt gatgtatagt gccttgacta gagatcataa tcagccatac    3180
cacatttgta gaggttttac ttgctttaaa aaacctccca cacctccccc tgaacctgaa    3240
acataaaatg aatgcaattg ttgttgttaa cttgtttatt gcagcttata atggttacaa    3300
ataaagcaat agcatcacaa atttcacaaa taaagcattt ttttcactgc attctagttg    3360
tggtttgtcc aaactcatca atgtatctta tcatgtctgg gcccatcgat gaattcaacg    3420
tacgtagctt ggcactggcc gtcgttttac aacgtcgtga ctgggaaaac cctggcgtta    3480
cccaacttaa tcgccttgca gcacatcccc ctttcgccag ctggcgtaat agcgaagagg    3540
cccgcaccga tcgcccttcc caacagttgc gcagcctgaa tggcgaatgg cgcctgatgc    3600
ggtattttct ccttacgcat ctgtgcggta tttcacaccg catatggtgc actctcagta    3660
caatctgctc tgatgccgca tagttaagcc agccccgaca cccgccaaca cccgctgacg    3720
cgccctgacg ggcttgtctg ctcccggcat ccgcttacag acaagctgtg accgtctccg    3780
ggagctgcat gtgtcagagg ttttcaccgt catcaccgaa acgcgcgagg acgaaagggc    3840
ctcgtgatac gcctattttt ataggttaat gtcatgataa taatggtttc ttagacgtca    3900
ggtggcactt ttcggggaaa tgtgcgcgga acccctattt gtttattttt ctaaatacat    3960
tcaaatatgt atccgctcat gagacaataa ccctgataaa tgcttcaata atattgaaaa    4020
aggaagagta tgagtattca acatttccgt gtcgccctta ttcccttttt tgcggcattt    4080
tgccttcctg tttttgctca cccagaaacg ctggtgaaag taaaagatgc tgaagatcag    4140
ttgggtgcac gagtgggtta catcgaactg gatctcaaca gcggtaagat ccttgagagt    4200
tttcgccccg aagaacgttt tccaatgatg agcacttta aagttctgct atgtggcgcg     4260
gtattatccc gtattgacgc cgggcaagag caactcggtc gccgcataca ctattctcag    4320
aatgacttgg ttgagtactc accagtcaca gaaaagcatc ttacggatgg catgacagta    4380
agagaattat gcagtgctgc cataaccatg agtgataaca ctgcggccaa cttacttctg    4440
acaacgatcg gaggaccgaa ggagctaacc gcttttttgc acaacatggg ggatcatgta    4500
actcgccttg atcgttggga accggagctg aatgaagcca taccaaacga cgagcgtgac    4560
accacgatgc ctgtagcaat ggcaacaacg ttgcgcaaac tattaactgg cgaactactt    4620
actctagctt cccggcaaca attaatagac tggatggagg cggataaagt tgcaggacca    4680
cttctgcgct cggcccttcc ggctggctgg tttattgctg ataaatctgg agccggtgag    4740
cgtgggtctc gcggtatcat tgcagcactg gggccagatg gtaagccctc ccgtatcgta    4800
gttatctaca cgacggggag tcaggcaact atggatgaac gaaatagaca gatcgctgag    4860
ataggtgcct cactgattaa gcattggtaa ctgtcagacc aagtttactc atatatactt    4920
tagattgatt taaaacttca tttttaattt aaaaggatct aggtgaagat cctttttgat    4980
```

```
aatctcatga ccaaaatccc ttaacgtgag ttttcgttcc actgagcgtc agaccccgta    5040
gaaaagatca aaggatcttc ttgagatcct ttttttctgc gcgtaatctg ctgcttgcaa    5100
acaaaaaaac caccgctacc agcggtggtt tgtttgccgg atcaagagct accaactctt    5160
tttccgaagg taactggctt cagcagagcg cagataccaa atactgtcct tctagtgtag    5220
ccgtagttag gccaccactt caagaactct gtagcaccgc ctacatacct cgctctgcta    5280
atcctgttac cagtggctgc tgccagtggc gataagtcgt gtcttaccgg gttggactca    5340
agacgatagt taccggataa ggcgcagcgg tcgggctgaa cggggggttc gtgcacacag    5400
cccagcttgg agcgaacgac ctacaccgaa ctgagatacc tacagcgtga gcattgagaa    5460
agcgccacgc ttcccgaagg gagaaaggcg gacaggtatc cggtaagcgg cagggtcgga    5520
acaggagagc gcacgaggga gcttccaggg ggaaacgcct ggtatcttta tagtcctgtc    5580
gggtttcgcc acctctgact tgagcgtcga ttttgtgat gctcgtcagg ggggcggagc    5640
ctatggaaaa acgccagcaa cgcggccttt ttacggttcc tggccttttg ctggccttt    5700 gctcacatgt tctttcctgc gttatcccct gattctgtgg ataaccgtat taccgccttt    5760
gagtgagctg ataccgctcg ccgcagccga acgaccgagc gcagcgagtc agtgagcgag    5820
gaagcggaag agcgcccaat acgcaaaccg cctctccccg cgcgttggcc gattcattaa    5880
tgcagctggc acgacaggtt tcccgactgg aaagcgggca gtgagcgcaa cgcaattaat    5940
gtgagttagc tcactcatta ggcaccccag gctttacact ttatgcttcc ggctcgtatg    6000
ttgtgtggaa ttgtgagcgg ataacaattt cacacaggaa acagctatga ccatgattac    6060
gaatttcgta cgaagctt                                                 6078

<210> SEQ ID NO 3
<211> LENGTH: 1163
<212> TYPE: DNA
<213> ORGANISM: Homo sapiens

<400> SEQUENCE: 3
caccatgctg ctcttcctcc tctctgcact ggtcctactc acacagcccc tgggctacct      60
ggaagcagaa atgaagacct actcccacag aacaatgccc agtgcttgca ccctggtcat     120
gtgtagctca gtggagtccg aaaggctgg agagcgaggt gttcccggac cccctggcgc     180
tgtcggtcct gctggcaaag atggagaggc tggagctcag ggaccccctg ccctgctgg     240 tcccgctggc gagagaggtg aacaaggccc tgctggctcc cccggattcc agggtctccc     300
tggtcctgct ggtcctccag gtgaagcagg caaacctggt gaacagggtg ttcctggaga     360
ccttggcgcc cctggccct ctggagcaag aggcgagaga ggtttccctg gcgagcgtgg     420
tgtgcaaggt cccctggtc ctgctggacc ccgaggggcc aacggtgctc ccggcaacga     480
tggtgctaag ggtgatgctg gtgcccctgg agctcccggt agccagggcg cccctggcct     540
tcagggaatg cctggtgaac gtggtgcagc tggtcttcca gggcctaagg gtgacagagg     600
tgatgctggt cccaaaggtg ctgatggctc tcctggcaaa gatggcgtcc gtggtctgac     660 cggcccatt ggtccccccg gccctcctgg acctcctggt cccccctggtc ctccccggga     720 tggtgatagt agcctggctg cctcagaaag aaaagctctg caaacagaaa tggcacgtat     780
caaaaagtgg ctcaccttct ctctgggcaa acaagttggg aacaagttct tcctgaccaa     840
tggtgaaata atgacctttg aaaaagtgaa ggccttgtgt gtcaagttcc aggcctctgt     900
ggccaccccc aggaatgctg cagagaatgg agccattcag aatctcatca aggaggaagc     960
cttcctgggc atcactgatg agaagacaga agggcagttt gtggatctga caggaaatag    1020
```

```
actgacctac acaaactgga acgagggtga acccaacaat gctggttctg atgaagattg    1080
tgtattgcta ctgaaaaatg gccagtggaa tgacgtcccc tgctccacct cccatctggc    1140
cgtctgtgag ttccctatct gaa                                            1163

<210> SEQ ID NO 4
<211> LENGTH: 60
<212> TYPE: DNA
<213> ORGANISM: Homo sapiens

<400> SEQUENCE: 4
atgctgctct tcctcctctc tgcactggtc ctactcacac agcccctggg ctacctggaa     60

<210> SEQ ID NO 5
<211> LENGTH: 75
<212> TYPE: DNA
<213> ORGANISM: Homo sapiens

<400> SEQUENCE: 5
gcagaaatga agacctactc ccacagaaca atgcccagtg cttgcaccct ggtcatgtgt     60
agctcagtgg agtcc                                                     75

<210> SEQ ID NO 6
<211> LENGTH: 99
<212> TYPE: DNA
<213> ORGANISM: Homo sapiens

<400> SEQUENCE: 6
ccggatggtg atagtagcct ggctgcctca gaaagaaaag ctctgcaaac agaaatggca     60
cgtatcaaaa agtggctcac cttctctctg ggcaaacaa                           99

<210> SEQ ID NO 7
<211> LENGTH: 348
<212> TYPE: DNA
<213> ORGANISM: Homo sapiens

<400> SEQUENCE: 7
gttgggaaca agttcttcct gaccaatggt gaaataatga cctttgaaaa agtgaaggcc     60
ttgtgtgtca agttccaggc ctctgtggcc accccagga atgctgcaga gaatggagcc    120
attcagaatc tcatcaagga ggaagccttc ctgggcatca ctgatgagaa gacagaaggg    180
cagtttgtgg atctgacagg aaatagactg acctacacaa actggaacga gggtgaaccc    240
aacaatgctg gttctgatga agattgtgta ttgctactga aaaatggcca gtggaatgac    300
gtcccctgct ccacctccca tctggccgtc tgtgagttcc ctatctga                348

<210> SEQ ID NO 8
<211> LENGTH: 576
<212> TYPE: DNA
<213> ORGANISM: Homo sapiens

<400> SEQUENCE: 8
ggaaaggctg agagcgagg tgttcccgga ccccctggcg ctgtcggtcc tgctggcaaa      60
gatggagagg ctggagctca gggacccccct ggccctgctg gtcccgctgg cgagagaggt   120
gaacaaggcc ctgctggctc ccccggattc cagggtctcc ctggtcctgc tggtcctcca   180
ggtgaagcag gcaaacctgg tgaacagggt gttcctggag accttggcgc ccctggcccc   240
tctggagcaa gaggcgagag aggtttccct ggcgagcgtg gtgtgcaagg tccccctggt   300
cctgctggac cccgaggggc caacggtgct cccggcaacg atggtgctaa gggtgatgct   360
```

```
ggtgcccctg gagctcccgg tagccagggc gcccctggcc ttcagggaat gcctggtgaa      420
cgtggtgcag ctggtcttcc agggcctaag ggtgacagag gtgatgctgg tcccaaaggt      480
gctgatggct ctcctggcaa agatggcgtc cgtggtctga ccggccccat tggtcccccc      540
ggccctcctg gacctcctgg tcccctggt cctccc                                 576

<210> SEQ ID NO 9
<211> LENGTH: 5633
<212> TYPE: DNA
<213> ORGANISM: Artificial
<220> FEATURE:
<223> OTHER INFORMATION: An artificially synthesized vector sequence

<400> SEQUENCE: 9
cgcgttacat aacttacggt aaatggcccg cctggctgac cgcccaacga ccccgccca       60 ttgacgtcaa taatgacgta tgttcccata gtaacgccaa tagggacttt ccattgacgt     120
caatgggtgg agtatttacg gtaaactgcc cacttggcag tacatcaagt gtatcatatg     180
ccaagtccgc ccctattga cgtcaatgac ggtaaatggc ccgcctggca ttatgcccag     240
tacatgacct tacgggactt tcctacttgg cagtacatct acgtattagt catcgctatt     300
accatggtga tgcggttttg gcagtacacc aatgggcgtg gatagcggtt tgactcacgg     360
ggatttccaa gtctccaccc cattgacgtc aatgggagtt tgttttggca ccaaaatcaa     420
cgggactttc caaaatgtcg taataacccc gccccgttga cgcaaatggg cggtaggcgt     480
gtacggtggg aggtctatat aagcagagct cgtttagtga accgtcagat cctcactctc     540
ttccgcatcg ctgtctgcga gggccagctg ttgggctcgc ggttgaggac aaactcttcg     600
cggtctttcc agtactcttg gatcggaaac ccgtcggcct ccgaacggta ctccgccacc     660
gagggacctg agcgagtccg catcgaccgg atcggaaaac ctctcgagaa aggcgtctaa     720
ccagtcacag tcgcaaggta ggctgagcac cgtggcgggc ggcagcgggt ggcggtcggg     780 gttgttctg gcggaggtgc tgctgatgat gtaattaaag taggcggtct tgagacggcg     840
gatggtcgag gtgaggtgtg gcaggcttga gatccagctg ttggggtgag tactccctct     900
caaaagcggg catgacttct gcgctaagat tgtcagtttc caaaaacgag gaggatttga     960
tattcacctg gcccgatctg gccatacact tgagtgacaa tgacatccac tttgcctttc    1020
tctccacagg tgtccactcc caggtccaag cggccgcctt ctagagcctc gactgtgcct    1080
tctagttgcc agccatctgt tgtttgcccc tccccgtgc cttccttgac cctggaaggt    1140
gccactccca ctgtcctttc ctaataaaat gaggaaattg catcgcattg tctgagtagg    1200
tgtcattcta ttctgggggg tggggtgggg caggacagca agggggagga ttgggaagac    1260
aatagcaggc atgctgggga ggatctccgc ggtgtggaat gtgtgtcagt tagggtgtgg    1320
aaagtcccca ggctcccag caggcagaag tatgcaaagc atgcatctca attagtcagc     1380
aaccatagtc ccgcccctaa ctccgcccat cccgcccta actccgccca gttccgccca    1440
ttctccgccc catggctgac taattttttt tatttatgca gaggccgagg ccgcctcggc    1500
ctctgagcta ttccagaagt agtgaggagg ctttttttgga ggcctaggct tttgcaaaaa    1560
agctgcagat ggtacgacca ttaaattgta ttgtagcagt atcacaaaat atgggtattg    1620
gtaaaaatgg tgatttacca tggccaccat tacgaaatga atttaaatat tttcaacgaa    1680
tgactactac ttcatcagta gaaggtaaac aaaatttagt aattatgggt cgaaaaactt    1740
ggttttcaat tcctgagaag aatcgacctt taaaggacag aattaatata gttctcagta    1800
gagaactcaa agaaccacca cgaggagctc atttttcttgc caaaagtttg gatgatgcct    1860
```

```
taagacttat tgaacaaccg gaattggcaa gtaaagtaga catggtttgg atagtcggag    1920
gcagttctgt ttaccaggaa gccatgaatc aaccaggcca cctcagactc tttgtgacaa    1980
ggatcatgca ggaatttgaa agtgacacgt ttttcccaga aattgatttg gggaaatata    2040
aacttctccc agaatacccca ggcgtcctct ctgaggtcca ggaggaaaaa ggcatcaagt    2100
ataagtttga agtctacgag aagaaagact aaagatccgt gacataattg gacaaactac    2160
ctacagagat ttaaagctct aaggtaaata taaaatttt aagtgtataa tgtgttaaac     2220
tactgattct aattgtttgt gtattttaga ttccaaccta tggaactgat gaatgggagc    2280
agtggtggaa tgcctttaat gaggaaaacc tgttttgctc agaagaaatg ccatctagtg    2340
atgatgaggc tactgctgac tctcaacatt ctactcctcc aaaaaagaag agaaaggtag    2400
aagaccccaa ggactttcct tcagaattgc taagtttttt gagtcatgct gtgtttagta    2460
atagaactct tgcttgcttt gctatttaca ccacaaagga aaagctgca ctgctataca     2520 agaaaattat ggaaaaatat tctgtaacct ttataagtag gcataacagt tataatcata    2580
acatactgtt ttttcttact ccacacaggc atagagtgtc tgctattaat aactatgctc    2640
aaaaattgtg tacctttagc ttttaatt gtaaaggggt taataaggaa tatttgatgt      2700
atagtgcctt gactagagat cataatcagc cataccacat ttgtagaggt tttacttgct    2760
ttaaaaaacc tcccacacct cccctgaac ctgaaacata aaatgaatgc aattgttgtt     2820
gttaacttgt ttattgcagc ttataatggt tacaaataaa gcaatagcat cacaaatttc    2880
acaaataaag cattttttc actgcattct agttgtggtt tgtccaaact catcaatgta     2940
tcttatcatg tctgggccca tcgatgaatt caacgtacgt agcttggcac tggccgtcgt    3000
tttacaacgt cgtgactggg aaaaccctgg cgttacccaa cttaatcgcc ttgcagcaca    3060
tccccctttc gccagctggc gtaatagcga agaggcccgc accgatcgcc cttcccaaca    3120
gttgcgcagc ctgaatggcg aatggcgcct gatgcggtat tttctcctta cgcatctgtg    3180
cggtatttca caccgcatat ggtgcactct cagtacaatc tgctctgatg ccgcatagtt    3240
aagccagccc cgacacccgc caacacccgc tgacgcgccc tgacgggctt gtctgctccc    3300
ggcatccgct tacagacaag ctgtgaccgt ctccgggagc tgcatgtgtc agaggttttc    3360
accgtcatca ccgaaacgcg cgaggacgaa agggcctcgt gatacgccta ttttttatagg   3420 ttaatgtcat gataataatg gtttcttaga cgtcaggtgg cacttttcgg ggaaatgtgc    3480
gcggaacccc tatttgttta ttttctaaa tacattcaaa tatgtatccg ctcatgagac     3540
aataaccctg ataaatgctt caataatatt gaaaaaggaa gagtatgagt attcaacatt    3600
tccgtgtcgc ccttattccc ttttttgcgg cattttgcct tcctgttttt gctcacccag    3660
aaacgctggt gaaagtaaaa gatgctgaag atcagttggg tgcacgagtg ggttacatcg    3720
aactggatct caacagcggt aagatccttg agagttttcg ccccgaagaa cgttttccaa    3780
tgatgagcac ttttaaagtt ctgctatgtg gcgcggtatt atcccgtatt gacgccgggc    3840
aagagcaact cggtcgccgc atacactatt ctcagaatga cttggttgag tactcaccag    3900
tcacagaaaa gcatcttacg gatggcatga cagtaagaga attatgcagt gctgccataa    3960
ccatgagtga taacactgcg gccaacttac ttctgacaac gatcggagga ccgaaggagc    4020
taaccgcttt tttgcacaac atgggggatc atgtaactcg ccttgatcgt tgggaaccgg    4080
agctgaatga agccatacca aacgacgagc gtgacaccac gatgcctgta gcaatggcaa    4140
caacgttgcg caaactatta actggcgaac tacttactct agcttcccgg caacaattaa    4200
tagactggat ggaggcggat aaagttgcag gaccacttct gcgctcggcc cttccggctg    4260
```

-continued

```
gctggtttat tgctgataaa tctggagccg gtgagcgtgg gtctcgcggt atcattgcag    4320
cactggggcc agatggtaag ccctcccgta tcgtagttat ctacacgacg gggagtcagg    4380
caactatgga tgaacgaaat agacagatcg ctgagatagg tgcctcactg attaagcatt    4440
ggtaactgtc agaccaagtt tactcatata tactttagat tgatttaaaa cttcattttt    4500
aatttaaaag gatctaggtg aagatccttt ttgataatct catgaccaaa atcccttaac    4560
gtgagttttc gttccactga gcgtcagacc ccgtagaaaa gatcaaagga tcttcttgag    4620
atcctttttt tctgcgcgta atctgctgct tgcaaacaaa aaaaccaccg ctaccagcgg    4680
tggtttgttt gccggatcaa gagctaccaa ctcttttccc gaaggtaact ggcttcagca    4740
gagcgcagat accaaatact gtccttctag tgtagccgta gttaggccac cacttcaaga    4800
actctgtagc accgcctaca tacctcgctc tgctaatcct gttaccagtg gctgctgcca    4860
gtggcgataa gtcgtgtctt accgggttgg actcaagacg atagttaccg gataaggcgc    4920
agcggtcggg ctgaacgggg ggttcgtgca cacagcccag cttggagcga acgacctaca    4980
ccgaactgag atacctacag cgtgagcatt gagaaagcgc cacgcttccc gaagggagaa    5040
aggcggacag gtatccggta agcggcaggg tcggaacagg agagcgcacg agggagcttc    5100 caggggggaaa cgcctggtat ctttatagtc ctgtcgggtt tcgccacctc tgacttgagc    5160
gtcgattttt gtgatgctcg tcaggggggc ggagcctatg gaaaaacgcc agcaacgcgg    5220
cctttttacg gttcctggcc ttttgctggc cttttgctca catgttcttt cctgcgttat    5280
cccctgattc tgtggataac cgtattaccg cctttgagtg agctgatacc gctcgccgca    5340
gccgaacgac cgagcgcagc gagtcagtga gcgaggaagc ggaagagcgc ccaatacgca    5400
aaccgcctct ccccgcgcgt tggccgattc attaatgcag ctggcacgac aggtttcccg    5460
actggaaagc gggcagtgag cgcaacgcaa ttaatgtgag ttagctcact cattaggcac    5520
cccaggcttt acactttatg cttccggctc gtatgttgtg tggaattgtg agcggataac    5580
aatttcacac aggaaacagc tatgaccatg attacgaatt tcgtacgaag ctt           5633
```

<210> SEQ ID NO 10
<211> LENGTH: 4395
<212> TYPE: DNA
<213> ORGANISM: Homo sapiens

<400> SEQUENCE: 10

```
atgttcagct ttgtggacct ccggctcctg ctcctcttag cggccaccgc cctcctgacg     60
cacggccaag aggaaggcca agtcgagggc aagacgaaga catcccacc aatcacctgc    120 gtacagaacg gcctcaggta ccatgaccga gacgtgtgga acccgagcc ctgccggatc    180 tgcgtctgcg acaacggcaa ggtgttgtgc gatgacgtga tctgtgacga gaccaagaac    240
tgccccggcg ccgaagtccc cgagggcgag tgctgtcccg tctgccccga cggctcagag    300
tcacccaccg accaagaaac caccggcgtc gagggaccca aggagacac tggccccga    360 ggcccaaggg gacccgcagg cccccctggc cgagatggca tccctggaca gcctggactt    420
cccggacccc ccgacccccc cggacctccc ggaccccctg gctcggagg aaactttgct    480 ccccagctgt cttatggcta tgatgagaaa tcaaccggag gaatttccgt gcctggcccc    540
atgggtccct ccggtcctcg tggtctccct ggccccctg gtgcacctgg tccccaaggc    600
ttccaaggtc cccctggtga gcctggcgag cctggagctt caggtcccat gggtcccga    660 ggtcccccag gtcccctgg aaagaatgga gatgatgggg aagctggaaa acctggtcgt    720
cctggtgagc gtgggcctcc tgggcctcag ggtgcccgag gattgccgg aacagctggc    780
```

```
ctccctggaa tgaagggaca cagaggtttc agtggtttgg atggtgccaa gggagatgct      840
ggtcctgctg gtcctaaggg tgagcctggc agccctggtg aaaatggagc tcctggtcag      900
atgggccccc gtggcctgcc tggtgagaga ggtcgccctg gagccctgg ccctgctggt       960
gctcgtggaa atgatggtgc tactggtgct gccgggcccc ctggtcccac cggcccgct      1020
ggtcctcctg gcttccctgg tgctgttggt gctaagggtg aagctggtcc ccaagggccc     1080
cgaggctctg aaggtcccca gggtgtgcgt ggtgagcctg gcccccctgg ccctgctggt     1140
gctgctggcc ctgctggaaa ccctggtgct gatggacagc tggtgctaa aggtgccaat      1200
ggtgctcctg gtattgctgg tgctcctggc ttccctggtg cccgaggccc ctctggaccc     1260
cagggccccg gcggccctcc tggtcccaag ggtaacagcg agaacctgg tgctcctggc      1320
agcaaaggag acactggtgc taagggagag cctggcccc ttggtgttca aggacccct      1380
ggccctgctg agaggaagg aaagcgagga gctcgaggtg aacccggacc cactggcctg      1440
cccggacccc ctggcgagcg tgtggacct ggtagccgtg gtttccctgg cgcagatggt      1500
gttgctggtc ccaagggtcc cgctggtgaa cgtggttctc ctggccctgc tggccccaaa     1560
ggatctcctg gtgaagctgg tcgtccggt gaagctggtc tgcctggtgc aagggtctg      1620
actggaagcc ctggcagccc tggtcctgat ggcaaaactg gccccctgg tcccgccggt     1680
caagatggtc gccccggacc cccaggccca cctggtgccc gtggtcaggc tggtgtgatg     1740
ggattccctg gacctaaagg tgctgctgga gagcccggca aggctggaga gcgaggtgtt     1800
cccgacccc ctggcgctgt cggtcctgct ggcaaagatg gagaggctgg agctcaggga     1860
cccctggcc ctgctggtcc cgctggcgag agaggtgaac aaggccctgc tggctccccc     1920
ggattccagg gtctccctgg tcctgctggt ccctcaggtg aagcaggcaa acctggtgaa     1980
cagggtgttc ctggagacct ggcgcccct ggccctctg agcaagagg cgagagaggt       2040
ttccctggcg agcgtggtgt gcaaggtccc cctggtcctg ctggtccccg agggccaac      2100
ggtgctcccg gcaacgatgg tgctaagggt gatgctggtg cccctggagc tcccggtagc     2160
cagggcgccc ctggccttca gggaatgcct ggtgaacgtg gtgcagctgg tcttccaggg     2220
cctaagggtg acagaggtga tgctggtccc aaaggtgctg atggctctcc tggcaaagat     2280
ggcgtccgtg gtctgaccgg ccccattggt cctcctggcc ctgctggtgc cctggtgac     2340
aagggtgaaa gtggtcccag cggccctgct ggtcccactg gagctcgtgg tgcccccgga     2400
gaccgtggtg agcctggtcc ccccggccct gctggctttg ctggcccccc tggtgctgac     2460
ggccaacctg gtgctaaagg cgaacctggt gatgctggtg ctaaaggcga tgctggtccc     2520
cctggccctg ccggacccgc tggacccct ggccccattg gtaatgttgg tgctcctgga     2580
gccaaaggtc tcgcggcag cgctggtccc ctggtgcta ctggtttccc tggtgctgct     2640
ggccgagtcg gtcctcctgg cccctctgga atgctggac ccctggccc tctggtcct      2700
gctggcaaag aaggcggcaa aggtcccgt ggtgagactg gccctgctgg acgtcctggt     2760
gaagttggtc cccctggtcc ccctggccct gctggcgaga aggatccccc tggtgctgat     2820
ggtcctgctg gtgctcctgg tactcccggg cctcaaggta ttgctggaca gcgtggtgtg     2880
gtcggcctgc ctggtcagag aggagagaga ggcttccctg gtcttcctgg cccctctggt     2940
gaacctggca aacaaggtcc ctcggagca agtggtgaac gtggtccccc tggtcccatg     3000
ggcccccctg gattggctgg acccccctggt gaatctggac gtgagggggc tcctggtgcc     3060
gaaggttccc ctgacgaga cggttctcct ggcgccaagg gtgaccgtgg tgagaccggc     3120
cccgctggac ccctggtgc tcctggtgct cctggtgccc ctggccccgt tggccctgct     3180
```

| | |
|---|---:|
| ggcaagagtg gtgatcgtgg tgagactggt cctgctggtc ccgccggtcc tgtcggccct | 3240 |
| gttggcgccc gtggccccgc cggaccccaa ggccccgtg gtgacaaggg tgagacaggc | 3300 |
| gaacagggcg acagaggcat aaagggtcac cgtggcttct ctggcctcca gggtccccct | 3360 |
| ggccctcctg gctctcctgg tgaacaaggt ccctctggag cctctggtcc tgctggtccc | 3420 |
| cgaggtcccc ctggctctgc tggtgctcct ggcaaagatg gactcaacgg tctccctggc | 3480 |
| cccattgggc ccctggtcc tcgcggtcgc actggtgatg ctggtcctgt tggtcccccc | 3540 |
| ggccctcctg gacctcctgg tccccctggt cctcccagcg ctggtttcga cttcagcttc | 3600 |
| ctgccccagc cacctcaaga gaaggctcac gatggtggcc gctactaccg ggctgatgat | 3660 |
| gccaatgtgg ttcgtgaccg tgacctcgag gtggacacca ccctcaagag cctgagccag | 3720 |
| cagatcgaga acatccggag cccagagggc agccgcaaga accccgcccg cacctgccgt | 3780 |
| gacctcaaga tgtgccactc tgactggaag agtggagagt actggattga ccccaaccaa | 3840 |
| ggctgcaacc tggatgccat caaagtcttc tgcaacatgg agactggtga cctgcgtg | 3900 |
| taccccactc agcccagtgt ggcccagaag aactggtaca tcagcaagaa ccccaaggac | 3960 |
| aagaggcatg tctggttcgg cgagagcatg accgatggat tccagttcga gtatggcggc | 4020 |
| cagggctccg accctgccga tgtggccatc cagctgacct tcctgcgcct gatgtccacc | 4080 |
| gaggcctccc agaacatcac ctaccactgc aagaacagcg tggcctacat ggaccagcag | 4140 |
| actggcaacc tcaagaaggc cctgctcctc cagggctcca acgagatcga gatccgcgcc | 4200 |
| gagggcaaca ccgcgttcac ctacagcgtc actgtcgatg gctgcacgag tcacaccgga | 4260 |
| gcctggggca agacagtgat tgaatacaaa accaccaaga cctcccgcct gcccatcatc | 4320 |
| gatgtggccc ccttggacgt tggtgccca gaccaggaat tcggcttcga cgttggccct | 4380 |
| gtctgcttcc tgtaa | 4395 |

<210> SEQ ID NO 11
<211> LENGTH: 4101
<212> TYPE: DNA
<213> ORGANISM: Homo sapiens

<400> SEQUENCE: 11

| | |
|---|---:|
| atgctcagct ttgtggatac gcggactttg ttgctgcttg cagtaacctt atgcctagca | 60 |
| acatgccaat ctttacaaga ggaaactgta agaaagggcc cagccggaga tagaggacca | 120 |
| cgtggagaaa ggggtccacc aggccccca ggcagagatg gtgaagatgg tcccacaggc | 180 |
| cctcctggtc cacctggtcc tcctggcccc ctggtctcg gtgggaactt tgctgctcag | 240 |
| tatgatggaa aaggagttgg acttggccct ggaccaatgg gcttaatggg acctagaggc | 300 |
| ccacctggtg cagctggagc cccaggccct caaggtttcc aaggacctgc tggtgagcct | 360 |
| ggtgaacctg gtcaaactgg tcctgcaggt gctcgtggtc cagctggccc tcctggcaag | 420 |
| gctggtgaag atggtcaccc tggaaaaccc ggacgacctg gtgagagagg agttgttgga | 480 |
| ccacagggtg ctcgtggttt ccctggaact cctggacttc ctggcttcaa aggcattagg | 540 |
| ggacacaatg gtctggatgg actgaaggga cagcccggtg ctcctggtgt aagggtgaa | 600 |
| cctggtgccc ctggtgaaaa tggaactcca ggtcaaacag gagcccgtgg gcttcctggc | 660 |
| gagagaggac gtgttggtgc ccctggccca gctggtgccc gtggcagtga tggaagtgtg | 720 |
| ggtcccgtgg gtcctgctgg tcccattggg tctgctggcc ctccaggctt cccaggtgcc | 780 |
| cctggccca agggtgaaat tggagctgtt ggtaacgctg gtcctgctgg tcccgccggt | 840 |
| ccccgtggtg aagtgggtct tccaggcctc tccggccccg ttggacctcc tggtaatcct | 900 |

```
ggagcaaacg gccttactgg tgccaagggt gctgctggcc ttcccggcgt tgctggggct    960
cccggcctcc ctggacccccg cggtattcct ggccctgttg gtgctgccgg tgctactggt   1020
gccagaggac ttgttggtga gcctggtcca gctggctcca aaggagagag cggtaacaag   1080
ggtgagcccg gctctgctgg gccccaaggt cctcctggtc ccagtggtga agaaggaaag   1140
agaggcccta atggggaagc tggatctgcc ggccctccag gacctcctgg gctgagaggt   1200
agtcctggtt ctcgtggcct tcctggagct gatggcagag ctggcgtcat gggccctcct   1260
ggtagtcgtg gtgcaagtgg ccctgctgga gtccgaggac ctaatggaga tgctggtcgc   1320
cctggggagc ctggtctcat gggacccaga ggtcttcctg gttcccctgg aaatatcggc   1380
cccgctggaa agaaggtcc tgtcggcctc cctggcatcg acggcaggcc tggcccaatt   1440
ggccccgctg gagcaagagg agagcctggc aacattggat ccctggacc caaaggcccc   1500
actggtgatc ctggcaaaaa cggtgataaa ggtcatgctg gtcttgctgg tgctcgggt   1560
gctccaggtc ctgatggaaa caatggtgct cagggacctc ctggaccaca gggtgttcaa   1620
ggtggaaaag gtgaacaggg tcccgctggt cctccaggct ccagggtct gcctggcccc   1680
tcaggtcccg ctggtgaagt tggcaaacca ggagaaaggg gcctccatgg tgagtttggt   1740
ctccctggtc ctgctggtcc aagaggggaa cgcggtcccc caggtgagag tggtgctgcc   1800
ggtcctactg gtcctattgg aagccgaggt ccttctggac ccccagggcc tgatggaaac   1860
aagggtgaac ctggtgtggt tggtgctgtg ggcactgctg gtccatctgg tcctagtgga   1920
ctcccaggag agaggggtgc tgctggcata cctggaggca agggagaaaa gggtgaacct   1980
ggtctcagag gtgaaattgg taaccctggc agagatggtg ctcgtggtgc ccctggtgct   2040
gtaggtgccc ctggtcctgc tggagccaca ggtgaccggg gcgaagctgg ggctgctggt   2100
cctgctggtc ctgctggtcc tcggggaagc cctggtgaac gtggtgaggt cggtcctgct   2160
ggccccaatg gatttgctgg tcctgctggt gctgctggtc aacctggtgc taaaggagaa   2220
agaggagcca agggcctaa gggtgaaaac ggtgttgttg gtcccacagg ccccgttgga   2280
gctgctggcc cagctggtcc aaatggtccc cccggtcctg ctggaagtcg tggtgatgga   2340
ggccccctg gtatgactgg tttccctggt ctgctggac ggaccggtcc cccaggaccc   2400
tctggtattt ctggccctcc tggtcccccct ggtcctgctg ggaaagaagg gcttcgtggt   2460
cctcgtggtg accaaggtcc agttggccga actgagaag taggtgcagt tggtccccct   2520
ggcttcgctg gtgagaaggg tccctctgga gaggctggta ctgctggacc tcctggcact   2580
ccaggtcctc agggtcttct tggtgctcct ggtattctgg gtctccctgg ctcgagaggt   2640
gaacgtggtc taccaggtgt tgctggtgct gtgggtgaac ctggtcctct tggcattgcc   2700
ggccctcctg ggcccgtgg tcctcctggt gctgtggtta gtcctggagt caacggtgct   2760
cctggtgaag ctggtcgtga tggcaaccct gggaacgatg gtccccccagg tcgcgatggt   2820
caacccggac acaagggaga gcgcggttac cctggcaata ttggtcccgt tggtgctgca   2880
ggtgcacctg gtcctcatgg ccccgtgggt cctgctggca acatggaaa ccgtggtgaa   2940
actggtcccct ctggtcctgt tggtcctgct ggtgctgttg gcccaagagg tcctagtggc   3000
ccacaaggca ttcgtggcga taagggagag cccggtgaaa aggggcccag aggtcttcct   3060
ggcttaaagg gacacaatgg attgcaaggt ctgcctggta tcgctggtca ccatggtgat   3120
caaggtgctc ctggctccgt gggtcctgct ggtcctaggg gccctgctgg tccttctggc   3180
cctgctggaa aagatggtcg cactggacat cctggtacag ttggacctgc tggcattcga   3240
ggccctcagg gccaccaagg ccctgctggc cccctggtc cccctggccc tctggacct   3300
```

-continued

```
ccaggtgtaa gcggtggtgg ttatgacttt ggttacgatg gagacttcta cagggctgac    3360
cagcctcgct cagcaccttc tctcagaccc aaggactatg aagttgatgc tactctgaag    3420
tctctcaaca accagattga gacccttctt actcctgaag gctctagaaa gaacccagct    3480
cgcacatgcc gtgacttgag actcagccac ccagagtgga gcagtggtta ctactggatt    3540
gaccctaacc aaggatgcac tatggatgct atcaaagtat actgtgattt ctctactggc    3600
gaaacctgta tccgggccca acctgaaaac atcccagcca gaactggta  taggagctcc    3660
aaggacaaga aacacgtctg gctaggagaa actatcaatg ctggcagcca gtttgaatat    3720
aatgtagaag gagtgacttc caaggaaatg gctacccaac ttgccttcat gcgcctgctg    3780
gccaactatg cctctcagaa catcacctac cactgcaaga acagcattgc atacatggat    3840
gaggagactg caacctgaa  aaaggctgtc attctacagg gctctaatga tgttgaactt    3900
gttgctgagg caacagcag  gttcacttac actgttcttg tagatggctg ctctaaaaag    3960
acaaatgaat ggggaaagac aatcattgaa tacaaaacaa ataagccatc acgcctgccc    4020
ttccttgata ttgcaccttt ggacatcggt ggtgctgacc aggaattctt tgtggacatt    4080
ggcccagtct gtttcaaata a                                              4101
```

<210> SEQ ID NO 12
<211> LENGTH: 4257
<212> TYPE: DNA
<213> ORGANISM: Homo sapiens

<400> SEQUENCE: 12

```
atgattcgcc tcggtgctcc ccagtcgctg gtgctgctga cgctgctcgt cgccgctgtc      60
cttcggtgtc agggccagga tgtccggcaa ccaggaccaa aggacagaa  aggagaacct     120
ggagacatca aggatattgt aggacccaaa ggacctcctg gcctcaggg  acctgcaggg     180
gaacaaggac ccagagggga tcgtggtgac aaaggtgaaa aggtgcccc  tggacctcgt     240
ggcagagatg gagaacctgg gacccctgga atcctggcc  ccctggtcc  tcccggcccc     300
cctggtcccc ctggtcttgg tggaaacttt gctgcccaga tggctggagg atttgatgaa     360
aaggctggtg gcgcccagtt gggagtaatg caaggaccaa tgggcccat  gggacctcga     420
ggacctccag gccctgcagg tgctcctggg cctcaaggat ttcaaggcaa tcctggtgaa     480
cctggtgaac ctggtgtctc tggtcccatg ggtccccgtg gtcctcctgg tccccctgga     540
aagcctggtg atgatggtga agctggaaaa cctggaaaag ctggtgaaag gggtccgcct     600
ggtcctcagg gtgctcgtgg tttcccagga accccaggcc ttcctggtgt caaaggtcac     660
agaggttatc caggcctgga cggtgctaag ggagaggcgg gtgctcctgg tgtgaagggt     720
gagagtggtt cccgggtga  gaacggatct ccgggcccaa tgggtcctcg tggcctgcct     780
ggtgaaagag gacggactgg ccctgctggc gctgcgggtg cccgaggcaa cgatggtcag     840
ccaggccccg cagggcctcc gggtcctgtc ggtcctgctg gtggtcctgg cttccctggt     900
gctcctggag ccaagggtga agccggcccc actggtgccc gtggtcctga aggtgctcaa     960
ggtcctcgcg gtgaacctgg tactcctggg tcccctgggc tgctggtgc  ctccggtaac    1020
cctggaacag atggaattcc tggagccaaa ggatctgctg gtgctcctgg cattgctggt    1080
gctcctggct ccctgggcc  acggggccct cctggccctc aggtgcaac  tggtcctctg    1140
ggcccgaaag gtcagacggg tgaacctggt attgctggct cagggtga  caaggccccc    1200
agggagaac ctggccctgc tggccccag  ggagccctg  acccgctgg  tgaagaaggc    1260
aagagaggtg cccgtggaga gcctggtggc gttgggccca tcggtcccc  tggagaaaga    1320
```

```
ggtgctcccg gcaaccgcgg tttcccaggt caagatggtc tggcaggtcc caagggagcc      1380
cctggagagc gagggcccag tggtcttgct ggccccaagg gagccaacgg tgaccctggc      1440
cgtcctggag aacctggcct tcctggagcc cggggtctca ctggccgccc tggtgatgct      1500
ggtcctcaag gcaaagttgg cccttctgga gcccctggtg aagatggtcg tcctggacct      1560
ccaggtcctc aggggctcg tgggcagcct ggtgtcatgg gtttccctgg ccccaaaggt      1620
gccaacggtg agcctggcaa agctggtgag aagggactgc ctggtgctcc tggtctgagg      1680
ggtcttcctg gcaaagatgg tgagacaggt gctgcaggac cccctggccc tgctggacct      1740
gctggtgaac gaggcgagca gggtgctcct gggccatctg ggttccaggg acttcctggc      1800
cctcctggtc ccccaggtga agtggaaaaa ccaggtgacc agggtgttcc cggtgaagct      1860
ggagcccctg gcctcgtggg tcccaggggt gaacgaggtt tcccaggtga acgtggctct      1920
cccggtgccc agggcctcca gggtccccgt ggcctccccg gcactcctgg cactgatggt      1980
cccaaaggtg catctggccc agcaggcccc cctgggggctc agggccctcc aggtcttcag      2040
ggaatgcctg gcgagagggg agcagctggt atcgctgggc caaaggtga cagggggtgac      2100 gttggtgaga aaggccctga gggagcccct ggaaaggatg gtggacgagg cctgacaggt      2160
cccattggcc ccctggccc agctggtgct aacggcgaga agggagaagt tggacctcct      2220
ggtcctgcag gaagtgctgg tgctcgtggc gctccgggtg aacgtggaga gactgggccc      2280
cccggaccag cgggatttgc tgggcctcct ggtgctgatg ccagcctgg ggccaagggt      2340 gagcaaggag aggccggcca gaaaggcgat gctggtgccc ctggtcctca gggcccctct      2400
ggagcacctg gcctcagggg tcctactgga gtgactggtc ctaaaggagc ccgaggtgcc      2460
caaggccccc cgggagccac tggattccct ggagctgctg ccgcgttgg acccccaggc      2520 tccaatggca accctggacc ccctggtccc cctggtcctt ctggaaaaga tggtcccaaa      2580
ggtgctcgag gagacagcgg ccccctggc cgagctggtg aacccggcct ccaaggtcct      2640
gctggacccc ctggcgagaa gggagagcct ggagatgacg tccctctgg tgccgaaggt      2700 ccaccaggtc cccagggtct ggctggtcag agaggcatcg tcggtctgcc tgggcaacgt      2760
ggtgagagag gattccctgg cttgcctggc ccgtcgggtg agcccggcaa gcagggtgct      2820
cctggagcat ctggagacag aggtcctcct ggccccgtgg gtcctcctgg cctgacgggt      2880
cctgcaggtg aacctggacg agagggaagc cccggtgctg atggcccccc tggcagagat      2940
ggcgctgctg gagtcaaggg tgatcgtggt gagactggtg ctgtgggagc tcctggagcc      3000
cctgggcccc ctggctcccc tggccccgct ggtccaactg gcaagcaagg agacagagga      3060
gaagctggtg cacaaggccc catgggaccc tcaggaccag ctggagcccg gggaatccag      3120
ggtcctcaag gccccagagg tgacaaagga gaggctggag agcctggcga gagaggcctg      3180
aagggacacc gtggcttcac tggtctgcag ggtctgcccg cccctcctgg tccttctgga      3240
gaccaaggtc cttctggtcc tgctggtcct tctggcccta gaggtcctcc tggccccgtc      3300 ggtcctctg gcaaagatgg tgctaatgga atccctggcc ccattgggcc tcctggtccc      3360
cgtggacgat caggcgaaac cggccctgct ggtcctcctg aaatcctgg accccctggt      3420 cctccaggtc cccctggccc tggcatcgac atgtccgcct ttgctggctt aggcccgaga      3480
gagaagggcc ccgacccccct gcagtacatg cgggccgacc aggcagccgg tggcctgaga      3540
cagcatgacg ccgaggtgga tgccacactc aagtccctca caaccagat tgagagcatc      3600 cgcagccccg agggctcccg caagaaccct gctcgcacct gcagagacct gaaactctgc      3660 cacccctgagt ggaagagtgg agactactgg attgacccca accaaggctg caccttggac      3720
```

| | |
|---|---:|
| gccatgaagg tttt ctgcaa catggagact ggcgagactt gcgtctaccc caatccagca | 3780 |
| aacgttccca agaagaactg gtggagcagc aagagcaagg agaagaaaca catctggttt | 3840 |
| ggagaaacca tcaatggtgg cttccatttc agctatggag atgacaatct ggctcccaac | 3900 |
| actgccaacg tccagatgac cttcctacgc ctgctgtcca cggaaggctc ccagaacatc | 3960 |
| acctaccact gcaagaacag cattgcctat ctggacgaag cagctggcaa cctcaagaag | 4020 |
| gccctgctca tccagggctc caatgacgtg agatccggg cagagggcaa tagcaggttc | 4080 |
| acgtacactg ccctgaagga tggctgcacg aaacataccg gtaagtgggg caagactgtt | 4140 |
| atcgagtacc ggtcacagaa gacctcacgc ctccccatca ttgacattgc acccatggac | 4200 |
| ataggagggc ccgagcagga attcggtgtg gacatagggc cggtctgctt cttgtaa | 4257 |

<210> SEQ ID NO 13
<211> LENGTH: 4401
<212> TYPE: DNA
<213> ORGANISM: Homo sapiens

<400> SEQUENCE: 13

| | |
|---|---:|
| atgatgagct ttgtgcaaaa ggggagctgg ctacttctcg ctctgcttca tcccactatt | 60 |
| attttggcac aacaggaagc tgttgaagga ggatgttccc atcttggtca gtcctatgcg | 120 |
| gatagagatg tctggaagcc agaaccatgc caaatatgtg tctgtgactc aggatccgtt | 180 |
| ctctgcgatg acataatatg tgacgatcaa gaattagact gccccaaccc agaaattcca | 240 |
| tttggagaat gttgtgcagt ttgcccacag cctccaactg ctcctactcg ccctcctaat | 300 |
| ggtcaaggac ctcaaggccc caagggagat ccaggccctc ctggtattcc tgggagaaat | 360 |
| ggtgaccctg gtattccagg acaaccaggt cccctggtt ctcctggccc cctggaatc | 420 |
| tgtgaatcat gccctactgg tcctcagaac tattctcccc agtatgattc atatgatgtc | 480 |
| aagtctggag tagcagtagg aggactcgca ggctatcctg gaccagctgg cccccaggc | 540 |
| cctcccggtc ccctggtac atctggtcat cctggttccc ctggatctcc aggataccaa | 600 |
| ggacccctg gtgaacctgg gcaagctggt ccttcaggcc ctccaggacc tcctggtgct | 660 |
| ataggtccat ctggtcctgc tggaaaagat ggagaatcag gtagacccgg acgacctgga | 720 |
| gagcgaggat tgcctggacc tcaggtatc aaaggtccag ctgggatacc tggattccct | 780 |
| ggtatgaaag gacacagagg cttcgatgga cgaaatggag aaaagggtga acaggtgct | 840 |
| cctggattaa agggtgaaaa tggtcttcca ggcgaaaatg gagctcctgg acccatgggt | 900 |
| ccaagagggg ctcctggtga gcgaggacgg ccaggacttc tggggctgc aggtgctcgg | 960 |
| ggtaatgacg gtgctcgagg cagtgatggt caaccaggcc ctcctggtcc tcctggaact | 1020 |
| gccggattcc ctggatcccc tggtgccaag ggtgaagttg gacctgcagg gtctcctggt | 1080 |
| tcaaatggtg ccctggaca aagaggagaa cctggacctc agggacacgc tggtgctcaa | 1140 |
| ggtcctcctg gcctcctgg gattaatggt agtcctggtg gtaaaggcga aatgggtccc | 1200 |
| gctggcattc ctggagctcc tggactgatg ggagcccggg gtcctccagg accagccggt | 1260 |
| gctaatggtg ctcctggact gcgaggtggt gcagtgagc ctggtaagaa tggtgccaaa | 1320 |
| ggagagcccg gaccacgtgg tgaacgcggt gaggctggca ttccaggtgt tccaggagct | 1380 |
| aaaggcgaag atggcaagga tggatcacct ggagaacctg gtcaaatgg cttccaggaa | 1440 |
| gctgcaggag aaaggggtgc ccctgggttc cgaggacctg ctggaccaaa tggcatccca | 1500 |
| ggagaaaagg gtcctgctgg agagcgtggt gctccaggcc ctgcagggcc cagaggagct | 1560 |
| gctggagaac ctggcagaga tggcgtccct ggaggtccag gaatgagggg catgcccgga | 1620 |

```
agtccaggag gaccaggaag tgatgggaaa ccagggcctc ccggaagtca aggagaaagt    1680
ggtcgaccag gtcctcctgg gccatctggt ccccgaggtc agcctggtgt catgggcttc    1740
cccggcccta aggaaatga tggtgctcct ggtaagaatg agaacgagg tggccctgga      1800 ggacctggcc ctcagggtcc tcctggaaag aatggtgaaa ctggacctca gggaccccca    1860
gggcctactg gcctggtgg tgacaaagga gacacaggac ccctggtcc acaaggatta     1920 caaggcttgc ctggtacagg tggtcctcca ggagaaaatg gaaaacctgg ggaaccaggt   1980
ccaaagggtg atgccggtgc acctggagct ccaggaggca agggtgatgc tggtgcccct    2040
ggtgaacgtg gacctcctgg attggcaggg gccccaggac ttagaggtgg agctggtccc    2100
cctggtcccg aaggaggaaa gggtgctgct ggtcctcctg ggccacctgg tgctgctggt    2160
actcctggtc tgcaaggaat gcctggagaa agaggaggtc ttggaagtcc tggtccaaag   2220
ggtgacaagg gtgaaccagg cggtccaggt gctgatggtg tcccagggaa agacggccca   2280
aggggtccta ctggtcctat tggtcctcct ggcccagctg gccagcctgg agataagggt   2340
gaaggtggtg cccccggact tccaggtata gctggacctc gtggtagccc tggtgagaga   2400
ggtgaaactg gccctccagg acctgctggt ttccctggtg ctcctggaca gaatggtgaa    2460
cctggtggta aaggagaaag aggggctccg ggtgagaaag gtgaaggagg ccctcctgga    2520
gttgcaggac cccctggagg ttctggacct gctggtcctc ctggtccccca aggtgtcaaa   2580 ggtgaacgtg gcagtcctgg tggacctggt gctgctggct ccctggtgc tcgtggtctt    2640 cctggtcctc ctggtagtaa tggtaaccca ggaccccag gtcccagcgg ttctccaggc    2700
aaggatgggc cccaggtcc tgcgggtaac actggtgctc ctggcagccc tggagtgtct   2760
ggaccaaaag gtgatgctgg ccaaccagga gagaagggat cgcctggtgc ccagggccca   2820
ccaggagctc caggcccact tgggattgct gggatcactg gagcacgggg tcttgcagga    2880
ccaccaggca tgccaggtcc taggggaagc cctggccccc agggtgtcaa gggtgaaagt    2940
gggaaaccag gagctaacgg tctcagtgga gaacgtggtc cccctggacc ccagggtctt    3000
cctggtctgg ctggtacagc tggtgaacct ggaagagatg gaaaccctgg atcagatggt    3060
cttccaggtc gagatggatc tcctggtggc aagggtgatc gtggtgaaaa tggctctcct    3120
ggtgcccctg gcgctcctgg tcatccgggc ccacctggtc ctgtcggtcc agctggaaag    3180
agtggtgaca gaggagaaag tggccctgct ggccctgctg tgctcccgg tcctgctggt    3240 tcccgaggtg ctcctggtcc tcaaggccca cgtggtgaca aggtgaaac aggtgaacgt    3300 ggagctgctg gcatcaaagg acatcgagga ttccctggta atccaggtgc ccaggttct     3360 ccaggccctg ctggtcagca gggtgcaatc ggcagtccag gacctgcagg ccccagagga   3420
cctgttggac ccagtggacc tcctggcaaa gatggaacca gtggacatcc aggtcccatt    3480
ggaccaccag gcctcgagg taacagaggt gaaagaggat ctgagggctc cccaggccac   3540
ccagggcaac caggccctcc tggacctcct ggtgcccctg gtccttgctg tggtggtgtt    3600
ggagccgctg ccattgctgg gattggaggt gaaaaagctg gcggttttgc cccgtattat    3660
ggagatgaac caatgggttt caaaaatcaac accgatgaga ttatgacttc actcaagtct    3720
gttaatggac aaatagaaag cctcattagt cctgatggtt ctcgtaaaaa ccccgctaga    3780
aactgcagag acctgaaatt ctgccatcct gaactcaaga gtggagaata ctgggttgac    3840
cctaaccaag gatgcaaatt ggatgctatc aaggtattct gtaatatgga aactggggaa    3900
acatgcataa gtgccaatcc tttgaatgtt ccacggaaac actggggac agattctagt    3960 gctgagaaga aacacgtttg gtttggagag tccatggatg gtggttttca gtttagctac    4020
```

```
ggcaatcctg aacttcctga agatgtcctt gatgtgcagc tggcattcct tcgacttctc    4080
tccagccgag cttcccagaa catcacatat cactgcaaaa atagcattgc atacatggat    4140
caggccagtg gaaatgtaaa gaaggccctg aagctgatgg ggtcaaatga aggtgaattc    4200
aaggctgaag gaaatagcaa attcacctac acagttctgg aggatggttg cacgaaacac    4260
actggggaat ggagcaaaac agtctttgaa tatcgaacac gcaaggctgt gagactacct    4320
attgtagata ttgcacccta tgacattggt ggtcctgatc aagaatttgg tgtggacgtt    4380
ggccctgttt gcttttttata a                                             4401
```

<210> SEQ ID NO 14
<211> LENGTH: 5848
<212> TYPE: DNA
<213> ORGANISM: Artificial
<220> FEATURE:
<223> OTHER INFORMATION: An artificially synthesized nucleotide sequence

<400> SEQUENCE: 14

```
cgatgtacgg gccagatata cgcgttgaca ttgattattg actagttatt aatagtaatc      60
aattacgggg tcattagttc atagcccata tatggagttc cgcgttacat aacttacggt     120
aaatggcccg cctggctgac cgcccaacga cccccgccca ttgacgtcaa taatgacgta     180
tgttcccata gtaacgccaa tagggacttt ccattgacgt caatgggtgg agtatttacg     240
gtaaactgcc cacttggcag tacatcaagt gtatcatatg ccaagtacgc cccctattga     300
cgtcaatgac ggtaaatggc ccgcctggca ttatgcccag tacatgacct tatgggactt     360
tcctacttgg cagtacatct acgtattagt catcgctatt accatggtga tgcggttttg     420
gcagtacatc aatgggcgtg atagcggttt gactcacggg gatttccaa gtctccaccc     480 cattgacgtc aatgggagtt tgttttggca ccaaaatcaa cgggactttc caaaatgtcg     540
taacaactcc gccccattga cgcaaatggg cggtaggcgt gtacggtggg aggtctatat     600
aagcagagct ctctggctaa ctagagaacc cactgttaac tggcttatcg aaattgtcga     660
ggagaacttc agggtgagtt tggggacccct tgattgttct ttcttttcg ctattgtaaa     720 attcatgtta tatggagggg gcaaagtttt cagggtgttg tttagaatgg aaagatgtcc     780
cttgtatcac catggaccct catgataatt tgtttctttt cactttctac tctgttgaca     840
accattgtct cctcttattt tcttttcatt ttctgtaact ttttcgttaa actttagctt     900
gcatttgtaa cgaatttta aattcacttt tgtttatttg tcagattgta agtactttct     960
ctaatcactt tttttcaag gcaatcaggg tatattatat tgtacttcag cacagtttta    1020
gagaacaatt gttataatta aatgataagg tagaatattt ctgcatataa attctggctg    1080
gcgtggaaat attcttattg gtagaaacaa ctacatcctg gtcatcatcc tgcctttctc    1140
tttatggtta caatgatata cactgtttga gatgaggata aaatactctg agtccaaacc    1200
gggcccctct gctaaccatg ttcatgcctt cttctttttc ctacagctcc tgggcaacgt    1260
gctggcggcc gccttctaga gcctcgactg tgccttctag ttgccagcca tctgttgttt    1320
gcccctcccc cgtgccttcc ttgacccctgg aaggtgccac tcccactgtc ctttcctaat    1380
aaaatgagga aattgcatcg cattgtctga gtaggtgtca ttctattctg ggggtgggg    1440 tggggcagga cagcaagggg gaggattggg aagacaatag caggcatgct ggggaggatc    1500
tccgcggtgt ggaatgtgtg tcagttaggg tgtggaaagt ccccaggctc cccagcaggc    1560
agaagtatgc aaagcatgca tctcaattag tcagcaacca tagtcccgcc ctaactccg     1620 cccatcccgc ccctaactcc gcccagttcc gcccattctc cgccccatgg ctgactaatt    1680
```

```
tttttttattt atgcagaggc cgaggccgcc tcggcctctg agctattcca gaagtagtga    1740
ggaggctttt ttggaggcct aggcttttgc aaaaaagctg cagatggtac gaccattaaa    1800
ttgtattgta gcagtatcac aaaatatggg tattggtaaa aatggtgatt taccatggcc    1860
accattacga aatgaattta aatatttcca acgaatgact actacttcat cagtagaagg    1920
taaacaaaat ttagtaatta tgggtcgaaa aacttggttt tcaattcctg agaagaatcg    1980
acctttaaag gacagaatta atatagttct cagtagagaa ctcaaagaac caccacgagg    2040
agctcatttt cttgccaaaa gtttggatga tgccttaaga cttattgaac aaccggaatt    2100
ggcaagtaaa gtagacatgg tttggatagt cggaggcagt tctgtttacc aggaagccat    2160
gaatcaacca ggccacctca gactctttgt gacaaggatc atgcaggaat ttgaaagtga    2220
cacgttttc ccagaaattg atttggggaa atataaactt ctcccagaat acccaggcgt    2280
cctctctgag gtccaggagg aaaaaggcat caagtataag tttgaagtct acgagaagaa    2340
agactaaaga tccgtgacat aattggacaa actacctaca gagatttaaa gctctaaggt    2400
aaatataaaa ttttaagtg tataatgtgt taaactactg attctaattg tttgtgtatt    2460
ttagattcca acctatggaa ctgatgaatg ggagcagtgg tggaatgcct ttaatgagga    2520
aaacctgttt tgctcagaag aaatgccatc tagtgatgat gaggctactg ctgactctca    2580
acattctact cctccaaaaa agaagagaaa ggtagaagac cccaaggact ttccttcaga    2640
attgctaagt tttttgagtc atgctgtgtt tagtaataga actcttgctt gctttgctat    2700
ttacaccaca aaggaaaaag ctgcactgct ataacagaaa attatggaaa aatattctgt    2760
aaccttatta agtaggcata acagttataa tcataacata ctgtttttc ttactccaca    2820
caggcataga gtgtctgcta ttaataacta tgctcaaaaa ttgtgtacct ttagcttttt    2880
aatttgtaaa gggtttaata aggaatattt gatgtatagt gccttgacta gagatcataa    2940
tcagccatac cacatttgta gaggttttac ttgctttaaa aaacctccca cacctccccc    3000
tgaacctgaa acataaaatg aatgcaattg ttgttgttaa cttgtttatt gcagcttata    3060
atggttacaa ataaagcaat agcatcacaa atttcacaaa taaagcattt ttttcactgc    3120
attctagttg tggtttgtcc aaactcatca atgtatctta tcatgtctgg gcccatcgat    3180
gaattcaacg tacgtagctt ggcactggcc gtcgttttac aacgtcgtga ctgggaaaac    3240
cctggcgtta cccaacttaa tcgccttgca gcacatcccc ctttcgccag ctggcgtaat    3300
agcgaagagg cccgcaccga tcgcccttcc caacagttgc gcagcctgaa tggcgaatgg    3360
cgcctgatgc ggtattttct ccttacgcat ctgtgcggta tttcacaccg catatggtgc    3420
actctcagta caatctgctc tgatgccgca tagttaagcc agccccgaca cccgccaaca    3480
cccgctgacg cgccctgacg ggcttgtctg ctcccggcat ccgcttacag acaagctgtg    3540
accgtctccg ggagctgcat gtgtcagagg ttttcaccgt catcaccgaa acgcgcgagg    3600
acgaaagggc ctcgtgatac gcctattttt ataggttaat gtcatgataa taatggtttc    3660
ttagacgtca ggtggcactt ttcggggaaa tgtgcgcgga acccctattt gtttattttt    3720
ctaaatacat tcaaatatgt atccgctcat gagacaataa ccctgataaa tgcttcaata    3780
atattgaaaa aggaagagta tgagtattca acatttccgt gtcgccctta ttccctttt    3840
tgcggcattt tgccttcctg ttttgctcta cccagaaacg ctggtgaaag taaaagatgc    3900
tgaagatcag ttgggtgcac gagtgggtta catcgaactg gatctcaaca gcggtaagat    3960
ccttgagagt tttcgccccg aagaacgttt tccaatgatg agcactttta aagttctgct    4020
atgtggcgcg gtattatccc gtattgacgc cgggcaagag caactcggtc gccgcataca    4080
```

```
ctattctcag aatgacttgg ttgagtactc accagtcaca gaaaagcatc ttacggatgg    4140
catgacagta agagaattat gcagtgctgc cataaccatg agtgataaca ctgcggccaa    4200
cttacttctg acaacgatcg gaggaccgaa ggagctaacc gcttttttgc acaacatggg    4260
ggatcatgta actcgccttg atcgttggga accggagctg aatgaagcca taccaaacga    4320
cgagcgtgac accacgatgc ctgtagcaat ggcaacaacg ttgcgcaaac tattaactgg    4380
cgaactactt actctagctt cccggcaaca attaatagac tggatggagg cggataaagt    4440
tgcaggacca cttctgcgct cggcccttcc ggctggctgg tttattgctg ataaatctgg    4500
agccggtgag cgtgggtctc gcggtatcat tgcagcactg gggccagatg gtaagccctc    4560
ccgtatcgta gttatctaca cgacggggag tcaggcaact atggatgaac gaaatagaca    4620
gatcgctgag ataggtgcct cactgattaa gcattggtaa ctgtcagacc aagtttactc    4680
atatatactt tagattgatt taaaacttca ttttttaattt aaaaggatct aggtgaagat    4740 ccttttttgat aatctcatga ccaaaatccc ttaacgtgag ttttcgttcc actgagcgtc    4800
agaccccgta gaaaagatca aaggatcttc ttgagatcct ttttttctgc gcgtaatctg    4860
ctgcttgcaa acaaaaaaac caccgctacc agcggtggtt tgtttgccgg atcaagagct    4920
accaactctt tttccgaagg taactggctt cagcagagcg cagataccaa atactgtcct    4980
tctagtgtag ccgtagttag gccaccactt caagaactct gtagcaccgc ctacatacct    5040
cgctctgcta atcctgttac cagtggctgc tgccagtggc gataagtcgt gtcttaccgg    5100
gttggactca agacgatagt taccggataa ggcgcagcgg tcgggctgaa cggggggttc    5160
gtgcacacag cccagcttgg agcgaacgac ctacaccgaa ctgagatacc tacagcgtga    5220
gcattgagaa agcgccacgc ttcccgaagg gagaaaggcg gacaggtatc cggtaagcgg    5280
cagggtcgga acaggagagc gcacgaggga gcttccaggg ggaaacgcct ggtatcttta    5340
tagtcctgtc gggtttcgcc acctctgact tgagcgtcga tttttgtgat gctcgtcagg    5400
ggggcggagc ctatgaaaaa cgccagcaa cgcggccttt ttacggttcc tggccttttg    5460
ctggcctttt gctcacatgt tctttcctgc gttatcccct gattctgtgg ataaccgtat    5520
taccgccttt gagtgagctg ataccgctcg ccgcagccga acgaccgagc gcagcgagtc    5580
agtgagcgag gaagcggaag agcgcccaat acgcaaaccg cctctccccg cgcgttggcc    5640
gattcattaa tgcagctggc acgacaggtt tcccgactgg aaagcgggca gtgagcgcaa    5700
cgcaattaat gtgagttagc tcactcatta ggcaccccag ctttacact ttatgcttcc    5760 ggctcgtatg ttgtgtggaa ttgtgagcgg ataacaattt cacacaggaa acagctatga    5820
ccatgattac gaatttcgta cgaagctt                                      5848
```

<210> SEQ ID NO 15
<211> LENGTH: 698
<212> TYPE: DNA
<213> ORGANISM: Artificial
<220> FEATURE:
<223> OTHER INFORMATION: An artificially synthesized nucleotide sequence

<400> SEQUENCE: 15

```
ggccgccacc atgctgctct tcctcctctc tgcactggtc ctgctcacac agcccctggg     60
ctacctggaa gcagaaatga agacctactc ccacagaaca atgcccagtg cttgcaccct    120
ggtcatgtgt agctcagtgg agtccggaaa ggctggagag cgaggtgttc ccggaccccc    180
tggcgctgtc ggtcctgctg gcaaagatgg agaggctgga gctcagggac ccctggccc    240 tgctggtccc gctggcgaga gaggtgaaca aggccctgct ggctcccccg gattccaggg    300
```

```
tctccctggt cctgctggtc ctccaggtga agcaggcaaa cctggtgaac agggtgttcc    360
tggagacctt ggcgcccctg gcccctctgg agcaagaggc gagagaggtt tccctggcga    420
gcgtggtgtg caaggtcccc ctggtcctgc tggtccccga ggggccaacg gtgctcccgg    480
caacgatggt gctaagggtg atgctggtgc ccctggagct cccggtagcc agggcgcccc    540
tggccttcag ggaatgcctg gtgaacgtgg tgcagctggt cttccagggc ctaagggtga    600
cagaggtgat gctggtccca aaggtgctga tggctctcct ggcaaagatg gcgtccgtgg    660
tctgaccggc cccattcacc accaccacca ccactagt                           698
```

PROTEIN SUBSTANCE HAVING TRIPLE HELIX STRUCTURE AND MANUFACTURING METHOD THEREFOR

TECHNICAL FIELD

The present invention relates to proteins having a triple-helix structure and methods for producing them. More specifically, the present invention relates to human-type collagen analogs and methods for producing them. An objective of the present invention is to provide collagen analogs composed of human-type recombinant proteins which are safe for living organisms and can be easily purified and obtained, and methods for producing them. More specifically, the present invention provides methods for producing collagen analogs composed of a recombinant protein in which the introduced genes are all human-type, wherein the method is carried out by stable transduction of a mammalian expression vector inserted with a cDNA of a human-type collagen-comprising recombinant protein into Chinese hamster ovary (CHO) cells.

BACKGROUND ART

In recent years, an example of one of the most important materials in regenerative medicine is collagen. Collagen is a representative protein distributed in nearly all tissues (skin, bone, cartilage, and such) in living organisms, and it is well known that it has important functions in living organisms such as maintaining the structure of biological tissues and organs by becoming a scaffold for cells. In addition, it has various physiological functions that regulate the proliferation, differentiation, and migration of cells. From these facts, it is receiving attention in the field of regenerative medicine through its use together with cells, growth factors, and such in tissue engineering medicine. So far, collagen has been used widely in the medical field as artificial organ implants (Patent Document 1), sustained drug release matrices (Patent Document 2), artificial skin (Patent Document 3), and components of biocompatible materials for use in bandage matrices for wounds and matrices for wound treatment (Patent Document 4).

Forty percent of all collagen of a living organism is in the skin, and 70% or more of the dry weight of the skin/tendon is collagen. Therefore, collagen is important in the development of artificial skin. In particular, collagen is used as a biomaterial for repairing damages in organisms. For example, it is used as a coating material for sites of skin lesion such as a burn, and healing and improvement have been reported (Non-Patent Documents 1 and 2). This means that one can have great hope for applications in the current significantly progressed field of regenerative medicine. Furthermore, it is utilized as a material useful in techniques for culturing cells and organs (Patent Documents 5 and 6). In addition, it has been pointed out that oral ingestion of collagen (type II collagen) and such may be used to suppress rheumatoid arthritis (Non-Patent Document 3). Furthermore, it has been reported that it is possible to treat by designing a gene to express a partial peptide of human collagen (type VII collagen), and introducing a low-molecular-weight collagen gene into epidermolysis bullosa cells (Non-Patent Document 4).

Many of the collagens used at present are derived from non-human mammalian species such as bovine or pigs. It is reported that when these collagens are transplanted into humans, allergic reaction occurs in approximately 3% of the patients (Non-Patent Documents 5 and 6). Furthermore, in recent years, the risk of contamination of collagen derived from non-human mammalian species with prions or pathogens has become a major problem. Therefore, a system for producing safe human-type collagens with low antigenicity and free of risk of pathogen contamination is strongly desired.

To avoid such problems, some inventors have invented a method for producing recombinant human collagen having a triple helix structure equivalent to that in a human body by infecting insect cells with a recombinant virus inserted with a cDNA encoding human collagen, and have applied for a patent (Patent Document 7). Furthermore, methods for producing human collagen using mammalian cells or yeast cells have also been devised (Patent Document 8).

PRIOR ART DOCUMENTS

Patent Documents
[Patent Document 1] Japanese Patent Application Kokai Publication No. (JP-A) 2007-204881 (unexamined, published Japanese patent application)
[Patent Document 2] JP-A (Kokai) 2001-316282
[Patent Document 3] JP-A (Kokai) 2005-314
[Patent Document 4] JP-A (Kokai) 2007-160092
[Patent Document 5] JP-A (Kokai) 2002-142753
[Patent Document 6] Japanese Patent Application Saikohyo Publication No. (JP-A) 2005-014774 (unexamined Japanese national phase publication corresponding to a Japanese international publication)
[Patent Document 7] JP-A (Kokai) 8-23979
[Patent Document 8] Japanese Patent Application Kohyo Publication No. (JP-A) 7-501939 (unexamined Japanese national phase publication corresponding to a non-Japanese international publication)
Non-Patent Documents
[Non-Patent Document 1] Surg. Forum, 10, 303 (1960)
[Non-Patent Document 2] J. Surg. Res., 10, 485-491 (1960)
[Non-Patent Document 3] Science, 261, 1727-1730 (1993)
[Non-Patent Document 4] THE JOURNAL OF BIOLOGICAL CHEMISTRY Vol. 275, No. 32, Issue of August 11, pp. 24429-24435, 2000
[Non-Patent Document 5] J. Immunol. 136:877-882, 1986
[Non-Patent Document 6] Biomaterials 11:176-180, 1990

SUMMARY OF THE INVENTION

Problems to be Solved by the Invention

In this way, collagen is a substance useful as a pharmaceutical product or a biomaterial for live-donor transplantation or regenerative medicine; however, conventionally used collagen is derived from tissues of non-human mammalian species such as pigs and cattle. Collagen is originally a protein with low immunogenicity, and is being transplanted, embedded or administered into the human body as a biomaterial. However, although in low frequency, there are reports that immune reactions are evoked by collagen derived from tissues of non-human mammalian species (J. Immunol., 136, 877-882 (1986); Biomaterials, 11, 176-180 (1990)). Furthermore, due to the possibility of prion contamination suggested in the case of cattle, it is not possible to use cattle-derived collagen. In addition, there is no guarantee that unknown contaminants (pathogenic viruses and such) like prion contamination are not contained in mammals such as pigs which are currently used for the purification and extraction of collagen, and safety problems are being raised with using collagen derived from non-human mammals to humans. Additionally, a problem with biologically-derived collagen is that multi-step purification becomes necessary during purification due to the inclusion of large amount of contaminant proteins, and the purification method becomes complicated.

In light of the above-mentioned issues, human-derived collagen is desirable as a biomaterial to be used directly on humans. Human derived collagen may be purified from human sources (such as human placenta) (U.S. Pat. Nos. 5,002,071 and 5,428,022). However, there are several problems in the use of human-derived collagen: (1) since the material is human tissue, the material has limited supply; (2) one cannot completely eliminate the possibility of contamination with pathogenic viruses such as hepatitis viruses and human immunodeficiency viruses (HIV); (3) the types of collagen collected from the placenta are disproportionate and the qualities are not completely identical; and (4) there are ethical problems regarding the extraction and purification of collagen from humans. The qualitative problem also exists as purification becomes difficult due to formation of unspecified bridges in the obtained collagen.

So far, methods that use genetic engineering techniques for producing collagen have been investigated to eliminate the risk of pathogen contamination and to obtain large amounts of collagen for which the isolation and purification steps are easy (Biochem. Soc., 28, 350-353 (2000)). However, the molecular weight of a collagen molecule is 100,000 or more and is very large, and production of an expression vector for introduction into host cells is very complicated. In addition, conventional methods did not yield production levels that can sustain practical applications. Furthermore, collagen is a molecule that adopts a triple helix structure in which three polypeptide chains are assembled, and such structure is formed by undergoing a number of posttranslational modifications (N. Engl. J. Med., 311, 376-386 (1984)), but only specific cells are expected to possess such modification abilities.

It is known that in order for collagen to form a triple helix structure, prolines in the collagen domain must be hydroxylated. To produce collagen having a triple helix structure, a method for producing recombinant collagen by coexpressing human collagen and proline hydroxylase in insect cells was provided (JP-A (Kokai) 2002-315580). However, to coexpress proline hydroxylase, at least three genes, i.e. collagen and the α subunit and β subunit of proline hydroxylase, must be coexpressed and cloning of the cells becomes very complicated.

Production of human-derived recombinant collagen using hamster embryonic cells, mouse fibroblast cells, and such as hosts has been tested from before (Proc. Natl. Acad. Sci. USA., 84, 764-768 (1987); J. Biol. Chem., 264, 20683-20687 (1989)). The molecular structures of collagens obtained in these examples were normal, but host cell-derived collagen and foreign gene-derived collagen were mixed. Furthermore, in an example where type II collagen was expressed in human fibrosarcoma cells HT1080 (Biochem. J., 298, 31-37 (1994)), the production level was low (0.5 to 1 mg per 1 L of culture), and this was not sustainable for practical use. Furthermore, an equal amount of human fibrosarcoma cell HT1080-derived type IV collagen as that of the foreign gene-derived type II collagen was observed. Therefore, the foreign gene-derived type II collagen had to be separated from endogenous type IV collagen, and it was also impractical in this regard. Therefore, even if an expression system is used, it becomes necessary to examine the meticulous purification conditions, and it was considered that even under conditions of mixed contaminants, a simple and enabling purification method is necessary.

In addition to the above, there are examples in which human collagen was expressed using yeast (JP-A (Kohyo) H07-501939), insect cells (JP-A (Kokai) H08-23979), *Bacillus brevis* (JP-A (Kokai) H11-178574), and *Escherichia coli* (JP-A (Kokai) 2002-325584). However, these may have the risk of producing collagen with different posttranslational modifications from those of naturally-occurring human collagen. As described above, all methods indicated so far are not sustainable for practical use as means for producing human collagen by genetic engineering, both qualitatively and quantitatively. Furthermore, methods for producing a large amount of protein having a triple helix structure, such as a recombinant collagen designed to have low molecular weight had not been examined so far.

In view of the above circumstances, the applicants have investigated production of human type I collagen by applying genetic engineering techniques to obtain non-antigenic collagen, eliminate the danger of pathogen contamination, and obtain collagen that is easy to isolate and purify (International Publication WO 2006/106970). Although conventional methods could secure a certain level of production, a system in which more triple helix structures are formed was needed. Improvement was considered necessary also in terms of expression level.

The present invention was achieved in view of the above circumstances. An objective of the present invention is to provide safe human-type collagen analog proteins having a triple helix structure, and methods for producing them.

Means for Solving the Problems

The present inventors conducted various examinations to solve the above-mentioned problems and successfully produced easily purified collagen analogs (mini collagens) that have a triple helix structure and a molecular weight smaller than those of naturally-occurring-type collagens, by introducing into host cells a construct produced by fusing a signal peptide domain gene of human collectin and a cysteine-rich domain gene of human collectin to the amino-terminal side, and a neck domain gene of human collectin and a carbohydrate recognition domain gene of human collectin to the carboxy-terminal side of the collagen domain of the collagen gene which is a protein having triple helix structure.

Examples of known proteins having a triple helix structure include human mannan-binding lectin (MBL) and conglutinin. By reducing the molecular weight of the collagen analogs of the present invention to be close to those of these proteins, collagen analog proteins having a triple helix structure with reduced molecular weight, which had been difficult to realize to date, were successfully produced. Furthermore, these collagen analog proteins were shown to have a triple helix structure and thermal stability.

Naturally-occurring human collagen has poor water solubility, whereas the collagen analogs of the present invention show high water solubility since they comprise the water-soluble cysteine-rich domain, neck domain, and carbohydrate recognition domain of human collectin. Therefore, they are easier to handle compared to naturally-occurring collagens which have a high molecular weight.

The present inventors precipitated the collagen analogs by promoting fibril formation by adding a high concentration of neutral salt, and successfully and easily purified fibrous collagen analogs having a triple helix structure by centrifugation.

Furthermore, the present inventors successfully purified water-soluble collagen analogs by a simple one-step purification method, using mannan agarose which utilizes the binding of the carbohydrate recognition domain to mannan.

Using the different purification methods described above, the present inventors successfully purified two collagen analogs having different physical properties: a fibrous collagen analog with high physical strength; and a water-soluble collagen with high solubility that binds to mannan. These collagen analogs were shown to have the same degrees of cellular adhesiveness and elongation properties as naturally-occurring human collagen when used as biomaterial in human adherent cells. Collagen analogs of the present invention can be expected to be useful as replacements for conventionally used collagen derived from non-human mammalian species, or as biomaterials for use in humans.

As a result of conducting various examinations to solve the above-mentioned problems, the present inventors invented a collagen gene construct that can be easily purified and which maintain a triple helix structure equivalent to that of naturally-occurring collagen while having a low molecular weight. Specifically, because CR-D (a signal peptide) has a carbohydrate recognition domain, one-step purification by affinity purification is enabled. By substituting a portion of a human collagen structural gene of the present invention with the collagen-like structural gene portion of MBL, it has become possible to obtain low-molecular-weight collagens maintaining a triple helix structure in large quantities and with high purity.

More specifically, the present inventors successfully produced large amounts of human collagen analogs by introducing a construct in which a collagen analog gene of the present invention is contained in a vector capable of highly expressing a foreign gene using as host Chinese hamster ovary (CHO) cells which (1) have been used for producing pharmaceuticals and are confirmed to be safe and (2) are thought to have sugar chain modifications and such of proteins that are close to those of humans since they are mammalian cells.

More specifically, the present inventors successfully developed a method for producing large quantities of collagen analogs of the present invention without the need for complicated purification steps, by minimizing the mixture of host-derived collagen and foreign gene-derived collagen, using mammalian cells that have a low expression level of collagen (a protein having triple helix structure) as host. From the above, the present invention was completed.

Specifically, the present invention provides the following:
[1] a recombinant protein having a triple helix structure, which comprises a protein encoded by a polynucleotide comprising (i) to (v) below in order from the amino terminus:
(i) a signal peptide domain gene of human collectin;
(ii) a cysteine-rich domain gene of human collectin;
(iii) a collagen domain gene of human collagen;
(iv) a neck domain gene of human collectin; and
(v) a carbohydrate recognition domain gene of human collectin;
[2] the recombinant protein having a triple helix structure of [1], wherein the signal peptide domain gene of human collectin is a signal peptide domain gene of human surfactant protein D (SP-D) and a polynucleotide comprising the nucleotide sequence of SEQ ID NO: 4;
[3] the recombinant protein having a triple helix structure of [1], wherein the cysteine-rich domain gene of human collectin is a cysteine-rich domain gene of human surfactant protein D (SP-D) and a polynucleotide comprising the nucleotide sequence of SEQ ID NO: 5;
[4] the recombinant protein having a triple helix structure of [1], wherein the neck domain gene of human collectin is a neck domain gene of human mannan-binding lectin (MBL) and a polynucleotide comprising the nucleotide sequence of SEQ ID NO: 6;
[5] the recombinant protein having a triple helix structure of [1], wherein the carbohydrate recognition domain gene of human collectin is a carbohydrate recognition domain gene of human mannan-binding lectin (MBL) and a polynucleotide comprising the nucleotide sequence of SEQ ID NO: 7;
[6] the recombinant protein having a triple helix structure of [1], wherein the collagen domain gene of human collagen comprises at least one or more types of collagen domain genes of α-chain human collagens;
[7] the recombinant protein having a triple helix structure of [1], wherein the collagen domain gene of human collagen is a collagen domain gene of a human type I collagen comprising an α-chain human collagen;
[8] the recombinant protein having a triple helix structure of [6] or [7], wherein the collagen domain gene of an α-chain human collagen is a polynucleotide comprising the nucleotide sequence of SEQ ID NO: 8;
[9] the recombinant protein having a triple helix structure of [1], which comprises a protein comprising the amino acid sequence of SEQ ID NO: 1;
[10] the recombinant protein having a triple helix structure of [1], wherein the polynucleotide is a polynucleotide comprising the nucleotide sequence of SEQ ID NO: 3;
[11] a method for producing a protein having a triple helix structure, wherein the method comprises the steps of:
(a) introducing into a vector a polynucleotide comprising (i) to (v) below in order from the amino terminus:
(i) a signal peptide domain gene of human collectin;
(ii) a cysteine-rich domain gene of human collectin;
(iii) a collagen domain gene of human collagen;
(iv) a neck domain gene of human collectin; and
(v) a carbohydrate recognition domain gene of human collectin;
(b) transforming a host cell by gene introduction using the vector; and
(c) culturing or breeding the transformant, and collecting a protein having a triple helix structure from the cell or its culture supernatant;
[12] the method of [11], wherein the signal peptide domain gene of human collectin is a signal peptide domain gene of human surfactant protein D (SP-D) and a polynucleotide comprising the nucleotide sequence of SEQ ID NO: 4;
[13] the method of [11], wherein the cysteine-rich domain gene of human collectin is a cysteine-rich domain gene of human surfactant protein D (SP-D) and a polynucleotide comprising the nucleotide sequence of SEQ ID NO: 5;
[14] the method of [11], wherein the neck domain gene of human collectin is a neck domain gene of human mannan-binding lectin (MBL) and a polynucleotide comprising the nucleotide sequence of SEQ ID NO: 6;
[15] the method of [11], wherein the carbohydrate recognition domain gene of human collectin is a carbohydrate recognition domain gene of human mannan-binding lectin (MBL) and a polynucleotide comprising the nucleotide sequence of SEQ ID NO: 7;
[16] the method of [11], wherein the collagen domain gene of human collagen comprises at least one or more types of collagen domain genes of α-chain human collagens;
[17] the method of [11], wherein the collagen domain gene of human collagen is a collagen domain gene of a human type I collagen comprising an α-chain human collagen;

[18] the method of [16] or [17], wherein the collagen domain gene of an α-chain human collagen is a polynucleotide comprising the nucleotide sequence of SEQ ID NO: 8;

[19] the method of [11], wherein the vector used in step (a) is pNC1 of SEQ ID NO: 2; and

[20] the method of [11], wherein the vector used in step (a) is pDC6/CF of SEQ ID NO: 9.

MODE FOR CARRYING OUT THE INVENTION

Figure 1:
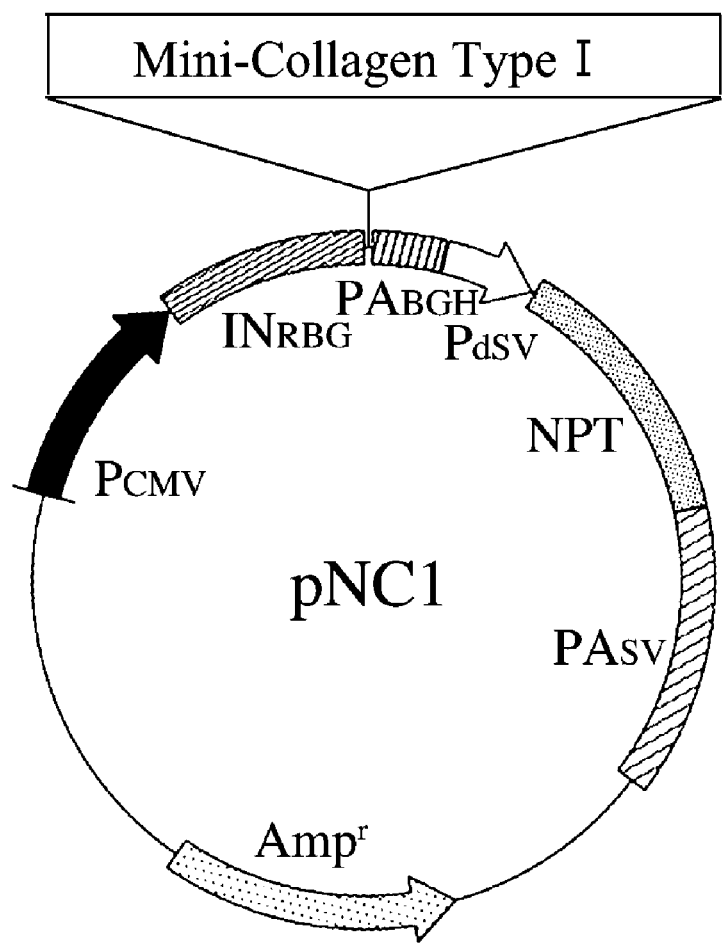
FIG. 1 shows the pNC1/Mini-Collagen Type I construct with the respective abbreviations shown below. PCMV: cytomegalovirus promoter; INRBG: rabbit growth hormone intron; Mini-Collagen Type I: mini-collagen DNA; PABGH: bovine growth hormone gene polyA addition signal; PdSV: enhancer-deleted simian virus 40 promoter; NPT: neomycin phosphotransferase cDNA; PASV: simian virus 40 polyA addition signal; and Amp$^r$: selection marker (ampicillin resistance) in E. coli.

Herein below, modes for carrying out the present invention will be shown, and the present invention will be explained in more detail.

The present invention relates to a recombinant protein having a triple helix structure, which comprises a protein encoded by a polynucleotide comprising (i) to (v) below in order from the amino terminus:
(i) the signal peptide domain gene of human collectin;
(ii) the cysteine-rich domain gene of human collectin;
(iii) the collagen domain gene of human collagen;
(iv) the neck domain gene of human collectin; and
(v) the carbohydrate recognition domain gene of human collectin.

In the present invention a "protein having a triple helix structure" may be a protein in which a triple helix is constructed at the stage of production by culturing, or a protein in which a triple helix structure is formed through operations such as purification after production by culturing. Although it is a protein that may take a triple-helix structure, it may be produced in large amounts in the form of a single-stranded structure. The protein that may form a triple helix structure may be part of the expressed proteins.

In the present invention, the "signal peptide domain gene of human collectin" is not particularly limited, but is preferably exemplified by the "signal peptide domain gene of human surfactant protein D (SP-D)" or more preferably a polynucleotide comprising the nucleotide sequence of SEQ ID NO: 4.

In the present invention, the "cysteine-rich domain gene of human collectin" is not particularly limited, but is preferably exemplified by the "cysteine-rich domain gene of human surfactant protein D (SP-D)" or more preferably a polynucleotide comprising the nucleotide sequence of SEQ ID NO: 5.

In the present invention, the "neck domain gene of human collectin" is not particularly limited, but is preferably exemplified by the "neck domain gene of human mannan-binding lectin (MBL)" or more preferably a polynucleotide comprising the nucleotide sequence of SEQ ID NO: 6.

In the present invention, the "carbohydrate recognition domain gene of human collectin" is not particularly limited, but is preferably exemplified by the "carbohydrate recognition domain gene of human mannan-binding lectin (MBL)" or more preferably a polynucleotide comprising the nucleotide sequence of SEQ ID NO: 7.

In the present invention, the "collagen domain gene of human collagen" is not particularly limited, but the gene preferably comprises at least one or more types of collagen domain genes of α-chain human collagens. Furthermore, this gene is preferably a collagen domain gene of human type I collagen composed of α chain human collagen. An example of the collagen domain gene of α-chain human collagen of the present invention is more preferably a polynucleotide comprising the nucleotide sequence of SEQ ID NO: 8. Furthermore, it may be a collagen domain gene lacking the region from the C-terminal region to the GPP region of the collagen domain gene. An example of such collagen domain gene lacking the portion from the C-terminal region to the GPP region is more preferably a polynucleotide comprising the nucleotide sequence of SEQ ID NO: 15.

More than 20 different types of collagen and about 25 types of constituting α chains are known. Genes encoding them have been cloned and nucleotide sequences thereof have been elucidated ("Connective Tissue and Its Heritable Disorders", pp 145-165, published by Weily-Liss Inc. (1992)). These genes can be introduced into a vector used in the present invention that can highly express foreign genes by gene recombination techniques known to those skilled in the art (for example, "Molecular Cloning" second edition, published by Cold Spring Harbor Laboratory Press (1989)). The human collagen cDNA used in the present invention may be any one of these cloned cDNAs of collagen, and includes cDNAs of partial collagen peptides.

The type of the collagen of the present invention is not specifically limited, but mammalian-type collagen is preferable, and human-type collagen is more preferable.

Furthermore, the protein having a triple helix structure of the present invention also includes a protein having a triple helix structure of the present invention whose amino acid sequence is partially modified by substitution, deletion, or such. In addition, there are known methods for obtaining transduced cells expressing protein molecules by introducing a vector into host mammalian cells. Similar methods can be applied to the present invention.

A "protein having a triple helix structure" of the present invention is more preferably exemplified by a recombinant protein having a triple helix structure, including a protein comprising the amino acid sequence of SEQ ID NO: 1 and a protein encoded by a polynucleotide comprising the nucleotide sequence of SEQ ID NO: 3.

Furthermore, the present invention relates to a method for producing a protein having a triple helix structure, comprising the steps of:
(a) introducing into a vector a polynucleotide comprising (i) to (v) below in order from the amino terminus:
  (i) the signal peptide domain gene of human collectin;
  (ii) the cysteine-rich domain gene of human collectin;
  (iii) the collagen domain gene of human collagen;
  (iv) the neck domain gene of human collectin; and
  (v) the carbohydrate recognition domain gene of human collectin;
(b) transforming a host cell by gene introduction using the vector; and
(c) culturing or breeding the transformant, and collecting proteins having a triple helix structure from these cells or from their culture supernatant.

The following method can be used to examine whether a protein having a triple helix structure is synthesized as a recombinant protein by cells introduced with the above-mentioned vector. Specifically, collagen peptides can be identified by immunochemical methods such as Western blotting by using commercially available antibodies that specifically bind to human collagen. Collagen usually does not migrate according to molecular weight in SDS-polyacrylamide gel electrophoresis (Nature, 227, 680-685 (1970)). Thus, the reactivity of a sample with an anti-collagen antibody can be examined after the sample is electrophoresed simultaneously with collagen as a marker and transferred to a nylon membrane or a nitrocellulose membrane according to the method by Matsudaira et al. (J. Biol. Chem., 261, 10035-10038 (1987)). Further, whether a molecule having a triple-helix structure is present in the recombinant collagen products generated by the expression vector can be examined as follows.

Typical fibrous collagen is a three-chain molecule formed from three subunits (α chains), and has an intramolecular triple-helix structure. Further, collagen having a triple-helix structure is known to be resistant to pepsin digestion. Thus, the presence of three-chain molecules in a protein sample can be confirmed by digesting culture supernatants of cells introduced with the above-mentioned high exogenous gene expression vector with pepsin in an acidic condition, and examining whether the sample has a pepsin-resistant structure.

Specifically, in the present invention, pepsin-treated protein samples were subjected to SDS-polyacrylamide gel electrophoresis under reducing conditions. As a result, the obtained recombinant collagen was shown to have pepsin resistance similar to that of natural collagen, and thus collagen peptides having a pepsin-resistant property were expected to be contained in culture supernatants of cells introduced with the high exogenous gene expression vector. The above-mentioned results show that the expression vector of the present invention has the ability to synthesize in host cells, collagen that has resistance to pepsin, which is a characteristic equivalent to collagen found in the living body.

Methods of producing and purifying the proteins of the present invention having a triple helix structure are shown below, without being limited thereto.

Mammalian cells used for culture as a host cell in the present invention are not particularly limited, but are preferably CHO cells.

Large-scale culture of CHO cells used in the present invention can be done by suspension culture. For example, $1 \times 10^8$ to $1 \times 10^9$ recombinant CHO cells introduced with a human collagen-expression vector containing a weakened neomycin phosphotransferase gene, mouse dihydrofolate reductase gene, and cDNA encoding human collagen or a partial peptide thereof can be cultured in a shaker flask or a spinner flask using 100 ml to 1 L of culture medium. After culturing these cells for an appropriate period of time, proteins can be extracted from the collected culture supernatants in large quantities.

In the culture supernatants of recombinant CHO cells introduced with the human collagen-expression vector containing a weakened neomycin phosphotransferase gene, mouse dihydrofolate reductase gene, and cDNA encoding human collagen or a partial peptide thereof, there exist not only three-chain protein molecules with a triple-helix structure, but also proteins that have not formed into normal three-chain molecules. As mentioned above, collagen-like proteins that do not have a triple-helix structure are digested by pepsin. Thus, collagen-like proteins lacking a triple-helix structure can be removed by pepsin digestion. This treatment can at the same time degrade and remove the proteins in the culture supernatants other than three-chain protein molecules having a triple-helix structure. By using the above-mentioned characteristics, non-collagen proteins as well as proteins lacking a triple-helix structure can be digested and removed by direct pepsin treatment of total proteins present in the culture supernatants of recombinant CHO cells introduced with a human collagen expression vector containing a weakened neomycin phosphotransferase gene, mouse dihydrofolate reductase gene, and cDNA encoding human collagen or a partial peptide thereof.

In the present invention, the human collagen of interest is all human collagens including the type I to XXI collagens that are currently known, and also includes partial peptides thereof. The type of the collagen of the present invention is not particularly limited but includes, as representative examples, type I, type II, type III, type IV, type V, type VII, type IX, type XI, type XII, type XVII, and type XVIII, and preferably type I, type II, type III. Types I, IV, V, IX, and XI consist of two or three types of α chains, and types II, III, VII, XII, XVII, and XVIII consist of one type of α chain. They each have the following molecular composition: type I: [α1(I)]$_2$α2(I), type II: [α1(II)]$_3$, type III: [α1(III)]$_3$, type IV: [α1(IV)]$_2$α2(IV), type V: [α1(V)]$_2$α2(V) and α1(V)α2(V)α3(V), type VII: [α1(VII)]$_3$, type IX: α1(IX)α2(IX)α3(IX), type XI: α1(XI)α2(XI)α3(XI), type XII: [α1(XII)]$_3$, type XVII: [α1(XVII)]$_3$, or type XVIII: [α1(XVIII)]$_3$; however, the molecular composition of the collagen of the present invention is not particularly limited. Further, the molecular composition of the collagen of the present invention is not restricted to that of natural collagen, and may be artificially composed of three different types of α chains.

The nucleotide sequence of a DNA encoding the α1 chain of type I collagen of the present invention is indicated in SEQ ID NO: 10, the nucleotide sequence of a DNA encoding the α2 chain of type I collagen is indicated in SEQ ID NO: 11, the nucleotide sequence of a DNA encoding the α1 chain of type II collagen is indicated in SEQ ID NO: 12, and the nucleotide sequence of a DNA encoding the α1 chain of type III collagen is indicated in SEQ ID NO: 13.

DNAs encoding the collagen of the present invention include oligonucleotides comprising any one of the nucleotide sequences of SEQ ID NOs: 10 to 13, and preferably include oligonucleotides that selectively hybridize to oligonucleotides comprising any one of the nucleotide sequences of SEQ ID NOs: 10 to 13. "Selectively hybridizing" refers to nucleic acid molecules that hybridize with, form double strands with, or bind substantially to a molecule having a predetermined sequence (i.e. a second polypeptide) present in a DNA or RNA sample under hybridization conditions of appropriate stringency. The stringent conditions are, for example, usually conditions of 42° C., 2×SSC, and 0.1% SDS, preferably conditions of 50° C., 2×SSC, and 0.1% SDS, and more preferably conditions of 65° C., 0.1×SSC, and 0.1% SDS, but are not particularly limited to these conditions. Factors affecting hybridization stringency may include plural factors such as temperature and salt concentration, and those skilled in the art can appropriately select these factors to achieve the most appropriate stringency.

The proteins having a triple helix structure produced by the present invention may be procollagen molecules in which a propeptide is linked to the N- and C-termini in the collagen domain, or may be in a form in which the propeptide is removed.

In the present invention, "partial peptides of collagen" refer to polypeptides that are encoded by 20% or more (for example, 20, 30, 40, 50, 60, 70, 80, or 90%) of the polynucleotides of a collagen-encoding cDNA (hereinafter referred to as mini-collagen). The peptides also include those in which the collagen amino acid sequences are partially modified or those that have an added non-collagen amino acid sequence.

In the present invention, "mammalian cells with low collagen expression" refer to cells producing 50 ng/mL of collagen or less when cultured at 1×10$^6$ cells/mL; and preferred examples are CHO cells. In the present invention, "high expression" refers to expression of 1 μg/mL of mini-collagen or more, preferably expression of 5 μg/mL or more of mini-collagen by 5.0×10$^5$ cells/mL gene-introduced CHO cells at 72 hours of culture.

In the present invention, "vectors that can highly express foreign genes" refers to, for example, vectors comprising a marker gene for drug selection in mammalian cells with a weak activity, such that insertion selectively occurs into an actively transcribed region on the chromosome of the mammalian cells. Such vectors preferably include the pNC1 vector (SEQ ID NO: 2), and more preferably include the pDC6/CF vector (SEQ ID NO: 9). Examples of the expression vectors of the present invention include the expression vectors specifically described in the Examples, but are not limited thereto. In the present invention, the culture method may be either suspension or adhesion culture.

All prior art literatures cited in the present specification are incorporated herein by reference.

EXAMPLES

Example 1

Construction of pNC1/Mini-Collagen Type I

Using methods well known to those skilled in the art, pNC1/Mini-Collagen Type I (FIG. 1) was constructed by substituting nucleotide sequence No. 1274 of the pNC1 vector described in SEQ ID NO: 2 with the mini-collagen-encoding cDNA of SEQ ID NO: 3 (hereinafter described as Mini-Collagen Type I).

Example 2

Introduction of pNC1/Mini-Collagen Type I into CHO cells, and G418 Selection Using a CD Medium or a Medium Produced by Adding a Non-animal-based Additive to a CD Medium 10 μg of pNC1/Mini-Collagen Type I was transfected into 5.0×10$^5$ CHO cells (CHO DG44 cells) in 25 cm$^2$-culture flasks using the Lipofectin method (Lipofectamine™ LTX, Invitrogen was used). The transfection method followed the manufacturer's instructions. 48 hours after transfection, the cell number was determined, and then the cells were diluted in an IS CHO-CD w/ Hydrolysate medium (IS Japan) containing 4 mM Gluta MAX™-I (Invitrogen). The cells were plated at concentrations of 1000 cells/well and 100 cells/well into five 96-well microtiter plates each for a total of ten plates (960 wells), and when cultured in the presence of 5% carbon dioxide gas at 37° C. for approximately three weeks, surviving cells were observed (G418-resistant clones). 72 G418-resistant clones were arbitrarily selected from the surviving cells, and subsequently the production levels of mini-collagen in the culture supernatants were determined

Example 3

Determination of the Mini-collagen Production Levels by pNC1/Mini-Collagen Type I-transfected Clones The production level was examined by ELISA. As indicated in FIG. 1, since mini-collagen contains a carbohydrate recognition domain of human MBL at its C terminal portion, human MBL antibodies were used for the detection of mini-collagen. Using 1 μg/mL of an anti-human MBL antibody (gift from Dr. Otani at Asahikawa Medical University, Japan) diluted with a coating buffer (15 mM, $Na_2CO_3$, 35 mM $NaHCO_3$, 0.05% $NaN_3$, pH 9.6), 96-well plates (F96 MAXI SORP Nunc-Immunoplate, Cat. no. 442404, Nunc) were coated at 4° C. for 16 hours. After blocking with 4% Block Ace (Dainippon Sumitomo Pharma Co., Ltd.), 100 μL each of culture supernatants 14 days after transfection (1/10 dilution), two-fold dilution series (20 to 0.3125 ng/mL) of purified human MBL (gift from Dr. Otani at Asahikawa Medical University) in IS CHO-CD w/ Hydrolysate medium (IS Japan) which is a serum-free medium for CHO cells, and IS CHO w/ Hydrolysate medium (IS Japan) were applied, and incubation was carried out at 37° C. for one hour. Furthermore, 0.1 μg/mL of a biotinylated human MBL monoclonal antibody (gift from Dr. Otani at Asahikawa Medical University) was applied at 100 μL/well and this was incubated at 37° C. for one hour. VECTASTAION Elite ABC kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well. After this was reacted at room temperature for 15 minutes, 1 M phosphoric acid was added at 100 μL/well to stop the reaction. Mini-collagen concentration was calculated from the calibration curve of purified human MBL by using a microplate reader (Model 680, manufactured by BioRad) and measuring the absorbance at 450 nm Top ten samples with the highest mini-collagen production levels were determined according to the results obtained by ELISA. The top ten samples were further passaged, transferred to 24-well plates together with IS CHO-CD w/ Hydrolysate medium (IS Japan) containing 4 mM Gluta MAX™-I (Invitrogen), and cells were cultured until they occupied ⅓ or more of each well. 0.4 mL of each line was placed into a sterilized tube, and centrifuged at 200×g for two minutes. The supernatant was discarded, cells were suspended in a fresh medium (IS CHO-CD w/ Hydrolysate medium (IS Japan) containing 4 mM Gluta MAX™-I (Invitrogen)), and the cell count was determined. Then the cell number was adjusted to $5×10^5$ cells/mL by dilution in the medium, 0.2 mL of this was transferred to new 24-well plates, and incubated in the presence of 5% carbon dioxide gas at 37° C. for 72 hours. After centrifugation at 9300×g for two minutes, the supernatant was collected. Subsequently, the production level of mini-collagen in the culture supernatant was determined.

The production level was examined by ELISA. Using 1 μg/mL of an anti-human MBL antibody (gift from Dr. Otani at Asahikawa Medical University, Japan) diluted with a coating buffer (15 mM, $Na_2CO_3$, 35 mM $NaHCO_3$, 0.05% $NaN_3$, pH 9.6), 96-well plates (F96 MAXI SORP Nunc-Immunoplate, Cat. no. 442404, Nunc) were coated at 4° C. for 16 hours. After blocking with 4% Block Ace (Dainippon Sumitomo Pharma Co., Ltd.), 100 μL each of 72-hour culture supernatants (1/1000 dilution), two-fold dilution series (20 to 0.3125 ng/mL) of purified human MBL (gift from Dr. Otani at Asahikawa Medical University) in IS CHO-CD w/Hydrolysate medium (IS Japan) which is a serum-free medium for CHO cells, and IS CHO w/Hydrolysate medium (IS Japan) were applied, and incubation was carried out at 37° C. for one hour. Furthermore, 0.1 μg/mL of a biotinylated human MBL monoclonal antibody (gift from Dr. Otani at Asahikawa Medical University) was applied at 100 μL/well and this was incubated at 37° C. for one hour. VECTASTAION Elite ABC kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well. After this was reacted at room temperature for 15 minutes, 1 M phosphoric acid was added at 100 μL/well to stop the reaction. Mini-collagen concentration was calculated from the calibration curve of purified human MBL by using a microplate reader (Model 680, manufactured by BioRad) and measuring the absorbance at 450 nm. The top ten samples with the highest mini-collagen production levels determined according to the results obtained by ELISA are shown in Table 1.

TABLE 1

| MINI-COLLAGEN PRODUCTION LEVELS OF G418-RESISTANT CLONES | |
|---|---|
| CLONE NAME | PRODUCTION LEVEL (μg/mL) |
| MC 1 | 2.6 |
| MC 10 | 5.2 |
| MC 11 | 1.8 |
| MC 12 | 3.8 |
| MC 13 | 4.5 |
| MC 21 | 6.3 |
| MC 24 | 3.5 |
| MC 34 | 2.9 |
| MC 51 | 0.6 |
| MC 64 | 4.5 |

Example 4

Construction of pDC6/CF_Mini-Collagen Type I

Using methods well known to those skilled in the art, pDC6/CF_Mini-Collagen Type I (FIG. 2) was constructed by substituting nucleotide sequence No. 1059 of the pDC6/CF vector described in SEQ ID NO: 9 with the mini-collagen-encoding cDNA of SEQ ID NO: 3 (hereinafter described as Mini-Collagen Type I).

Example 5

Introduction of pDC6/CF_Mini-Collagen Type I into CHO Cells, and Selection Using a CD Medium or a Medium Produced by Adding a Non-animal-based Additive to a CD medium 10 μg of pNC1/Mini-Collagen Type I was transfected into $5.0×10^5$ CHO cells (CHO DG44 cells) in 25 $cm^2$-culture flasks using the Lipofectin method (Lipofectamine™ LTX, Invitrogen was used). The transfection method followed the manufacturer's instructions. 48 hours after transfection, the cell number was determined, and then the cells were diluted in an IS CHO-CD w/ Hydrolysate medium (IS Japan) containing 4 mM Gluta MAX™-I (Invitrogen). The cells were plated at concentrations of 4000 cells/well and 1000 cells/well into five 96-well microtiter plates each for a total of ten plates (960 wells), and when cultured in the presence of 5% carbon dioxide gas at 37° C. for approximately three weeks, surviving cells were observed (surviving clones). 157 surviving clones were arbitrarily selected from the surviving cells, and subsequently the production levels of mini-collagen in the culture supernatants were determined

Example 6

Figure 2:
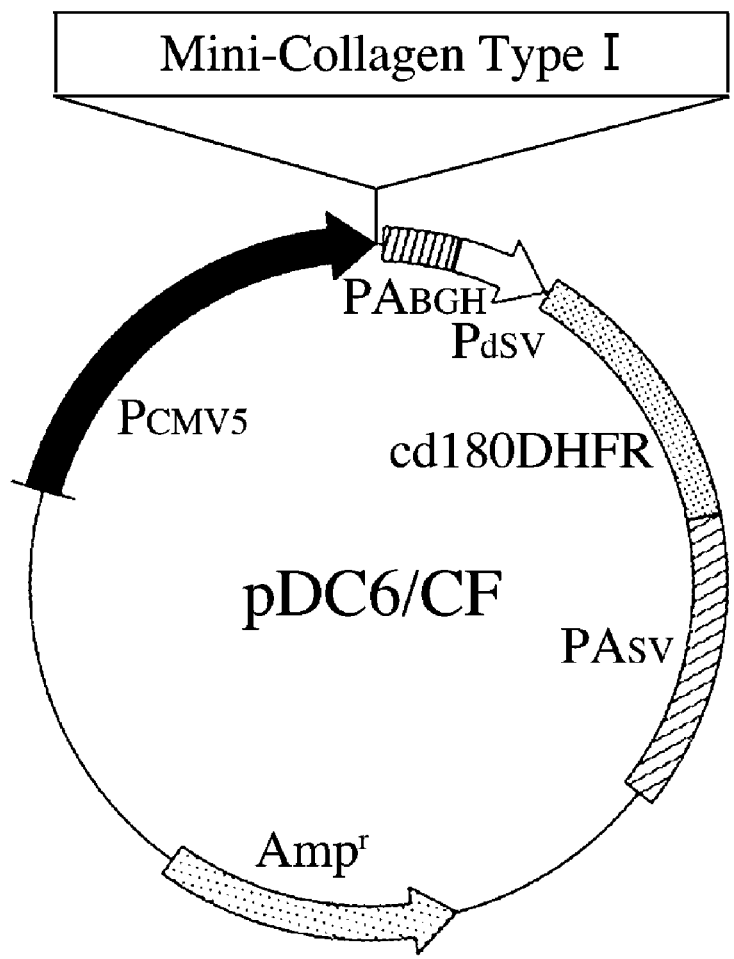
FIG. 2 shows the pDC6/CF_Mini-Collagen Type I construct with the respective abbreviations shown below. PCMV5: cytomegalovirus 5 promoter; Mini-Collagen Type I: mini-collagen DNA; PABGH: bovine growth hormone gene polyA addition signal; PdSV: enhancer-deleted simian virus 40 promoter; cd180DHFR: translation-impaired DHFR gene produced by altering codons in the range of 180 bases from the 5' end of the nucleotide sequence of DHFR to the least frequently used codons in mammals; PASV: simian virus 40 polyA addition signal; and Amp$^r$: selection marker (ampicillin resistance) in E. coli.

Determination of the Mini-Collagen Production Levels by pDC6/CF_Mini-Collagen Type I-transfected Clones The production level was examined by ELISA. As indicated in FIG. 2, since mini-collagen contains the carbohydrate recognition domain of human MBL at its C terminal portion, human MBL antibodies were used for the detection of mini-collagen. Using 1 μg/mL of an anti-human MBL antibody (gift from Dr. Otani at Asahikawa Medical University, Japan) diluted with a coating buffer (15 mM $Na_2CO_3$, 35 mM $NaHCO_3$, 0.05% $NaN_3$, pH 9.6), 96-well plates (F96 MAXI SORP Nunc-Immunoplate, Cat. no. 442404, Nunc) were coated at 4° C. for 16 hours. After blocking with 4% Block Ace (Dainippon Sumitomo Pharma Co., Ltd.), 100 μL each of culture supernatants 14 days after transfection (1/1000 dilution), two-fold dilution series (20 to 0.3125 ng/mL) of purified human MBL (gift from Dr. Otani at Asahikawa Medical University) in IS CHO-CD w/ Hydrolysate medium (IS Japan) which is a serum-free medium for CHO cells, and IS CHO w/ Hydrolysate medium (IS Japan) were applied, and incubation was carried out at 37° C. for one hour. Furthermore, 0.1 μg/mL of a biotinylated human MBL monoclonal antibody (gift from Dr. Otani at Asahikawa Medical University) was applied at 100 μL/well and this was incubated at 37° C. for one hour. VECTASTAION Elite ABC kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well. After this was reacted at room temperature for 15 minutes, 1 M phosphoric acid was added at 100 μL/well to stop the reaction. Mini-collagen concentration was calculated from the calibration curve of purified human MBL by using a microplate reader (Model 680, manufactured by BioRad) and measuring the absorbance at 450 nm Top ten samples with the highest mini-collagen production levels were determined according to the results obtained by ELISA. The top ten samples were further passaged, transferred to 24-well plates together with IS CHO-CD w/ Hydrolysate medium (IS Japan) containing 4 mM Gluta MAX™-I (Invitrogen), and cells were cultured until they occupied ⅓ or more of each well. 0.4 mL of each line was placed into a sterilized tube, and centrifuged at 200×g for two minutes. The supernatant was discarded, cells were suspended in 0.1 mL of fresh medium (IS CHO-CD w/ Hydrolysate medium (IS Japan) containing 4 mM Gluta MAX™-I (Invitrogen)), and the cell count was determined. Then the cell number was adjusted to 5.0×10⁵ cells/mL by dilution in the medium, 0.2 mL of this was transferred to new 24-well plates, and incubated in the presence of 5% carbon dioxide gas at 37° C. for 72 hours. After centrifugation at 9300×g for two minutes, the supernatant was collected. Subsequently, the production level of mini-collagen in the culture supernatant was determined.

The production level was examined by ELISA. Using 1 μg/mL of an anti-human MBL antibody (gift from Dr. Otani at Asahikawa Medical University, Japan) diluted with a coating buffer (15 mM, $Na_2CO_3$, 35 mM $NaHCO_3$, 0.05% $NaN_3$, pH 9.6), 96-well plates (F96 MAXI SORP Nunc-Immunoplate, Cat. no. 442404, Nunc) were coated at 4° C. for 16 hours. After blocking with 4% Block Ace (Dainippon Sumitomo Pharma Co., Ltd.), 100 μL each of 72-hour culture supernatants (1/1000 dilution), two-fold dilution series (20 to 0.3125 ng/mL) of purified human MBL (gift from Dr. Otani at Asahikawa Medical University) in IS CHO-CD w/Hydrolysate medium (IS Japan) which is a serum-free medium for CHO cells, and IS CHO w/Hydrolysate medium (IS Japan) were applied, and incubation was carried out at 37° C. for one hour. Furthermore, 0.1 μg/mL of a biotinylated human MBL monoclonal antibody (gift from Dr. Otani at Asahikawa Medical University) was applied at 100 μL/well and this was incubated at 37° C. for one hour. VECTASTAION Elite ABC kit STANDARD (2 drops of Reagent A, 2 drops of Regent B/5 mL, Vector), which had been incubated at 37° C. for 30 minutes, was applied at 100 μL/well, and this was allowed to react at 37° C. for 45 minutes. PEROXIDASE SUBSTRATE KIT TMB (2 drops of Buffer, 3 drops of TMB, 2 drops of HYDROGEN PEROXIDE/5 mL, Vector), which had been incubated at room temperature for 30 minutes, was further applied at 100 μL/well. After this was reacted at room temperature for 15 minutes, 1 M phosphoric acid was added at 100 μL/well to stop the reaction. Mini-collagen concentration was calculated from the calibration curve of purified human MBL by using a microplate reader (Model 680, manufactured by BioRad) and measuring the absorbance at 450 nm. The top ten samples with the highest mini-collagen production levels determined according to the results obtained by ELISA are shown in Table 2.

TABLE 2

| MINI-COLLAGEN PRODUCTION LEVELS OF CLONES GROWING IN HT-FREE MEDIUM | |
|---|---|
| CLONE NAME | PRODUCTION LEVEL (μg/mL) |
| MC6-22 | 8.6 |
| MC6-33 | 8.5 |
| MC6-35 | 7.1 |
| MC6-55 | 9.7 |
| MC6-57 | 9.9 |
| MC6-97 | 8.6 |
| MC6-116 | 9.9 |
| MC6-126 | 8.4 |
| MC6-137 | 5.6 |
| MC6-145 | 9.5 |

Example 7

Purification of Mini-collagen

Figure 3:
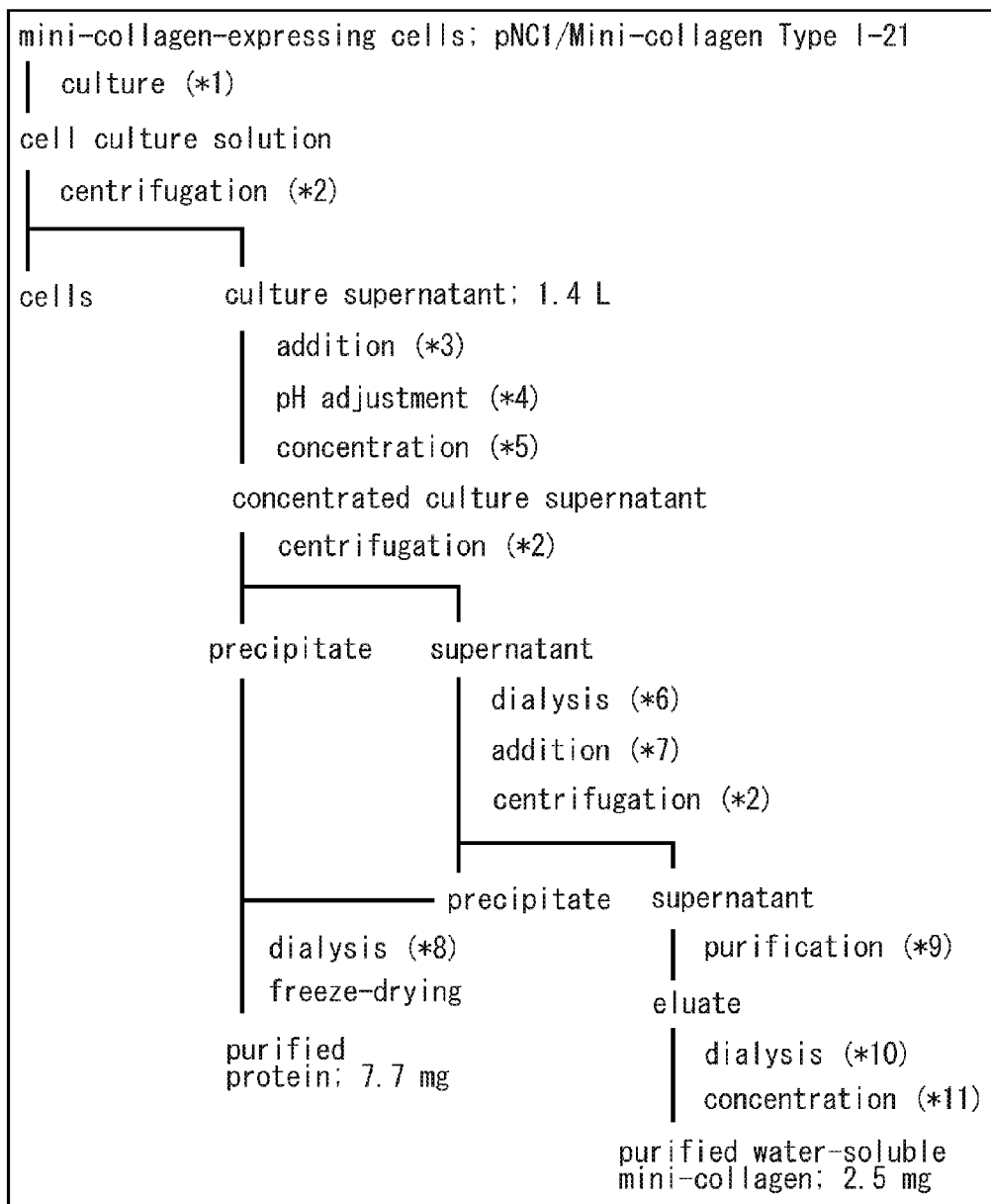
FIG. 3 is a flow chart of mini-collagen purification. All steps were carried out at 4° C. unless specified otherwise. In the figure, *1 indicates the step of adjusting cells to $2.0 \times 10^5$ cells/mL with IS CHO-CD w/ Hydrolysate (IS JAPAN) medium supplemented to have final concentrations of 4 mM Gluta MAX™-I (GIBCO), 0.4 mg G418 Sulfate Cell Culture Tested (CALBIOCHEM), and 1×HT supplement solution (GIBCO), and culturing by stationary culture in T-75 flasks (FALCON) at 37° C. in the presence of 5% carbon dioxide for 14 days (HERA cell 150, Heraeus). *2 indicates the step of centrifuging at 1,750×g for one hour (EX-126, TOMY). *3 indicates the step of adding sodium chloride (Wako) to the supernatant (1.4 L) to obtain 0.4 M. *4 indicates the step of adjusting the pH to 7.4 (F-51, HORIBA) at 4° C. using sodium hydroxide (Wako). *5 indicates the step of concentrating the culture supernatant to 1/20 its volume by using cross flow filtration (VIVAFLOW50; 10,000 MWCO PES; VIVASIENCE). *6 indicates the step of dialyzing (Spectra/Pro™ Biotech Dialysis Membranes; 10,000 MWCO; Spectrum Laboratories, Inc.) for three days against TBS (TBS powder, Takara) containing 5 mM EDTA (Dojindo). *7 indicates the step of adding calcium chloride (Wako) and sodium chloride (Wako) to obtain 20 mM and at 2 M, respectively. *8 indicates the step of dialyzing (Spectra/Pro™ Biotech Cellulose Ester (CE) Dialysis Membranes; 25,000 MWCO; Spectrum Laboratories, Inc.) against MilliQ water (MILLIPORE) for five days. *9 indicates the steps of filling an Econo-Column (Bio-RAD) with 4.5 mL of mannan agarose gel (SIGMA), washing and equilibrating the gel with 45 mL of TBS (TBS powder, Takara) containing 5 mM EDTA (Dojindo) and TBS (TBS powder, Takara) containing 5 mM calcium chloride (Wako), loading the supernatant by circulation at a flow rate of 1.0 mL/min for 17.5 hours, removing the supernatant, then washing with 10 mL of TBS (TBS powder, Takara) containing 5 mM calcium chloride (Wako), and eluting mini-collagen with 20 mL of TBS (TBS powder, Takara) containing 5 mM EDTA (Dojindo). *10 indicates the step of dialyzing (Spectra/Pro™ Biotech Dialysis Membranes; 10,000 MWCO; Spectrum Laboratories, Inc.) against 0.4 M sodium chloride-0.1 M Tris-hydrochloride buffer (pH7.4 at 4° C.) for five days. *11 indicates the step of concentrating to 1/10 the volume by ultrafiltration at 1,750×g for 30 minutes using Amicon Ultra-15 (10,000 MWCO; MILLIPORE).

Mini-collagen-expressing CHO cells (pNC1/Mini-collagen Type I-21) were adjusted to 2.0×10⁵ cells/mL with IS CHO-CD w/ Hydrolysate (IS JAPAN) medium supplemented to have final concentrations of 4 mM Gluta MAX™-I (GIBCO), 0.4 mg G418 Sulfate Cell Culture Tested (CALBIOCHEM), and 1×HT supplement solution (GIBCO), and cultured by stationary culture in T-75 flasks (FALCON) at 37° C. in the presence of 5% carbon dioxide for 14 days (HERA cell 150, Heraeus). The following steps were carried out at 4° C. unless specified otherwise. The culture solutions were collected and centrifuged at 1,750×g for one hour (EX-126, TOMY) to separate the cells and supernatant. To this supernatant (1.4 L), sodium chloride (Wako) was added to obtain 0.4 M and the pH was adjusted (F-51, HORIBA) to 7.4 at 4° C. using sodium hydroxide (Wako), and this was concentrated to 1/20 its volume by using cross flow filtration (VIVAFLOW50; 10,000 MWCO PES; VIVASIENCE). The precipitates formed in this process were collected by centrifugation (EX-126, TOMY) at 1,750×g for one hour. The supernatant was dialyzed for three days (Spectra/Pro™ Biotech Dialysis Membranes; 10,000 MWCO; Spectrum Laboratories, Inc.) against TBS (TBS powder, Takara) containing 5 mM EDTA (Dojindo), and calcium chloride (Wako) and sodium chloride (Wako) were added to obtain 20 mM and 2 M, respectively, to cause precipitation. This was centrifuged at 1,750×g for one hour (EX-126, TOMY) to separate the precipitates and supernatant. These precipitates were combined with the previously collected precipitates, dialyzed (Spectra/Pro™ Biotech Cellulose Ester (CE) Dialysis Membranes; 25,000 MWCO; Spectrum Laboratories, Inc.) against MilliQ water (MILLIPORE) for five days, and freeze dried (Concentrator 5301, Eppendorf) to obtain purified proteins. 1.47 mg of the purified proteins was dissolved in 1.47 mL of 50 mM acetic acid (Wako) solution, and this was used in the following assays. Furthermore, mini-collagen remaining in the supernatant was purified using a mannan agarose column by utilizing the binding with mannan. First, an Econo-Column (BIO-RAD) was filled with 4.5 mL of mannan agarose gel (SIGMA), the gel was washed and equilibrated with 45 mL of TBS (TBS powder, Takara) containing 5 mM EDTA (Dojindo) and TBS (TBS powder, Takara) containing 5 mM calcium chloride (Wako), and the supernatant was loaded by circulation at a flow rate of 1.0 mL/min for 17.5 hours. Removal of the supernatant was followed by washing with 10 mL of TBS (TBS powder, Takara) containing 5 mM calcium chloride (Wako) and eluting the mini-collagen with 20 mL of TBS (TBS powder, Takara) containing 5 mM EDTA (Dojindo). The eluate was dialyzed (Spectra/Pro™ Biotech Dialysis Membranes; 10,000 MWCO; Spectrum Laboratories, Inc.) against 0.4 M sodium chloride-0.1 M Tris-hydrochloride buffer (pH7.4 at 4° C.) for five days. Thereafter, the volume was concentrated to 1/10 by ultrafiltration at 1,750×g for 30 minutes using Amicon Ultra-15 (10,000 MWCO; MILLIPORE). Ultimately, 7.7 mg of fibrous mini-collagen was collected as precipitate from 1.4 L of the culture supernatant, and subsequently, 2.5 mg of water-soluble mini-collagen having the activity of binding to mannan was collected from the remaining supernatant (see FIG. 3).

Example 8

Analysis of Mini-collagen

Proteins purified from the culture supernatant and water-soluble mini-collagen were analyzed by SDS polyacrylamide gel electrophoresis under reducing conditions.

Figure 4:
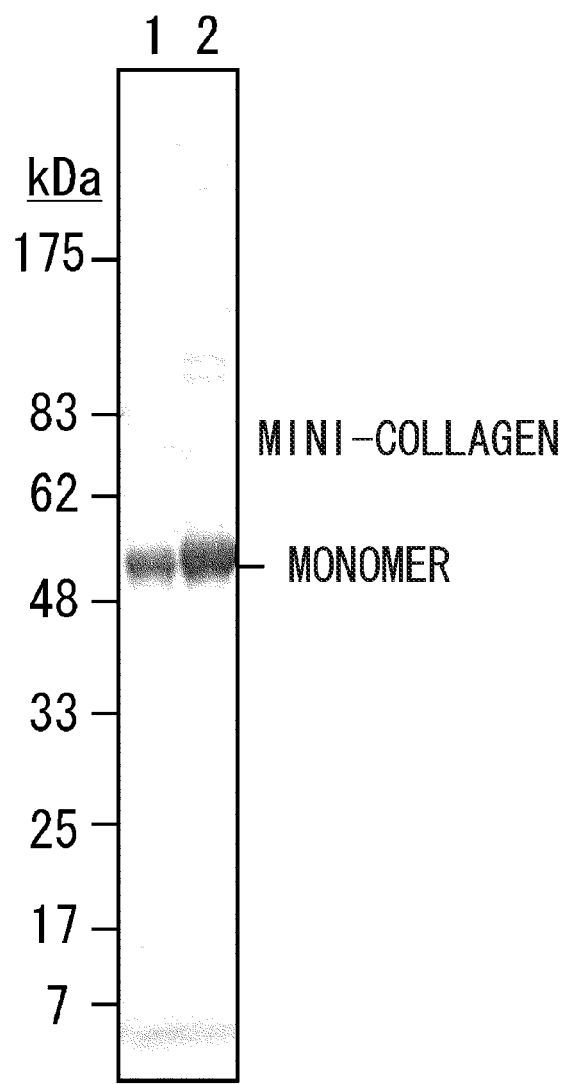
FIG. 4 shows in a photograph the analysis result of SDS polyacrylamide gel electrophoresis under reducing conditions (2-mercaptoethanol added) of proteins purified from the culture supernatant and water-soluble mini-collagen. Lane 1 shows proteins purified as a precipitate and lane 2 is water-soluble mini-collagen purified on a mannan agarose column. The molecular weight and the mini-collagen oligomer are indicated on the photograph.

More specifically, 10 μL of Laemmli Sample Buffer (BIO-RAD) containing 5% 2-mercaptoethanol (Wako) was added to 10 μL each of the purified proteins and water-soluble mini-collagen (each diluted ten times with TBS (TBS powder, Takara) containing 20 mM calcium chloride (Wako)) for reduction by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 5% to 20% 17 well (Wako) were placed in an electrophoresis vessel (DPE-1020, DAIICHI PURE CHEMICALS CO., LTD), 10 μL of heat-treated sample solutions were applied to Super Sep™ 5% to 20% 17 well (Wako), and electrophoresis was carried out at 40 mA (My Run, COSMO BIO CO., LTD) for 50 minutes. Thereafter, the gel was washed with 25 mL of DW (MILLIPORE) while shaking for five minutes, and this was repeated three times. The gel was stained in 25 mL of Quick-CBB PLUS (Wako) for one hour, and then destained in 25 mL of DW (MILLIPORE) for one hour (see FIG. 4).

Example 9

Analysis of Mini-collagen

Proteins purified from the culture supernatant and water-soluble mini-collagen were analyzed by SDS polyacrylamide gel electrophoresis under non-reducing conditions.

Figure 5:
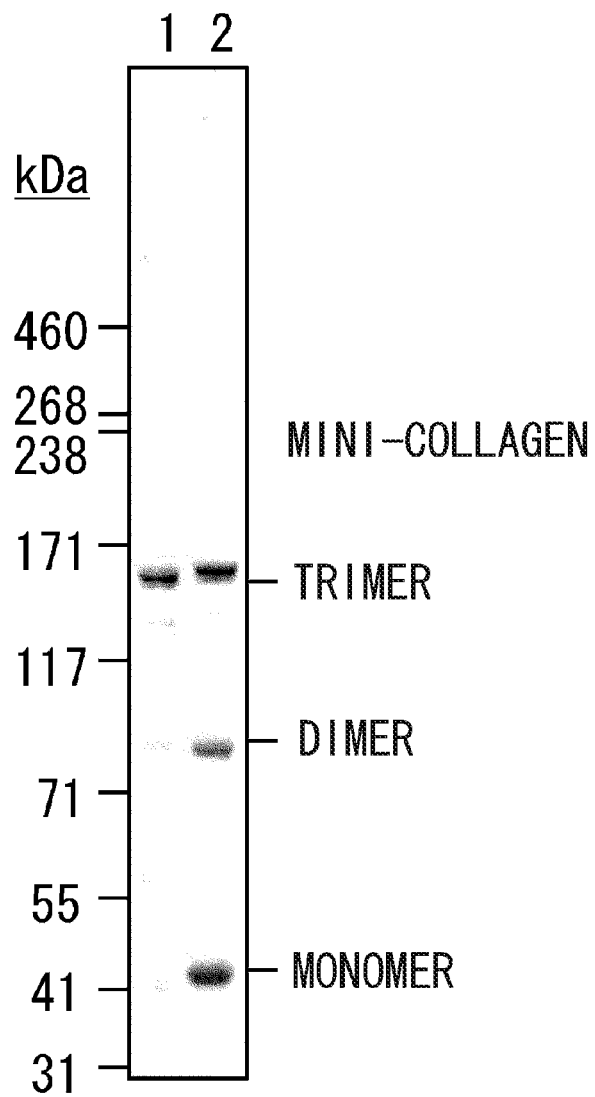
FIG. 5 shows in a photograph the analysis result of SDS polyacrylamide gel electrophoresis under non-reducing conditions (no 2-mercaptoethanol added) of proteins purified from the culture supernatant and water-soluble mini-collagen. Lane 1 shows proteins purified as a precipitate and lane 2 is water-soluble mini-collagen purified on a mannan agarose column The molecular weight and the mini-collagen oligomers are indicated on the photograph.

More specifically, 10 μL of Laemmli Sample Buffer (BIO-RAD) not containing 2-mercaptoethanol was added to 10 μL each of the purified proteins and water-soluble mini-collagen (each diluted ten times with TBS (TBS powder, Takara) containing 20 mM calcium chloride (Wako)), and this was treated by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 3% to 10% 17 well (Wako) were placed in an electrophoresis vessel (DPE-1020, DAIICHI PURE CHEMICALS CO., LTD), and 10 μL of the heat-treated sample solutions were applied to Super Sep™ 3% to 10% 17 well (Wako), and electrophoresis was carried out at 40 mA (My Run, COSMO BIO CO., LTD) for 50 minutes. Then, the gel was washed with 25 mL of DW (MILLIPORE) while shaking (ROTO-SHAKE GENIE, Scientific Industries) for five minutes, and this was repeated three times. The gel was stained in 25 mL of Quick-CBB PLUS (Wako) for one hour, and then destained in 25 mL of DW (MILLIPORE) for one hour (see FIG. 5).

Example 10

Analysis of Mini-collagen

Proteins purified from the culture supernatant and water-soluble mini-collagen were analyzed by native polyacrylamide gel electrophoresis.

Figure 6:
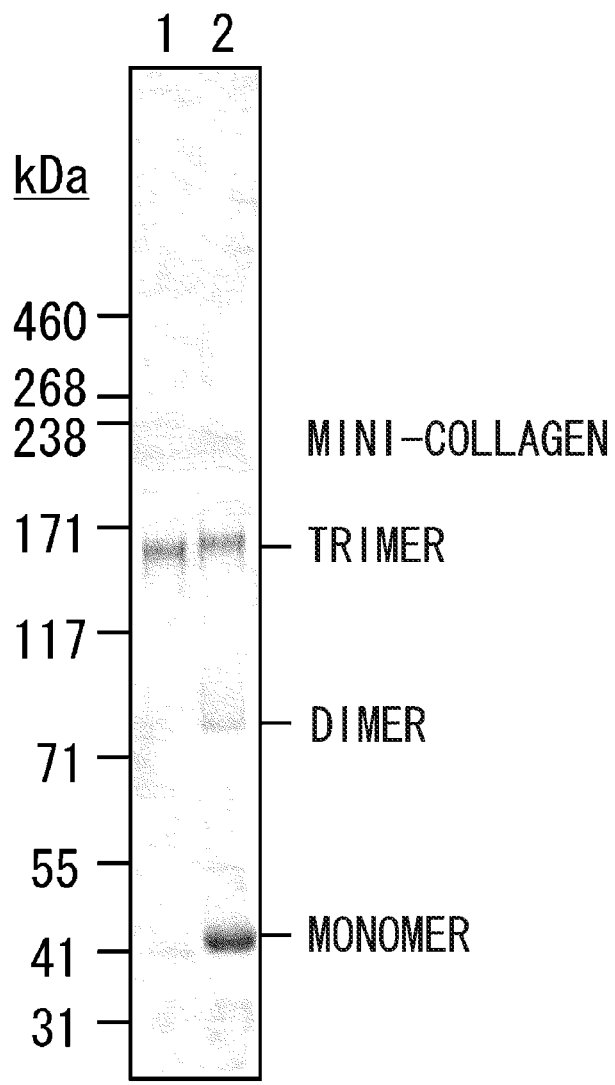
FIG. 6 shows in a photograph the analysis result of polyacrylamide gel electrophoresis under native conditions (no 2-mercaptoethanol and SDS added) of proteins purified from the culture supernatant and water-soluble mini-collagen. Lane 1 shows proteins purified as a precipitate and lane 2 is water-soluble mini-collagen purified on a mannan agarose column The molecular weight and the mini-collagen oligomers are indicated on the photograph.

More specifically, 10 μL of Native Sample Buffer (BIO-RAD) containing neither 2-mercaptoethanol nor SDS was added to 10 μL each of the purified proteins and water-soluble mini-collagen (each diluted ten times with TBS (TBS powder, Takara) containing 20 mM calcium chloride (Wako)). An electrophoresis buffer (Tris/Glycine/SDS, BIO-RAD) and Super Sep™ 3% to 10% 17 well (Wako) were placed in an electrophoresis vessel (DPE-1020, DAIICHI PURE CHEMICALS CO., LTD), 10 μL of the prepared sample solutions were applied to Super Sep™ 3% to 10% 17 well (Wako), and electrophoresis was carried out at 40 mA (My Run, COSMO BIO CO., LTD) for 50 minutes. Then, the gel was washed with 25 mL of DW (MILLIPORE) while shaking (ROTO-SHAKE GENIE, Scientific Industries) for five minutes, and this was repeated three times. The gel was stained in 25 mL of Quick-CBB PLUS (Wako) for one hour, and then destained in 25 mL of DW (MILLIPORE) for one hour (see FIG. 6).

Example 11

Western Blotting Under Reducing Conditions

Since the mini-collagen encodes the carbohydrate recognition domain (CRD) of MBL, the CRD domain is included in the expressed mini-collagen. Therefore, anti-MBL (CRD domain-recognizing) antibodies can bind thereto. This was utilized to perform Western blotting under reducing conditions using a rabbit anti-MBL (CRD domain) polyclonal antibody (gift from Dr. Otani at Asahikawa Medical University), and the purified proteins and water-soluble mini-collagen were identified by chemiluminescence detection.

Figure 7:
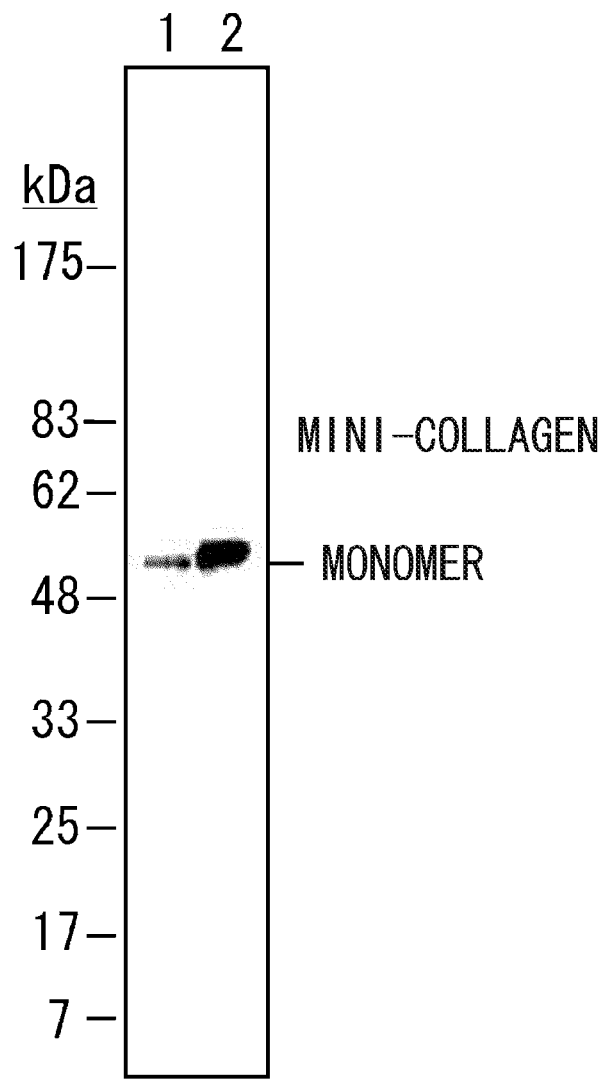
FIG. 7 shows in a photograph results obtained by performing SDS polyacrylamide gel electrophoresis under reducing conditions (2-mercaptoethanol added) of proteins purified from the culture supernatant and water-soluble mini-collagen, performing Western blotting using a rabbit anti-MBL (carbohydrate recognition domain (CRD)) polyclonal antibody, and reversing the contrast of the photograph of chemiluminescence detection. Lane 1 shows proteins purified as a precipitate and lane 2 is water-soluble mini-collagen purified on a mannan agarose column The molecular weight and the mini-collagen oligomer are indicated on the photograph.

More specifically, 10 μL of Laemmli Sample Buffer (BIO-RAD) containing 5% of 2-mercaptoethanol (Wako) was mixed into 10 μL each of the purified proteins and water-soluble mini-collagen (each diluted 500 times with TBS (TBS powder, Takara) containing 20 mM calcium chloride (Wako)) for reduction by heating at 98° C. for five minutes (TaKaRa PCR Thermal Cycler PERSONAL, TaKaRa BIO-MEDICALS). An electrophoresis buffer (Tris/Glycine/SDS, BIO-RAD) and Super Sep™ 5% to 20% 17 well (Wako) were placed in an electrophoresis vessel (DPE-1020, DAIICHI PURE CHEMICALS CO., LTD), and 10 μL of the heat-treated sample solutions were applied to Super Sep™ 5% to 20% 17 well (Wako), and electrophoresis was carried out at 40 mA (My Run, COSMO BIO CO., LTD) for 50 minutes. Then, the gel was removed from the glass plates, and soaked for five minutes while shaking (ROTO-SHAKE GENIE, Scientific Industries) in a transfer buffer (Tris/Glycine Buffer (BIO-RAD) containing 30% methanol (Wako)). Immobilon-P Transfer Membrane (MILLIPORE) was soaked while shaking (ROTO-SHAKE GENIE, Scientific Industries) in 8 mL of methanol (Wako) for 15 seconds, 8 mL of MilliQ water (MILLIPORE) for two minutes, and 8 mL of transfer buffer (Tris/Glycine Buffer (BIO-RAD) containing 30% methanol (Wako)) for five minutes. In a transfer apparatus (TRANS-BLO, SD SEMI-DRY TRANSFER CELL, BIO-RAD), transfer buffer (Tris/Glycine Buffer (BIO-RAD) containing 30% methanol (Wako))-soaked filter papers (Extra Thick Blot Paper Criterion™ Size, BIO-RAD), Immobilon-P Transfer Membrane (MILLIPORE), gel, and filter papers (Extra Thick Blot Paper Criterion™ Size, BIO-RAD) were laid in order from the minus side, a cover was placed, and electrophoresis was carried out at 80 mA (PowerPac HC™, BIO-RAD) for two hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours, then washed three times by shaking for five minutes in 8 mL of TBS (TBS powder, Takara) containing 0.05% Tween 20 (Polyoxyethylene (20) Sorbitan Monolaurate, Wako). 8 mL of rabbit anti-MBL (CRD domain) polyclonal antibody (gift from Dr. Otani at Asahikawa Medical University) diluted 2,000 times with TBS (TBS powder, Takara) containing 0.05% Tween 20 (Polyoxyethylene (20) Sorbitan Monolaurate, Wako) and the proteins on the membrane were reacted for one hour at room temperature while shaking (ROTO-SHAKE GENIE, Scientific Industries). After the unbound antibodies were removed, the membrane was washed three times by shaking for five minutes in 8 mL of TBS (TBS powder, Takara) containing 0.05% Tween 20 (Polyoxyethylene (20) Sorbitan Monolaurate, Wako). 8 mL of a peroxidase-conjugated AffiniPure F(ab')$_2$ Fragment Donkey Anti-Rabbit IgG(H+L) (Jackson ImmunoResearch) diluted 20,000 times in TBS (TBS powder, Takara) containing 0.05% Tween 20 (Polyoxyethylene (20) Sorbitan Monolaurate, Wako) was added, and reaction was allowed to take place at room temperature for one hour while shaking (ROTO-SHAKE GENIE, Scientific Industries). After the unbound antibodies were removed, the membrane was washed three times by shaking for ten minutes in 24 mL of TBS (TBS powder, Takara) containing 0.05% Tween 20 (Polyoxyethylene (20) Sorbitan Monolaurate, Wako). 1 mL of Immobilon™ Western Chemiluminescent HRP Substrate (MILLIPORE) was added for chemiluminescence, and a one-minute photograph was taken using Light-Capture ATTO Cooled CCD Camera System (ATTO) at its normal settings (see FIG. 7).

Example 12

Western Blotting Under Non-reducing Conditions

Since the mini-collagen encodes the carbohydrate recognition domain (CRD) of MBL, the CRD domain is included in the expressed mini-collagen. Therefore, anti-MBL (CRD domain-recognizing) antibodies can bind thereto. This was utilized to perform Western blotting under non-reducing conditions using a rabbit anti-MBL (CRD domain) polyclonal antibody (gift from Dr. Otani at Asahikawa Medical University), and the purified proteins and water-soluble mini-collagen were identified by chemiluminescence detection.

Figure 8:
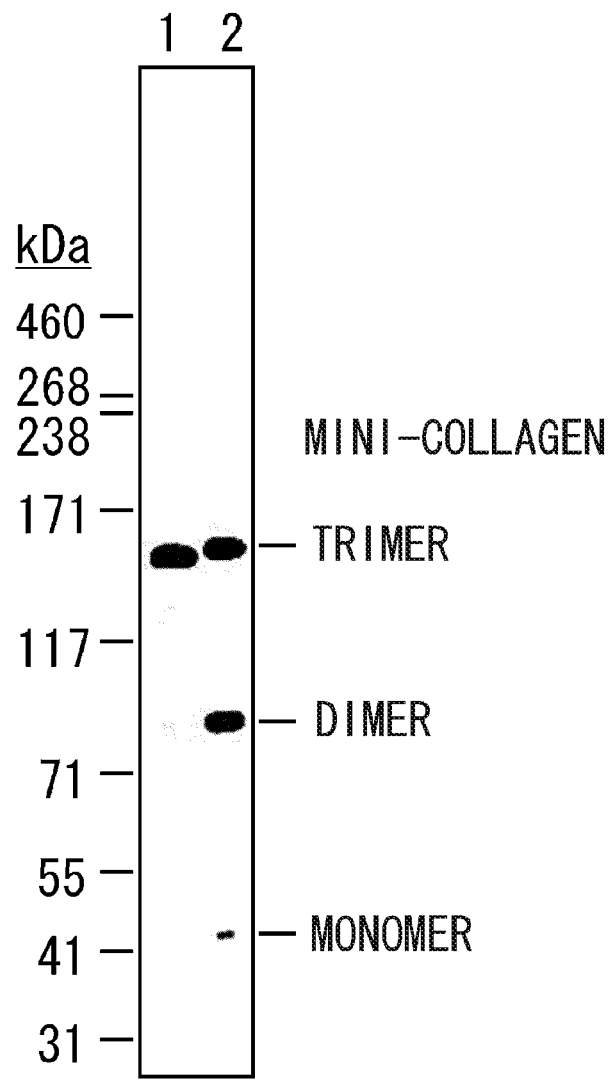
FIG. 8 shows in a photograph the result obtained by performing SDS polyacrylamide gel electrophoresis under non-reducing conditions (no 2-mercaptoethanol added) of proteins purified from the culture supernatant and water-soluble mini-collagen, performing Western blotting using a rabbit anti-MBL (carbohydrate recognition domain (CRD)) polyclonal antibody, and then reversing the contrast of the photograph of chemiluminescence detection. Lane 1 shows proteins purified as a precipitate and lane 2 is water-soluble mini-collagen purified on a mannan agarose column. The molecular weight and the mini-collagen oligomers are indicated on the photograph.

More specifically, 10 μL of Laemmli Sample Buffer (BIO-RAD) not containing 5% of 2-mercaptoethanol was mixed into 10 μL each of the purified proteins and water-soluble mini-collagen (each diluted 500 times with TBS (TBS powder, Takara) containing 20 mM calcium chloride (Wako)) and treated by heating at 98° C. for five minutes (TaKaRa PCR Thermal Cycler PERSONAL, TaKaRa BIOMEDICALS). An electrophoresis buffer (Tris/Glycine/SDS, BIO-RAD) and Super Sep™ 3% to 10% 17 well (Wako) were placed in an electrophoresis vessel (DPE-1020, DAIICHI PURE CHEMICALS CO., LTD), and 10 μL of the heat-treated sample solutions were applied to Super Sep™ 3% to 10% 17 well (Wako), and electrophoresis was carried out at 40 mA (My Run, COSMO BIO CO., LTD) for 50 minutes. Thereafter, the gel was removed from the glass plates, and soaked for five minutes while shaking (ROTO-SHAKE GENIE, Scientific Industries) in a transfer buffer (Tris/Glycine Buffer (BIO-RAD) containing 30% methanol (Wako)). Immobilon-P Transfer Membrane (MILLIPORE) was soaked while shaking (ROTO-SHAKE GENIE, Scientific Industries) in 8 mL of methanol (Wako) for 15 seconds, 8 mL of MilliQ water (MILLIPORE) for two minutes, and 8 mL of transfer buffer (Tris/Glycine Buffer (BIO-RAD) containing 30% methanol (Wako)) for five minutes. In a transfer apparatus (TRANS-BLO SD SEMI-DRY TRANSFER CELL, BIO-RAD), transfer buffer (Tris/Glycine Buffer (BIO-RAD) containing 30% methanol (Wako))-soaked filter papers (Extra Thick Blot Paper Criterion™ Size, BIO-RAD), Immobilon-P Transfer Membrane (MILLIPORE), gel, and filter papers (Extra Thick Blot Paper Criterion™ Size, BIO-RAD) were laid in order from the minus side, a cover was placed, and electrophoresis was carried out at 80 mA (PowerPac HC™, BIO-RAD) for two hours to transfer the separated proteins onto the Immobilon-P Transfer Membrane (MILLIPORE). After transfer, the Immobilon-P Transfer Membrane (MILLIPORE) was soaked in 8 mL of ImmunoBlock (registered trademark, Laboratory Products division of Dainippon Sumitomo Pharma Co., Ltd.) and blocked at 4° C. for 18 hours, then washed three times by shaking for five minutes in 8 mL of TBS (TBS powder, Takara) containing 0.05% Tween 20 (Polyoxyethylene (20) Sorbitan Monolaurate, Wako). 8 mL of a rabbit anti-MBL (CRD domain) polyclonal antibody (gift from Dr. Otani at Asahikawa Medical University) diluted 2,000 times with TBS (TBS powder, Takara) containing 0.05% Tween 20 (Polyoxyethylene (20) Sorbitan Monolaurate, Wako) and the proteins on the membrane were reacted for one hour at room temperature while shaking (ROTO-SHAKE GENIE, Scientific Industries). After the unbound antibodies, the membrane was washed three times by shaking for five minutes in 8 mL of TBS (TBS powder, Takara) containing 0.05% Tween 20 (Polyoxyethylene (20) Sorbitan Monolaurate, Wako). 8 mL of a peroxidase-conjugated AffiniPure F(ab')$_2$ Fragment Donkey Anti-Rabbit IgG(H+L) (Jackson ImmunoResearch) diluted 20,000 times in TBS (TBS powder, Takara) containing 0.05% Tween 20 (Polyoxyethylene (20) Sorbitan Monolaurate, Wako) was added, and reaction was allowed to take place at room temperature for one hour while shaking (ROTO-SHAKE GENIE, Scientific Industries). After the unbound antibodies were removed, the membrane was washed three times by shaking for ten minutes in 24 mL of TBS (TBS powder, Takara) containing 0.05% Tween 20 (Polyoxyethylene (20) Sorbitan Monolaurate, Wako). 1 mL of Immobilon™ Western Chemiluminescent HRP Substrate (MILLIPORE) was added for chemiluminescence, and a one-minute photograph was taken using LightCapture ATTO Cooled CCD Camera System (ATTO) at its normal settings (see FIG. 8).

Example 13

Pepsin Digestion of the Proteins Purified from the Culture Supernatant and Naturally-occurring Human Atelocollagen Type I The purified proteins and naturally-occurring human atelocollagen type I (Collagen, Type I, Acid Soluble, From Human Skin, SIGMA-ALDRICH) were digested with pepsin under acidic conditions, and resistance against cleavage by pepsin was verified from SDS polyacrylamide electrophoresis images.

Figure 9:
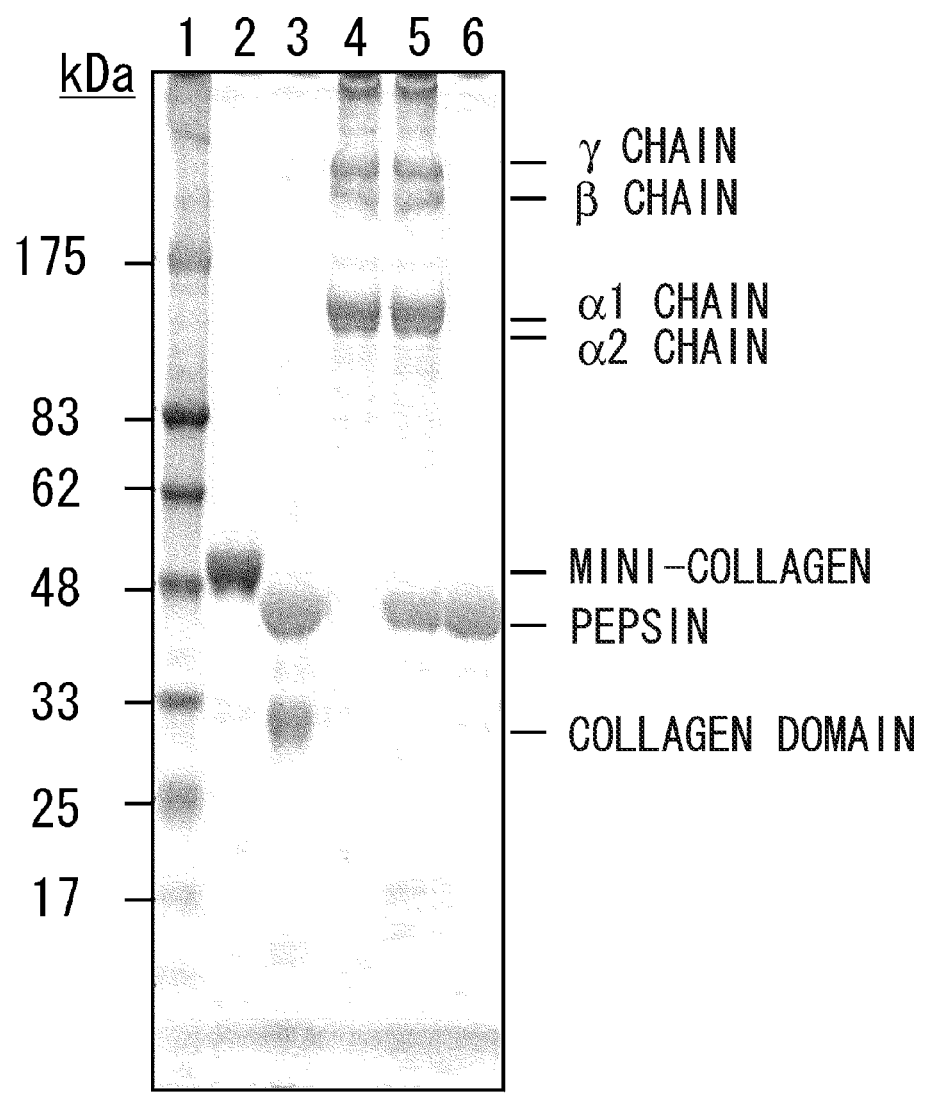
FIG. 9 shows in a photograph the analysis result of SDS polyacrylamide gel electrophoresis under reducing conditions (2-mercaptoethanol added) of the purified protein and naturally-occurring human atelocollagen type I digested with pepsin under acidic conditions. Positions of the bands for mini-collagen, the collagen domain of mini-collagen remaining after digestion, and pepsin are indicated on the photograph. Lane 1: molecular weight marker; lane 2: purified protein not digested with pepsin; lane 3: purified protein digested with pepsin; lane 4: naturally-occurring human atelocollagen type I not digested with pepsin; lane 5: naturally-occurring human atelocollagen type I digested with pepsin; and lane 6: pepsin alone added.

More specifically, 3 µL of 0.3 M hydrochloric acid solution was added to 10 µL each of the purified proteins (0.5 mg/mL) or naturally-occurring human atelocollagen type I (Collagen, Type I, Acid Soluble, From Human Skin, SIGMA-ALDRICH) (1 mg/mL) to adjust the pH to 2, 5 µL of 2 mg/mL pepsin (Pepsin, From Porcine Stomach Mucosa, 3370 units/mg protein; SIGMA-ALDRICH) solution were added respectively, and pepsin digestion was carried out at 20° C. (TaKaRa PCR Thermal Cycler PERSONAL; TaKaRa BIOMEDICALS) for two hours. Here, samples that did not have pepsin added to the purified proteins and such, and samples that had only pepsin (Pepsin, From Porcine Stomach Mucosa, 3370 units/mg protein; SIGMA-ALDRICH) but no addition of the purified proteins and such were prepared as controls, 5 µL of α10 mM acetic acid solution was added instead of the pepsin solution and 10 µL of α10 mM acetic acid solution was added instead of the purified proteins and such, and incubation was carried out at 20° C. for two hours. 1 µL of 1 M Tris (2-Amino-2-hydroxymethyl-1,3-propanediol (Tris aminomethane); Wako) solution was added to the purified protein samples and the samples of pepsin alone (Pepsin, From Porcine Stomach Mucosa, 3370 units/mg protein; SIGMA-ALDRICH), and 5 µL of this solution was added to naturally-occurring human atelocollagen (Collagen, Type I, Acid Soluble, From Human Skin, SIGMA-ALDRICH) to stop the reaction, and then collagen was refibrillized irreversibly by incubation at 4° C. for 18 hours. Laemmli Sample Buffer (BIO-RAD) containing 5% of 2-mercaptoethanol (Wako) was added at an amount of 19 µL to the purified protein samples and the samples of pepsin alone, and 23 µL to naturally-occurring human atelocollagen type I (Collagen, Type I, Acid Soluble, From Human Skin, SIGMA-ALDRICH) for reduction by heating (TaKaRa PCR Thermal Cycler PERSONAL; TaKaRa BIOMEDICALS) at 98° C. for five minutes. An electrophoresis buffer (Tris/Glycine/SDS, BIO-RAD) and Super Sep™ 5% to 20% 17 well (Wako) were placed in an electrophoresis vessel (DPE-1020, DAIICHI PURE CHEMICALS CO., LTD), 10 µL of the heat-treated sample solutions were applied to Super Sep™ 5% to 20% 17 well (Wako), and electrophoresis was carried out at 40 mA (My Run, COSMO BIO CO., LTD) for 50 minutes. Then, the gel was washed in 25 mL of DW (MILLIPORE) while shaking for five minutes (ROTO-SHAKE GENIE, Scientific Industries), and this was repeated three times. The gel was stained for one hour in 25 mL of Quick-CBB PLUS (Wako), and then destained in 25 mL of DW (MILLIPORE) for one hour (see FIG. 9). As a result, naturally-occurring human atelocollagen type I (Collagen, Type I, Acid Soluble, From Human Skin, SIGMA-ALDRICH) was not cleaved by pepsin digestion. A band was observed at 50 kDa for mini-collagen, and since the non-collagen domains were cleaved and eliminated by pepsin digestion, a band was observed at 30 kDa for the collagen domain alone. This showed that in a similar manner to naturally-occurring human atelocollagen type I (Collagen, Type I, Acid Soluble, From Human Skin, SIGMA-ALDRICH), mini-collagen is resistant against cleavage by pepsin (Pepsin, From Porcine Stomach Mucosa, 3370 units/mg protein; SIGMA-ALDRICH) and is correctly folded into a triple helix structure.

Example 14

Thermal Stability Assay of the Proteins Purified from the Culture Supernatant

Figure 10:
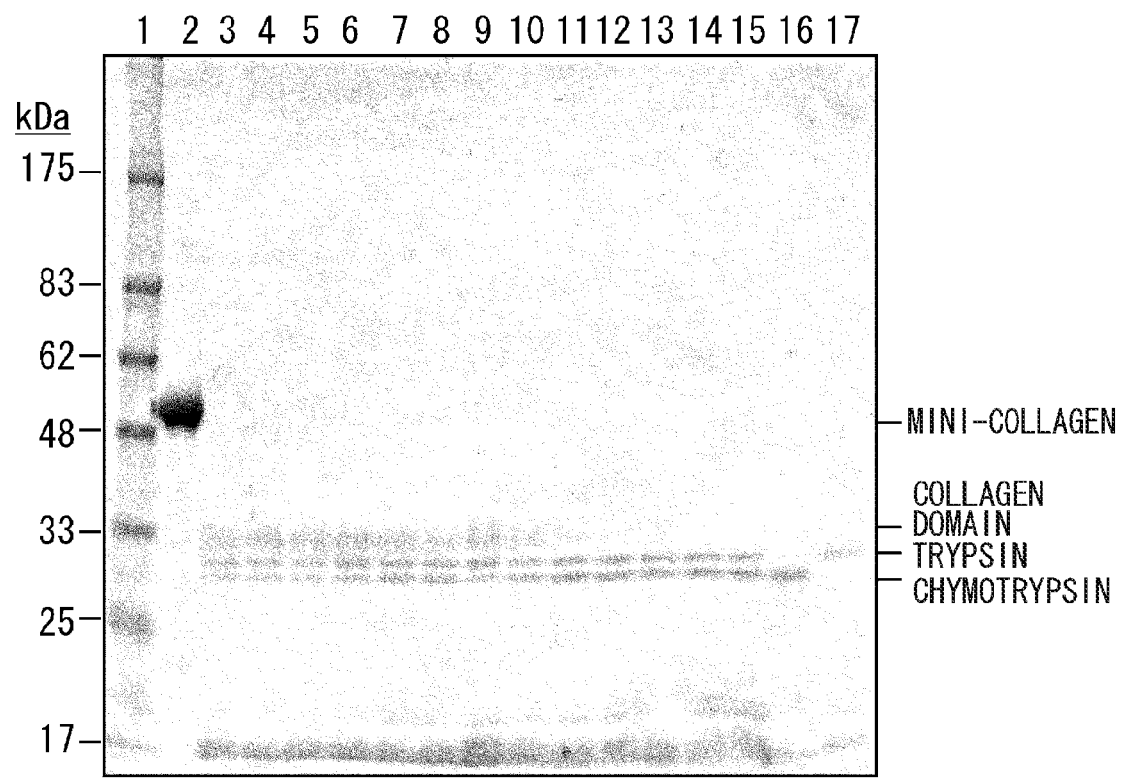
FIG. 10 shows in a photograph the results of analyzing thermal stability by subjecting the purified proteins to heat treatment in a temperature range of 30° C. to 50° C., performing enzyme treatment using a combination of highly concentrated trypsin and chymotrypsin under conditions in which collagen is not digested, and performing SDS polyacrylamide gel electrophoresis under reducing conditions (2-mercaptoethanol added). Positions of the bands for mini-collagen, the collagen domain of mini-collagen remaining after digestion, trypsin, and chymotrypsin are indicated on the photograph. Lane 1 is the molecular weight marker, lane 2 is the purified protein not subjected to enzyme treatment, lanes 3 to 15 are the purified proteins subjected to heat treatment in a temperature range of 30° C. to 50° C., then subjected to trypsin and chymotrypsin enzyme treatments, lane 16 is trypsin alone, and lane 17 is chymotrypsin alone.

Stable collagen correctly folded into a triple helix structure is resistant against cleavage by proteases such as trypsin and chymotrypsin. In this Example, the thermal stability of the purified proteins was assayed by utilizing enzyme treatment with high concentrations of trypsin (Trypsin, Type IX-S, From Porcine Pancreas, 13100 units/mg solid, protein; SIGMA-ALDRICH) and chymotrypsin (α-Chymotrypsin, Type I-S: From Bovine Pancreas, 58 units/mg protein; SIGMA) under conditions in which only collagen is resistant to cleavage. More specifically, 1 µL of 1 M Tris (2-Amino-2-hydroxymethyl-1,3-propanediol (Tris aminomethane); Wako) solution was added to 10 µL of the purified proteins (0.5 mg/mL) to adjust the pH to 7. Samples were heat treated (TaKaRa PCR Thermal Cycler PERSONAL; TaKaRa BIOMEDICALS) for ten minutes at each of the temperatures of 30° C., 35° C., 36° C., 37° C., 38° C., 39° C., 40° C., 41° C., 42° C., 43° C., 44° C., 45° C., and 50° C., then immediately cooled to 20° C. (TaKaRa PCR Thermal Cycler PERSONAL; TaKaRa BIOMEDICALS), 1 µL each of 1 mg/mL of trypsin (Trypsin, Type IX-S, From Porcine Pancreas, 13100 units/mg solid, protein; SIGMA-ALDRICH) and chymotrypsin (α-Chymotrypsin, Type I-S: From Bovine Pancreas, 58 units/mg protein; SIGMA) was added, and enzyme treatment was carried out at 20° C. (TaKaRa PCR Thermal Cycler PERSONAL; TaKaRa BIOMEDICALS) for two minutes. Here, samples that did not have enzyme addition and samples that had trypsin (Trypsin, Type IX-S, From Porcine Pancreas, 13100 units/mg solid protein; SIGMA-ALDRICH) or chymotrypsin (α-Chymotrypsin, Type I-S: From Bovine Pancreas, 58 units/mg protein; SIGMA) alone were prepared, 2 µL of 0.4 M sodium chloride-0.1 M Tris hydrochloride buffer (pH7.4 at 4° C.) was added instead of the enzyme and 12 µL of 0.4 M sodium chloride-0.1 M Tris hydrochloride buffer (pH7.4 at 4° C.) was added instead of the purified proteins and such, and incubation was carried out at 20° C. (TaKaRa PCR Thermal Cycler PERSONAL; TaKaRa BIOMEDICALS) for two minutes. To each sample solution, 13 µL of Laemmli Sample Buffer (BIO-RAD) containing 5% of 2-mercaptoethanol (Wako) was added for reduction by heating (TaKaRa PCR Thermal Cycler PERSONAL; TaKaRa BIOMEDICALS) at 98° C. for five minutes. An electrophoresis buffer (Tris/Glycine/SDS, BIO-RAD) and Super Sep™ 10% to 20% 17 well (Wako) were placed in an electrophoresis vessel (DPE-1020, DAIICHI PURE CHEMICALS CO., LTD), and 6.5 µL of the heat-treated sample solutions were applied to Super Sep™ 10% to 20% 17 well (Wako), and electrophoresis was carried out at 40 mA (My Run, COSMO BIO CO., LTD) for 60 minutes. Then, the gel was washed in 25 mL of DW (MILLIPORE) while shaking (ROTO-SHAKE GENIE, Scientific Industries) for five minutes, and this was repeated three times. The gel was stained for one hour in 25 mL of Quick-CBB PLUS (Wako), and then destained in 25 mL of DW (MILLIPORE) for one hour (see FIG. 10).

Figure 11:
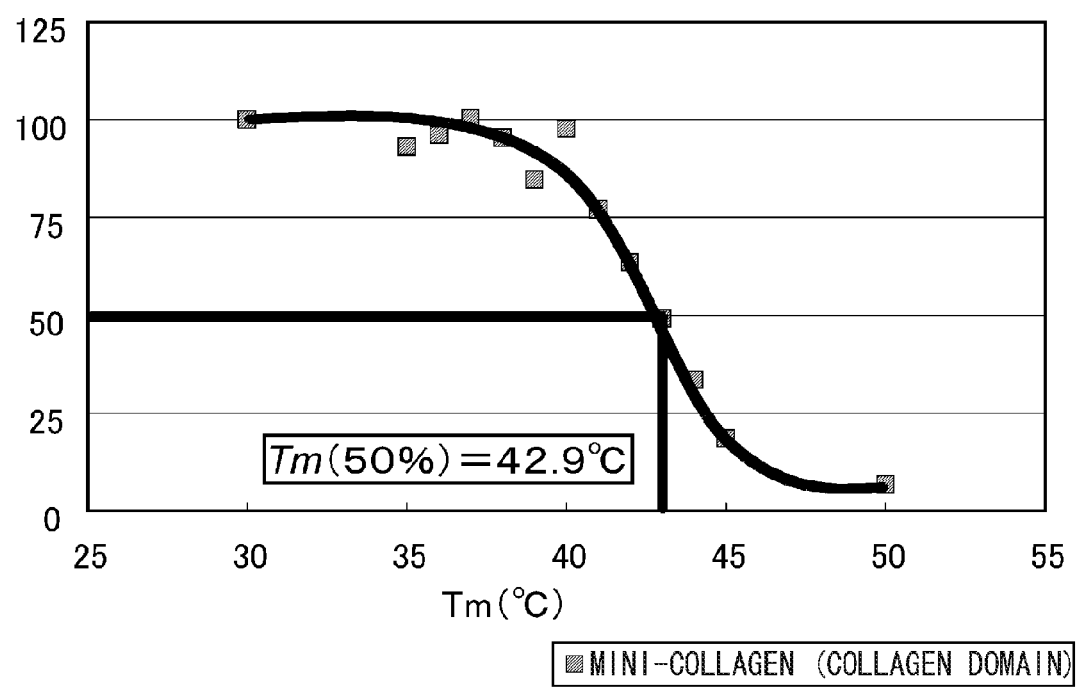
FIG. 11 is a melting curve diagram showing the proportion of the collagen domain band digested according to the heating temperature, based on the result of the thermal stability assay performed on the purified protein using trypsin and chymotrypsin of FIG. 10.

FIG. 11 shows the result of plotting a melting curve from quantifying the collagen domain bands at the respective heating temperatures, based on the results of the thermal stability assay performed in this Example for the proteins purified from the culture supernatant using trypsin and chymotrypsin, and defining the value obtained by quantifying the collagen domain band at the heat-treatment temperature of 30° C. as 100%. As a result, the heat denaturation temperature (heat-treatment temperature at which 50% is digested by the enzyme) of the collagen domain of the purified protein was 42.9° C. (FIG. 11). Since the heat denaturation temperature of naturally-occurring human atelocollagen type I is 41.9° C. (J. Biochem, 115, 853-857 (1994)), the purified protein has a thermotolerance that is equivalent or higher than that of naturally-occurring human atelocollagen type I, and is considered to be forming a stable triple helix structure.

Example 15

Purification of Mini-collagen by Utilizing Precipitation

Figure 12:
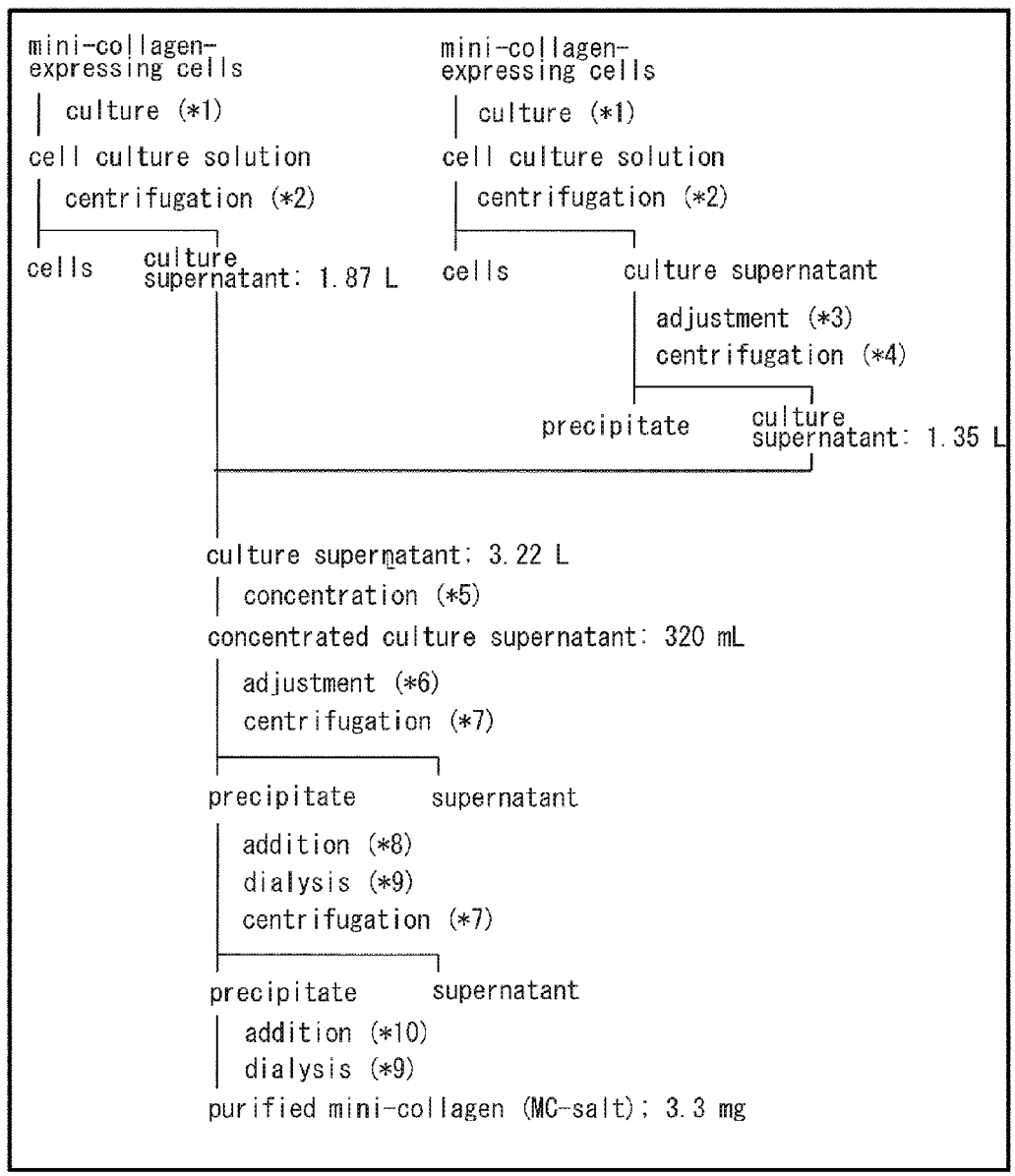
FIG. 12 is a flow chart of mini-collagen purification using precipitation. All steps were carried out at 4° C. unless specified otherwise. In the figure, *1 indicates the step of adjusting mini-collagen-expressing CHO cells (pNC7/MC-21) to 2.0× $10^5$ cells/mL with IS CHO-CD w/Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and culturing by stationary culture in T-75 flasks (FALCON) at 37° C. in the presence of 5% carbon dioxide for 14 days (HERA cell 150, Heraeus). *2 indicates the step of centrifuging at 1,750×g for 10 minutes (EX-126, TOMY). *3 indicates the step of adding sodium chloride (Wako) to the supernatant to obtain 0.4 M (pH7.4) and incubating at 4° C. *4 indicates the step of centrifuging at 10,000×g for 30 minutes (EX-126, TOMY). *5 indicates the step of concentrating the culture supernatant to a volume of 320 mL by using cross flow filtration (VIVAFLOW50; 10,000 MWCO PES; VIVASIENCE). *6 indicates the step of adding sodium chloride (Wako) to obtain 4 M (pH7.4) and incubating at 4° C. *7 indicates the step of centrifuging at 9,400×g for 30 minutes (EX-126, TOMY). *8 indicates the step of adding 1.5 mL of 50 mM acetic acid (Wako) solution to the precipitate. *9 indicates the step of dialyzing (Spectra/Pro™ Biotech Cellulose Ester (CE) Dialysis Membranes; 10,000 MWCO; Spectrum Laboratories, Inc.) against a 50 mM acetic acid (Wako) solution for five days. *10 indicates the step of adding 7.4 mL of 50 mM acetic acid solution to the precipitate.

Mini-collagen-expressing CHO cells (pNC7/MC-21) were adjusted to $2.0 \times 10^5$ cells/mL with IS CHO-CD w/ Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and cultured by stationary culture in a T-75 flask (FALCON) at 37° C. in the presence of 5% carbon dioxide for 14 days (HERA cell 150, Heraeus). The following steps were carried out at 4° C. unless specified otherwise. The culture solution was collected and centrifuged at 1,750×g for ten minutes (EX-126, TOMY) to separate the cells and supernatant. To this supernatant (1.35 L), sodium chloride (Wako) was added to obtain 0.4 M and the pH was adjusted (F-51, HORIBA) to 7.4 at 4° C. using sodium hydroxide (Wako), and this was stored at 4° C. This supernatant was centrifuged at 10,000×g for 30 minutes (EX-126, TOMY) to remove the precipitates, and the supernatant (1.35 L) was collected. Furthermore, mini-collagen-expressing CHO cells (pNC7/MC-21) were adjusted to $2.0 \times 10^5$ cells/mL with IS CHO-CD w/ Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and cultured by stationary culture in a T-75 flask (FALCON) at 37° C. in the presence of 5% carbon dioxide for 14 days (HERA cell 150, Heraeus). The culture solution was collected and centrifuged at 1,750×g for ten minutes (EX-126, TOMY) to separate the cells and supernatant (1.87 L). This supernatant (1.87 L) and the aforementioned supernatant (1.35 L) were combined (3.22 L) and concentrated to a volume of 320 mL using cross flow filtration (VIVAFLOW200; 30,000 MWCO PES; VIVASIENCE), and sodium chloride (Wako) was added to obtain a final concentration of 4 M. The pH was adjusted (F-51, HORIBA) to 7.4 at 4° C. using sodium hydroxide (Wako), and this was incubated at 25° C. for four days. Precipitates formed in this process were collected by centrifugation at 9,400×g for 30 minutes (EX-126, TOMY). To the precipitates, 1.5 mL of 50 mM acetic acid (Wako) solution was added, and the whole amount was dialyzed (Spectra/Pro™ Biotech Cellulose Ester (CE) Dialysis Membranes; 10,000 MWCO; Spectrum Laboratories, Inc.) against 50 mM acetic acid (Wako) solution for five days. Then, the dialyzed sample solution was collected and subjected to centrifugation at 9,400×g for 30 minutes (EX-126, TOMY) to collect the precipitates. To the precipitates, 7.4 mL of 50 mM acetic acid solution was added, and the whole amount was dialyzed (Spectra/Pro™ Biotech Cellulose Ester (CE) Dialysis Membranes; 10,000 MWCO; Spectrum Laboratories, Inc.) against 50 mM acetic acid solution for five days to collect 3.3 mg of the mini-collagen (hereinafter, MC-salt) (see FIG. 12).

Example 16

Purification of Mini-collagen Using the Binding with Mannan

Figure 13:
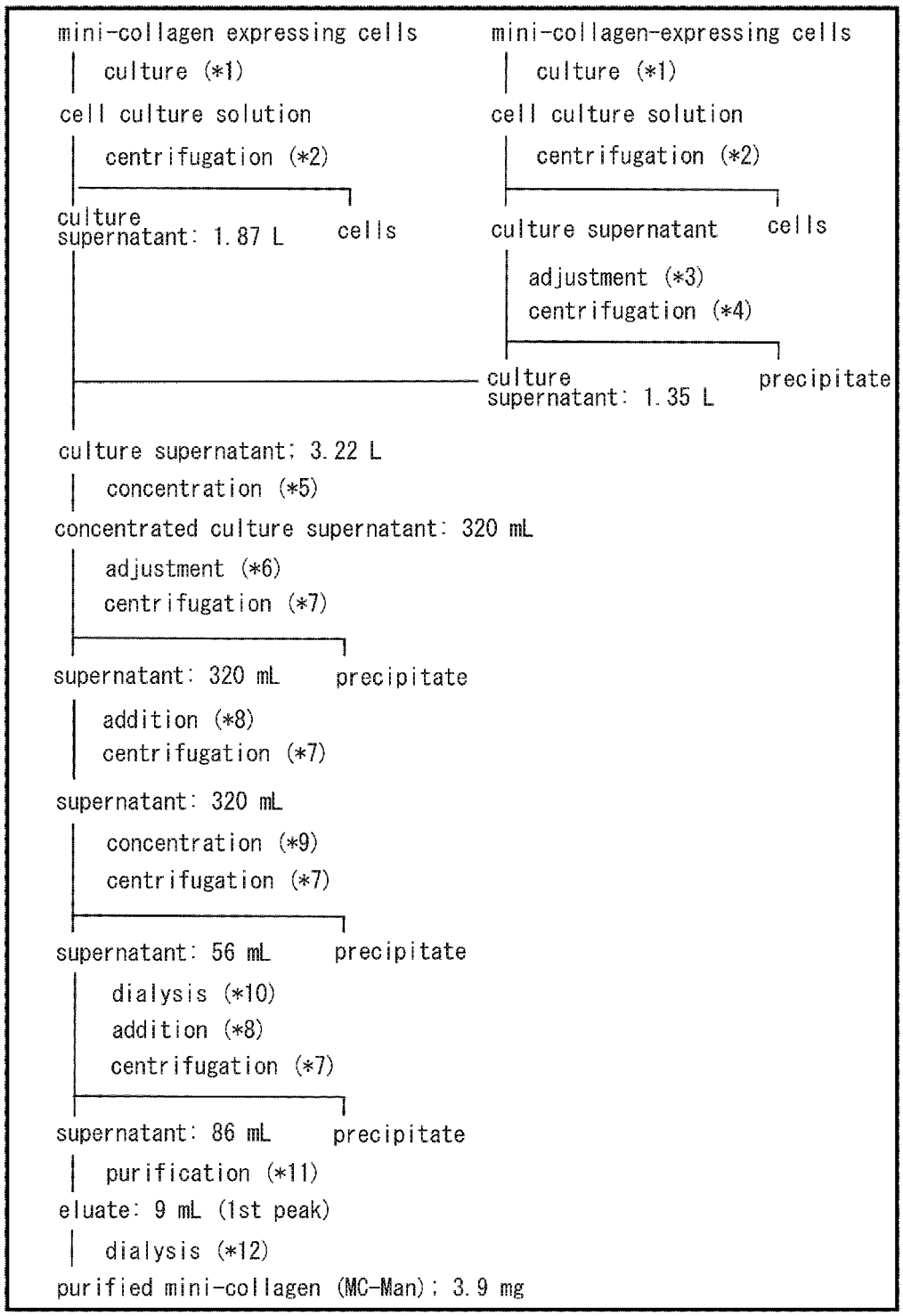
FIG. 13 is a flow chart of mini-collagen purification using the binding with mannan. All steps were carried out at 4° C. unless specified otherwise. In the figure, *1 indicates the step of adjusting mini-collagen-expressing CHO cells (pNC7/MC-21) to 2.0×$10^5$ cells/mL with IS CHO-CD w/ Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and culturing by stationary culture in T-75 flasks (FALCON) at 37° C. in the presence of 5% carbon dioxide for 14 days (HERA cell 150, Heraeus). *2 indicates the step of centrifuging at 1,750×g for 10 minutes (EX-126, TOMY). *3 indicates the step of adding sodium chloride (Wako) to the supernatant to obtain 0.4 M (pH7.4) and incubating at 4° C. *4 indicates the step of centrifuging at 10,000×g for 30 minutes (EX-126, TOMY). *5 indicates the step of concentrating the culture supernatant to a volume of 320 mL by using cross flow filtration (VIVAFLOW50; 10,000 MWCO PES; VIVASIENCE). *6 indicates the step of adding sodium chloride (Wako) to obtain 4 M (pH7.4) and incubating at 4° C. *7 indicates the step of centrifuging at 9,400×g for 30 minutes (EX-126, TOMY). *8 indicates the step of adding a 1 M calcium chloride solution to obtain 20 mM and then incubating at 4° C. for 18 hours. *9 indicates the step of concentrating the volume to 56 mL by using cross flow filtration (VIVAFLOW200; 30,000 MWCO PES; VIVASIENCE). *10 indicates the step of dialyzing (Spectra/Pro™ Biotech Dialysis Membranes; 10,000 MWCO; Spectrum Laboratories, Inc.) against TBS (TBS powder, Takara) containing 5 mM EDTA (Dojindo) for seven days. *11 indicates the steps of filling an Econo-Column (Bio-RAD) with 5 mL of mannan agarose gel (SIGMA), washing and equilibrating the gel with 15 mL of TBS (TBS powder, Takara) containing 5 mM EDTA (Dojindo) and 45 mL of TBS (TBS powder, Takara) containing 5 mM calcium chloride (Wako), loading the supernatant at a flow rate of 1.0 mL/min, then washing with 40 mL of TBS (TBS powder, Takara) containing 5 mM calcium chloride (Wako), and eluting the mini-collagen with 15 mL of TBS (TBS powder, Takara) containing 5 mM EDTA (Dojindo) to collect the first peak (9 mL). *12 indicates the step of dialyzing (Spectra/Pro™ Biotech Dialysis Membranes; 10,000 MWCO; Spectrum Laboratories, Inc.) the eluate against 0.4 M sodium chloride, 0.1 M Tris-hydrochloride buffer (pH7.4 at 4° C.) for five days.

Mini-collagen-expressing CHO cells (pNC7/MC-21) were adjusted to $2.0 \times 10^5$ cells/mL with IS CHO-CD w/ Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and cultured by stationary culture in T-75 flasks (FALCON) at 37° C. in the presence of 5% carbon dioxide for 14 days (HERA cell 150, Heraeus). The following steps were carried out at 4° C. unless specified otherwise. The culture solution was collected and centrifuged at 1,750×g for ten minutes (EX-126, TOMY) to separate the cells and supernatant. To this supernatant (1.35 L), sodium chloride (Wako) was added to obtain 0.4 M and the pH was adjusted (F-51, HORIBA) to 7.4 at 4° C. using sodium hydroxide (Wako), and this was stored at 4° C. This supernatant was centrifuged at 10,000×g for 30 minutes (EX-126, TOMY) to remove the precipitates, and the supernatant (1.35 L) was collected. Furthermore, mini-collagen-expressing CHO cells (pNC7/MC-21) were adjusted to $2.0 \times 10^5$ cells/mL with IS CHO-CD w/ Hydrolysate (IS JAPAN) medium supplemented to have final concentrations of 4 mM Gluta MAX™-I (GIBCO), 0.4 mg/mL G418 Sulfate Cell Culture Tested (CALBIOCHEM), and 1×HT supplement solution (GIBCO), and cultured by stationary culture in a T-75 flask (FALCON) at 37° C. in the presence of 5% carbon dioxide for 14 days (HERA cell 150, Heraeus). The culture solution was collected and centrifuged at 1,750×g for ten minutes (EX-126, TOMY) to separate the cells and supernatant (1.87 L). This supernatant (1.87 L) and the aforementioned supernatant (1.35 L) were combined (3.22 L) and concentrated to a volume of 320 mL using cross flow filtration (VIVAFLOW200; 30,000 MWCO PES; VIVASIENCE), and sodium chloride (Wako) was added to obtain a final concentration of 4 M. The pH was adjusted (F-51, HORIBA) to 7.4 at 4° C. using sodium hydroxide (Wako), and this was incubated at 25° C. for four days. Precipitates formed in this process were removed by centrifugation at 9,400×g for 30 minutes (EX-126, TOMY). To this supernatant (320 mL), 1 M calcium chloride solution was added to obtain 20 mM, and this was incubated at 4° C. for 18 hours and centrifuged at 9,400×g for 30 minutes (EX-126, TOMY) to separate the precipitates and the supernatant. This supernatant (320 mL) was concentrated to a volume of 56 mL using cross flow filtration (VIVAFLOW200; 30,000 MWCO PES; VIVASIENCE), and then dialyzed (Spectra/Pro™ Biotech Dialysis Membranes; 10,000 MWCO; Spectrum Laboratories, Inc.) against TBS (TBS powder, Takara) containing 5 mM EDTA (Dojindo) for seven days. To the dialyzed sample solution, 1 M calcium chloride solution was added to obtain 20 mM, and this was incubated at 4° C. for 18 hours and then centrifuged at 9,400×g for 30 minutes (EX-126, TOMY) to separate the precipitates and the supernatant. Mini-collagen remaining in this supernatant (86 mL) was purified using a mannan agarose column using the binding with mannan. An Econo-Column (Bio-RAD) was filled with 5 mL of mannan agarose gel (SIGMA), and the gel was washed and equilibrated with 15 mL of TBS (TBS powder, Takara) containing 5 mM EDTA (Dojindo) and 45 mL of TBS (TBS powder, Takara) containing 5 mM calcium chloride (Wako). The supernatant was loaded at a flow rate of 1.0 mL/min, and then washed with 40 mL of TBS (TBS powder, Takara) containing 5 mM calcium chloride (Wako). Mini-collagen was eluted using 15 mL of TBS (TBS powder, Takara) containing 5 mM EDTA (Dojindo), and the first peak (9 mL) was collected. The eluate was dialyzed (Spectra/Pro™ Biotech Dialysis Membranes; 10,000 MWCO; Spectrum Laboratories, Inc.) against 0.4 M sodium chloride, 0.1 M Tris-hydrochloride buffer (pH7.4 at 4° C.) for five days, and 3.9 mg of water-soluble mini-collagen having the activity to bind to mannan (hereinafter, MC-Man) was collected (see FIG. 13).

Example 17

Assay on Cell Adhesion to Collagen-coated Plates

Cell adhesion properties were examined by making human osteoblasts (MG-63 cells, ATCC), which are adherent cells, adhere to 96-well microplates coated with naturally-occurring human atelocollagen type I, naturally-occurring bovine atelocollagen type I, or purified mini-collagens (MC-salt, MC-Man).

Figure 14:
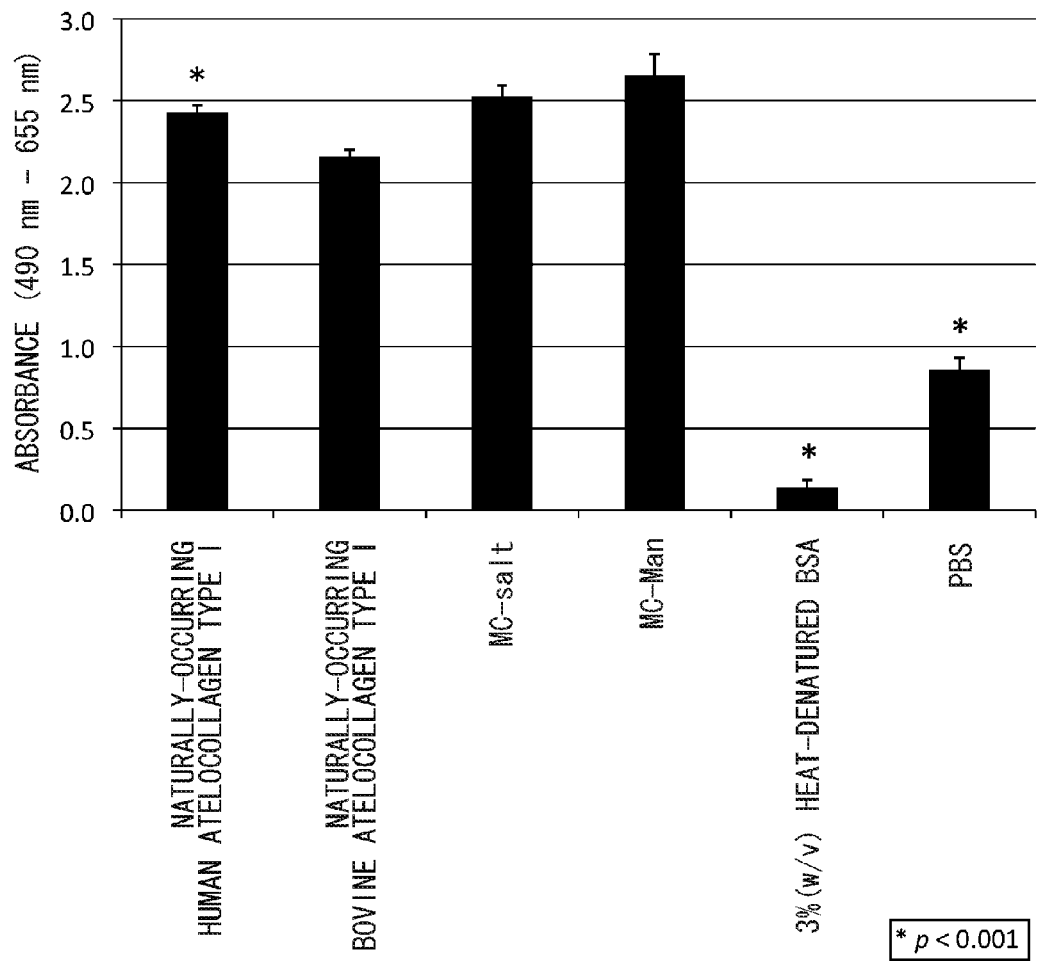
FIG. 14 shows the results of absorbance measured in human osteoblasts which are adherent cells (MG-63 cell line, ATCC), after they were adhered at 37° C. for one hour to plates coated with naturally-occurring human atelocollagen type I, naturally-occurring bovine atelocollagen type I, MC-salt, MC-Man, 3% (w/v) heat-denatured BSA solution, or PBS, non-adhered cells were removed by washing, MTS was added, and plates were cultured at 37° C. for three hours. The vertical axis shows the absorbance measured at the wavelength of 490 nm with the wavelength of 655 nm as control, and the horizontal axis shows the names of the each of the samples coated onto the plates.
Figure 15:
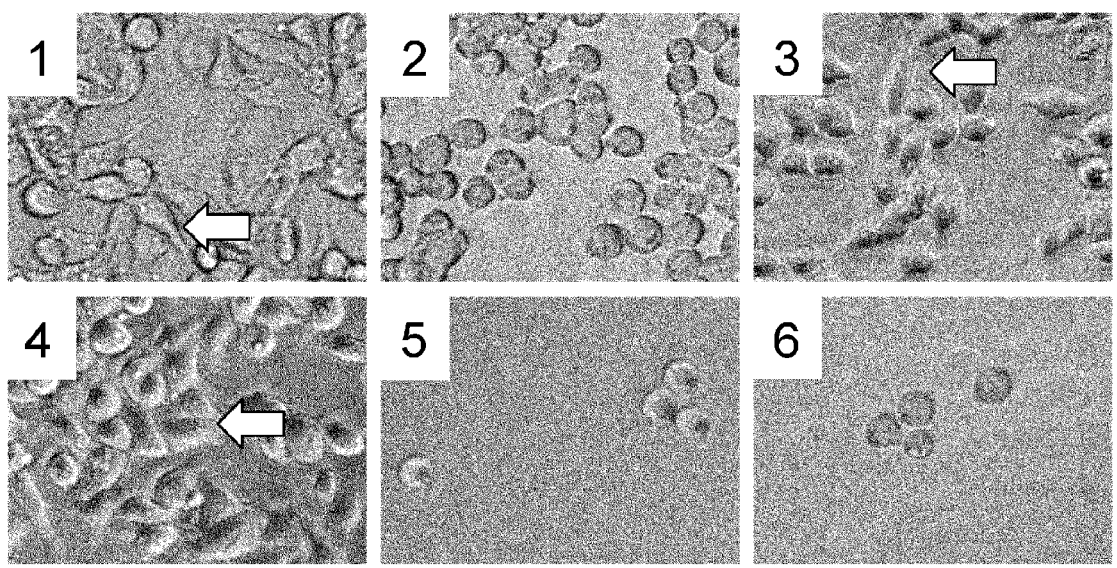
FIG. 15 shows in photographs phase contrast micrograms of cells after naturally-occurring human atelocollagen type I, naturally-occurring bovine atelocollagen type I, MC-salt, MC-Man, 3% (w/v) heat-denatured BSA solution, and PBS were coated onto the plates, human osteoblasts were made to adhere at 37° C. for one hour, and non-adhered cells were removed by washing. The photographs show the states of the human osteoblasts made to adhere onto the plates coated with: 1) naturally-occurring human atelocollagen type I; 2) naturally-occurring bovine atelocollagen type I; 3) MC-salt; 4) MC-Man; 5) 3% (w/v) heat-denatured BSA solution; and 6) PBS. Cells for which elongation was observed are indicated by arrows.
Figure 16:
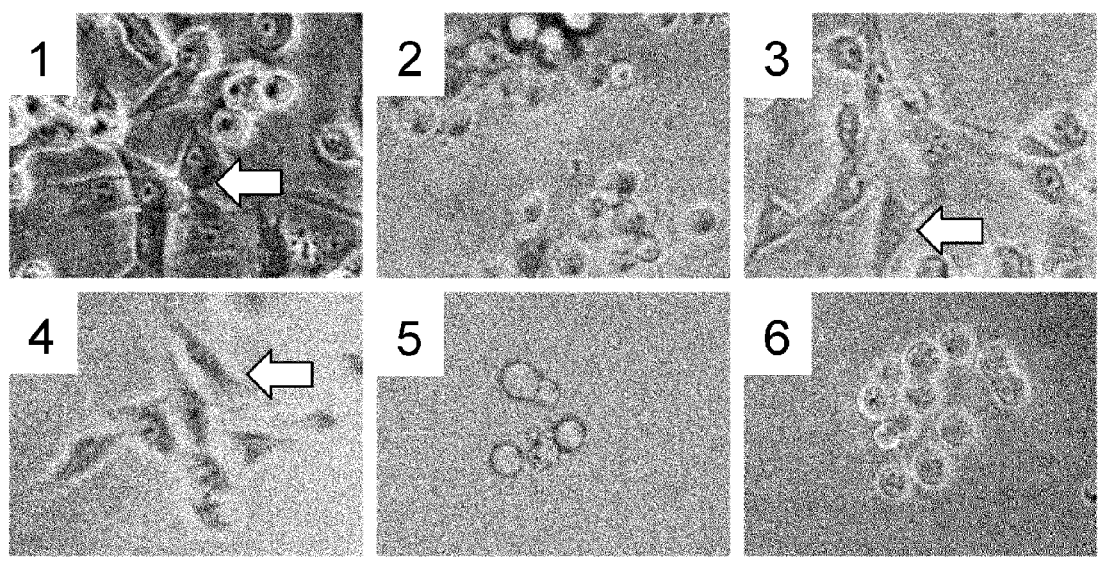
FIG. 16. shows in photographs phase contrast micrograms of cells after naturally-occurring human atelocollagen type I, naturally-occurring bovine atelocollagen type I, MC-salt, MC-Man, 3% (w/v) heat-denatured BSA solution, and PBS were coated onto the plates, human osteoblasts were made to adhere at 37° C. for one hour, non-adhered cells were removed by washing, and the plates were incubated at 37° C. for three hours. The photographs show the states of the human osteoblasts made to adhere onto the plates which were coated with: 1) naturally-occurring human atelocollagen type I; 2) naturally-occurring bovine atelocollagen type I; 3) MC-salt; 4) MC-Man; 5) 3% (w/v) heat-denatured BSA solution; and 6) PBS. Cells for which elongation was observed are indicated by arrows.

Specifically, naturally-occurring human atelocollagen type I (Collagen, Type I, Acid Soluble, From Human Skin; SIGMA-ALDRICH), naturally-occurring bovine atelocollagen type I (From Calf Skin, Cell culture tested; SIGMA), MC-salt, and MC-Man were prepared by dilution to 0.1 mg/mL in 0.1 M acetic acid (Wako). These collagen solutions, 3% (w/v) heat-denatured BSA (Invitrogen) solution, and PBS (Wako) were added to 96-well plates (F96 MAX-ISORP Nunc-Immuno plate, Nunc) at 100 µL/well and the wells were coated at room temperature for 13 hours (n=3). The coated wells were washed three times with PBS (Wako), and 1% (w/v) heat-denatured BSA (Invitrogen) solution was added at 300 mL/well for blocking at 37° C. for one hour. After blocking, the wells were washed once with PBS (Wako), and a human osteoblast (MG-63 cells, ATCC) solution adjusted to 2.5×10$^5$ cells/mL in an RPMI-1640 medium (Invitrogen) was seeded at 100 µL/well to make human osteoblasts (MG-63 cells, ATCC) adhere at 37° C. for one hour. After removing the unadhered human osteoblasts (MG-63 cell line, ATCC) by a single wash using a 1% (w/v) heat-denatured BSA (Invitrogen) solution, RPMI-1640 medium (Invitrogen) was added at 100 µL/well, and 20 µL of CellTiter 96™ Aqueous One Solution Reagent (MTS, Promega) was added. After incubation at 37° C. for three hours, the absorbance was measured at the wavelength of 490 nm with the wavelength of 655 nm as control using a microplate reader (Model 680, manufactured by BioRad) (see FIG. 14). Furthermore, human osteoblasts (MG-63 cells, ATCC) were made to adhere for one hour at 37° C., and cells that remained after removal of unadhered cells by washing (see FIG. 15) as well as cells that were subsequently incubated at 37° C. for three hours (see FIG. 16) were observed under a phase contrast microscope. The image was observed using an inverted microscope (Nikon ECLIPSE TE2000-S, manufactured by Nikon) equipped with a high-definition color camera head (DS-Fil, manufactured by Nikon) and a control unit (DS-L2, manufactured by Nikon).

As a result, the absorbances in wells coated with naturally-occurring human atelocollagen type I, naturally-occurring bovine atelocollagen type I, MC-salt, and MC-Man were twice or higher than those of the (PBS) wells not coated with collagen, and high level of adhesion of human osteoblasts due to collagen coating was observed. Furthermore, human osteoblasts were made to adhere for one hour, and cells that remained after removal of unadhered cells by washing (see FIG. 15) as well as cells that were subsequently incubated at 37° C. for three hours (see FIG. 16) were observed on a phase contrast microscope. Human osteoblasts showed adhesion and elongation in wells coated with naturally-occurring human atelocollagen type I, MC-salt, and MC-Man. However, while adhesion of human osteoblasts was observed with naturally-occurring bovine atelocollagen type I, elongation was hardly seen. From the above, MC-salt and MC-Man were found to have properties comparable to those of naturally-occurring human atelocollagen with regard to adhesion and elongation of human osteoblasts.

Example 18

Figure 17:
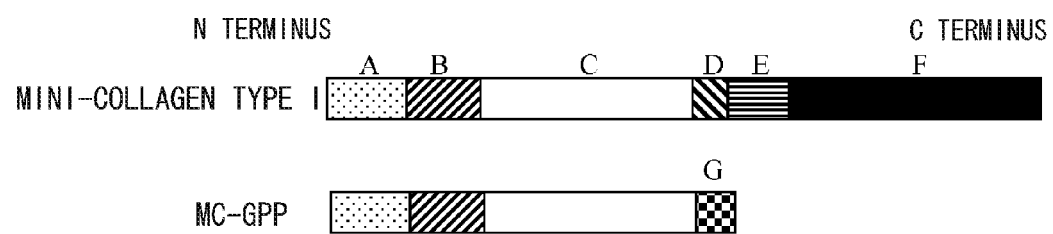
FIG. 17 shows the structures of Mini-Collagen Type I and MC-GPP. A: signal peptide domain of human surfactant protein D (SP-D); B: cysteine-rich domain of SP-D; C: human type I collagen (COL1A1) triple helix (593-769); D: COL1A1 triple helix (1178-1192); E: neck domain of human mannose binding lectin (MBL); F: carbohydrate recognition domain of MBL; and G: 6×His region are shown.
Figure 18:
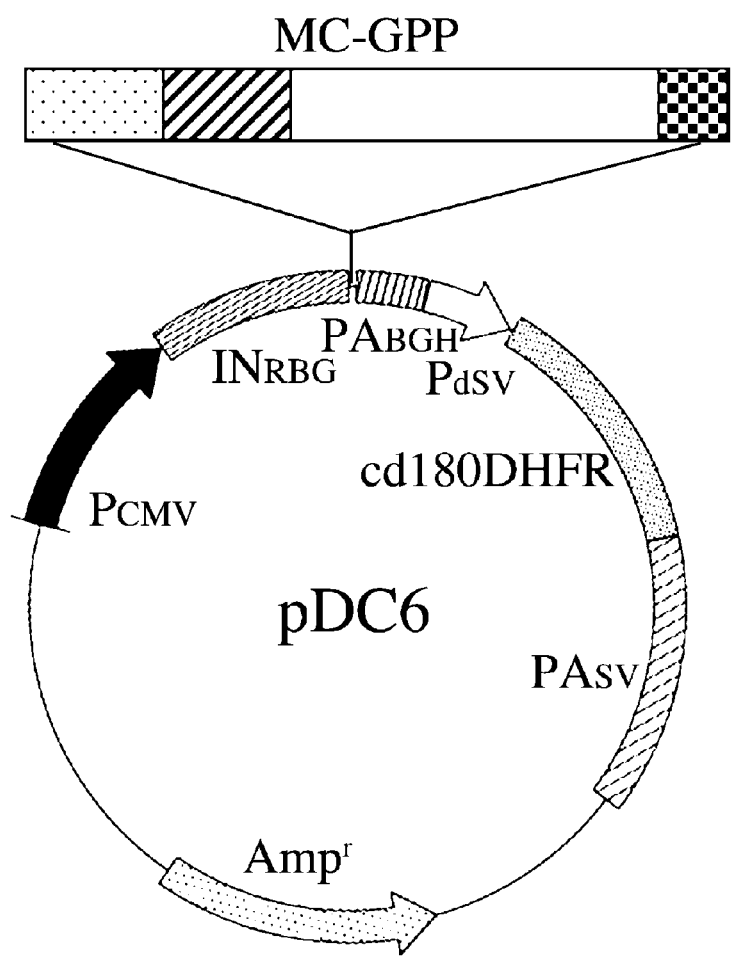
FIG. 18 shows the pDC6/MC-GPP construct with the respective abbreviations shown below. PCMV: cytomegalovirus promoter; INRBG: rabbit growth hormone intron; MC-GPP: cDNA of mini-collagen lacking the portion from the C-terminal region to the GPP region; PABGH: bovine growth hormone gene poly A addition signal; PdSV: enhancer-deleted simian virus 40 promoter; cd180DHFR: translation-impaired DHFR gene produced by altering the codons in the range of 180 bases from the 5' end of the nucleotide sequence of DHFR to the least frequently used codons in mammals; PASV: simian virus 40 poly A addition signal; and Amp$^r$: selection marker (ampicillin resistance) in *E. coli.*

Construction of Mini-collagen in which the C-terminal Region to the GPP Region is Deleted To specify the region necessary for the triple helix structure of the mini-collagen, the present inventors constructed a protein in which the portion from the C-terminal region to the GPP region of the mini-collagen is deleted (hereinafter, abbreviated as MC-GPP). FIG. 17 shows each of the regions of the mini-collagen (Mini-Collagen Type I) and MC-GPP. Using methods well known to those skilled in the art, pDC6/MC-GPP (FIG. 18) was constructed by substituting the sequence of nucleotides Nos. 1267-1275 of the pDC6 vector as described in SEQ ID NO: 14 with the MC-GPP-encoding cDNA as described in SEQ ID NO: 15.

Example 19

Introduction of pDC6/MC-GPP into CHO Cells, and Selection in an HT-Free Medium using a CD medium or a Medium Produced by Adding a Non-Animal-Based Additive to a CD Medium 2.5 µg of pDC6/MC-GPP was transfected into 4,000,000 CHO cells (CHO DG44 cells) in 25 cm$^2$-culture flasks using the Lipofectin method (Lipofectamine™ LTX, Invitrogen was used). The transfection method followed the manufacturer's instructions. 48 hours after transfection, the cell number was determined, and then the cells were diluted in an IS CHO-CD w/ H medium (IS Japan) containing 4 mM Gluta MAX™-I (Invitrogen). The cells were plated into five 96-well microtiter plates at concentrations of 4000 cells/well (480 wells), and when cultured in the presence of 5% carbon dioxide gas at 37° C. for approximately three weeks, surviving cells were observed (cell lines growing in the HT-free medium). Western blotting was carried out under reducing conditions to verify the expression of the protein of interest in the surviving cell lines. Specifically, 10 µL of Laemmli Sample Buffer (BIO-RAD) containing 5% 2-mercaptoethanol (Wako) was mixed with 10 µL each of the culture supernatants of the cell lines found to proliferate, for reduction by heating at 98° C. for five minutes (DTU-18, TAITEC). An electrophoresis buffer (Tris/Glycine/SDS, BIO-RAD) and Super Sep™ Ace 10% to 20% 17 well (Wako) were placed in an electrophoresis vessel (DPE-1020, DAIICHI PURE CHEMICALS CO., LTD), 20 μL of the heat-treated sample solutions were applied to Super Sep™ Ace 10% to 20% 17 well (Wako), and electrophoresis was carried out at 40 mA (My Run, COSMO BIO CO., LTD) for 55 minutes. Thereafter, the gel was removed from the glass plates, and soaked for five minutes while shaking (Wave-S1, TAITEC) in 10 mL of transfer buffer (Tris/Glycine Buffer (BIO-RAD) containing methanol (Wako) at 30%. The Immobilon-P Transfer Membrane (MILLIPORE) was soaked while shaking (Wave-S1, TAITEC) in 10 mL of methanol (Wako) for 15 seconds, 10 mL of ultrapure water (ELGA) for two minutes, and 10 mL of transfer buffer (Tris/Glycine Buffer (BIO-RAD) containing 30% methanol (Wako)) for five minutes. In a transfer apparatus (TRANS-BLO, SD SEMI-DRY TRANSFER CELL, BIO-RAD), transfer buffer (Tris/Glycine Buffer (BIO-RAD) containing 30% methanol (Wako))-soaked filter papers (Extra Thick Blot Paper Protean™ XL Size, BIO-RAD), Immobilon-P Transfer Membrane (MILLIPORE), gel, and filter papers (Extra Thick Blot Paper Protean™ XL Size, BIO-RAD) were laid in order from the minus side, a cover was placed, and electrophoresis was carried out at 80 mA (PowerPac HC™, BIO-RAD) for 90 minutes to transfer the separated proteins onto the Immobilon-P Transfer Membrane (MILLIPORE). After transfer, the Immobilon-P Transfer Membrane (MILLIPORE) was soaked in 10 mL of Immuno-Block (Laboratory Products division of Dainippon Sumitomo Pharma Co., Ltd.) and blocked at 4° C. for 18 hours, then washed three times by shaking (Wave-S1, TAITEC) for five minutes in 10 mL of PBS (Wako) containing 0.05% Tween 20 (Polyoxyethylene (20) Sorbitan Monolaurate, Wako). 10 mL of a 6-His monoclonal antibody (COVANCE) diluted 1,000 times with PBS (Wako) containing 0.05% Tween 20 (Polyoxyethylene (20) Sorbitan Monolaurate, Wako) and the proteins on the membrane were reacted for one hour at room temperature while shaking (Wave-S1, TAITEC). After the unbound antibodies were removed, the membrane was washed three times by shaking for five minutes (Wave-S1, TAITEC) in 10 mL of PBS (Wako) containing 0.05% Tween 20 (Polyoxyethylene (20) Sorbitan Monolaurate, Wako). 10 mL of a goat anti-mouse IgG(H+L)HRP (Jackson ImmunoResearch) diluted 5,000 times in PBS (Wako) containing 0.05% Tween 20 (Polyoxyethylene (20) Sorbitan Monolaurate, Wako) was added, and reaction was allowed to take place at room temperature for one hour while shaking (Wave-S1, TAITEC). After the unbound antibodies were removed, the membrane was washed three times by shaking (Wave-S1, TAITEC) for ten minutes in 24 mL of PBS (Wako) containing 0.05% Tween 20 (Polyoxyethylene (20) Sorbitan Monolaurate, Wako). 2 mL of Immobilon Western Chemiluminescent HRP Substrate (MILLIPORE) was added for chemiluminescence, and a 10-second to one-minute photograph was taken using Light-Capture ATTO Cooled CCD Camera System (ATTO) at its normal settings. Cells for which MC-GPP expression was detected were transferred to 24-well plates together with IS CHO-CD w/ Hydrolysate medium (IS Japan) containing 4 mM Gluta MAX™-I (Invitrogen), and the cells were cultured until they occupied ⅓ or more of each well. Western blotting was carried out under reducing conditions as described above, and cells in the wells in which MC-GPP expression was detected were transferred to 6-well plates together with IS CHO-CD w/ Hydrolysate medium (IS Japan) containing 4 mM Gluta MAX™-I (Invitrogen), and the cells were cultured until they occupied ⅓ or more of each well. Cell lines for which further proliferation was observed and MC-GPP expression was detected by Western blotting under reducing conditions were transferred to T-75 Flasks (BD) together with IS CHO-CD w/ Hydrolysate medium (IS Japan) containing 4 mM Gluta MAX™-I (Invitrogen), and the cells were cultured until they reached $1.0 \times 10^6$ cells/mL in each well.

Example 20

Purification of MC-GPP

MC-GPP-expressing CHO cells (pDC6/MC-GPP-3) were cultured with IS CHO-CD w/Hydrolysate medium (IS JAPAN) by stationary culture in T-75 flasks (FALCON) at 37° C. in the presence of 5% carbon dioxide (HERA cell 150, Heraeus). The culture solutions were collected and centrifuged at 1,750×g for ten minutes (EX-126, TOMY) to separate the cells and the supernatant, and this supernatant was loaded onto a Ni column to purify MC-GPP. Specifically, a Poly empty column (BIO-RAD) was filled with 1 mL of Ni-NTA agarose gel (Invitrogen) and the gel was washed with 6 mL of ultrapure water (BMS). Subsequently, the gel was washed three times with 6 mL of Native binding buffer (0.25 M sodium dihydrogen phosphate (Wako), 2.5 M sodium chloride (Wako), 0.01 M imidazole (Wako), pH8.0), and 8 mL of the culture supernatant was loaded onto the column. The column was capped and binding took place while mixing at 4° C. for 60 minutes (Aikuru, IWAKI). The gel was washed nine times with 6 mL of Native wash buffer (0.25 M sodium dihydrogen phosphate (Wako), 2.5 M sodium chloride (Wako), 0.02 M imidazole (Wako), pH8.0), and elution was carried out six times, 1 mL at a time using Native elution buffer (0.23 M sodium dihydrogen phosphate (Wako), 2.3 M sodium chloride (Wako), 0.25 M imidazole (Wako), pH8.0). The initial 2 mL of eluate was dialyzed against 0.02 M acetic acid solution at 4° C. for three days, and then the MC-GPP solution was collected.

Example 21

SDS polyacrylamide gel electrophoresis of MC-GPP under reducing conditions

Figure 19:
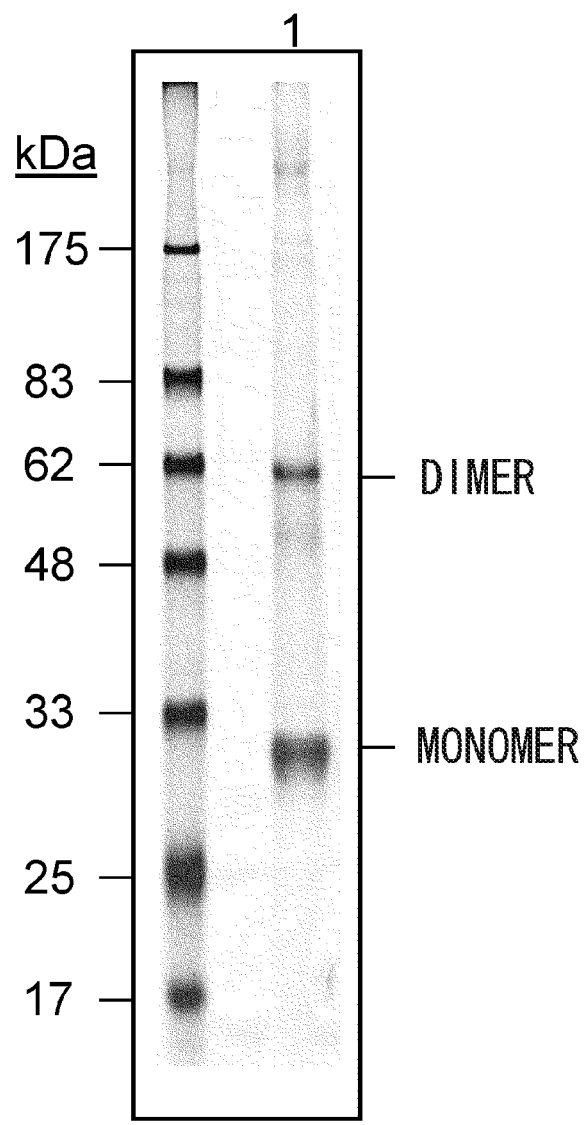
FIG. 19 shows in a photograph the analysis result of SDS polyacrylamide gel electrophoresis under reducing conditions (2-mercaptoethanol added) of MC-GPP purified from the culture supernatant. Lane 1 is the purified MC-GPP, and the molecular weight and MC-GPP oligomers are indicated on the photograph.

Purified MC-GPP was analyzed by SDS polyacrylamide gel electrophoresis under reducing conditions. Specifically, 10 μL of Laemmli Sample Buffer (BIO-RAD) containing 5% of 2-mercaptoethanol (Wako) was added to 10 μL of purified MC-GPP for reduction by heating at 98° C. for five minutes (DTU-18, TAITEC). An electrophoresis buffer (Tris/Glycine/SDS, BIO-RAD) and Super Sep™ Ace 10% to 20% 17 well (Wako) were placed in an electrophoresis vessel (DPE-1020, DAIICHI PURE CHEMICALS CO., LTD), and 15 μL of the heat-treated sample solutions were applied to Super Sep™ Ace 10% to 20% 17 well (Wako), and electrophoresis was carried out at 40 mA (My Run, COSMO BIO CO., LTD) for 55 minutes. Then, silver staining was carried out using 2D-Silver Stain Reagent II (COSMO BIO CO., LTD). First, the gel was fixed by shaking for 20 minutes in 40 mL of fixing solution-I (50% methanol (Wako), 10% acetic acid (Wako), and 40% water (BMS)). Next, the gel was fixed by shaking for 30 minutes in 40 mL of fixing solution-II (30% methanol (Wako)-10% acetic acid (Wako), 5% fixing agent (2D-Silver Stain Reagent II, COSMO BIO CO., LTD.), and 55% ultrapure water (BMS)). Then, pretreatment was carried out by shaking for 20 minutes in 40 mL of pretreatment solution (50% methanol (Wako), 5% pretreatment agent (2D-Silver Stain Reagent II, COSMO BIO CO., LTD.), and 45% ultrapure water (BMS)). The gel was washed for ten minutes with 40 mL of ultrapure water (BMS), stained for 30 minutes using 40 mL of silver staining solution (5% staining solution A (2D-Silver Stain Reagent II, COSMO BIO CO., LTD.), 5% staining solution B (2D-Silver Stain Reagent II, COSMO BIO CO., LTD.), and 90% ultrapure water (BMS)), and then washed for five minutes using 40 mL of ultrapure water (BMS). The wash was repeated three times. The gel was developed for eight minutes using 40 mL of developing solution (5% developing stock solution (2D-Silver Stain Reagent II, COSMO BIO CO., LTD.) and 95% ultrapure water (BMS)), and 2 mL of stop solution (2D-Silver Stain Reagent II, COSMO BIO CO., LTD.)) was added to stop the development. Finally, the gel was washed for ten minutes using 40 mL of ultrapure water (BMS), and an image was scanned (see FIG. 19) using a scanner (GT-X900, EPSON).

Example 22

SDS Polyacrylamide Gel Electrophoresis of MC-GPP Under Non-reducing Conditions

Figure 20:
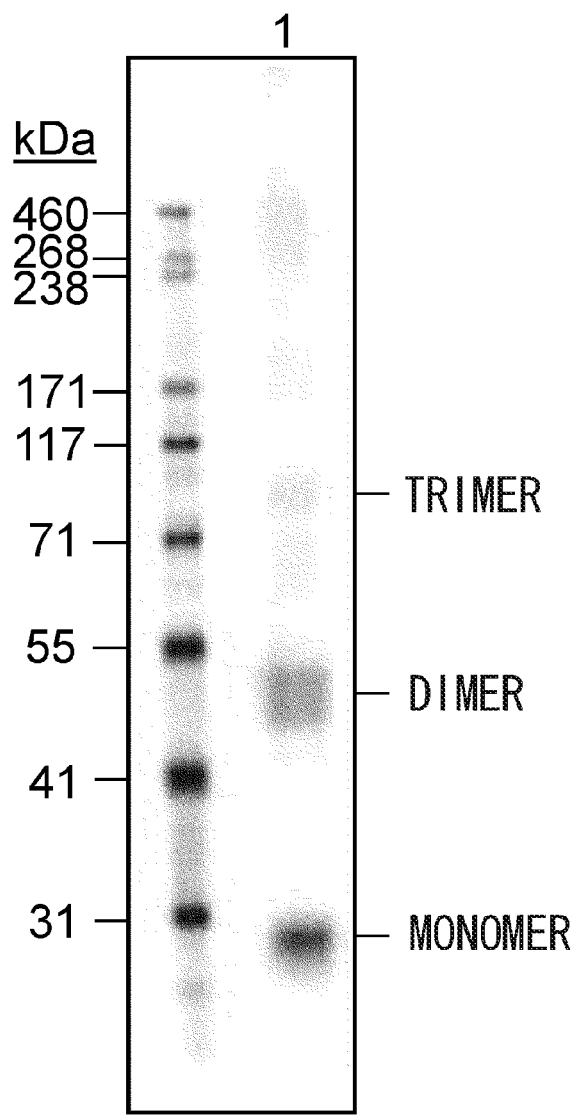
FIG. 20 shows in a photograph the analysis result of SDS polyacrylamide gel electrophoresis under non-reducing conditions (no 2-mercaptoethanol added) of MC-GPP purified from the culture supernatant. Lane 1 is the purified MC-GPP, and the molecular weight and MC-GPP oligomers are indicated on the photograph.

Purified MC-GPP was analyzed by SDS polyacrylamide gel electrophoresis under non-reducing conditions. Specifically, 10 µL of Laemmli Sample Buffer (BIO-RAD) was added to 10 µL of purified MC-GPP, and this was subjected to heat treatment at 98° C. for five minutes (DTU-18, TAITEC). An electrophoresis buffer (Tris/Glycine/SDS, BIO-RAD) and Super Sep™ Ace 5% to 20% 17 well (Wako) were placed in an electrophoresis vessel (DPE-1020, DAIICHI PURE CHEMICALS CO., LTD), and 15 µL of the heat-treated sample solutions were applied to Super Sep™ Ace 5% to 20% 17 well (Wako), and electrophoresis was carried out at 40 mA (My Run, COSMO BIO CO., LTD) for 55 minutes. Then, silver staining was carried out using 2D-Silver Stain Reagent II (COSMO BIO CO., LTD). First, the gel was fixed by shaking for 20 minutes in 40 mL of fixing solution-I (50% methanol (Wako), 10% acetic acid (Wako), and 40% water (BMS)). Next, the gel was fixed by shaking for 30 minutes in 40 mL of fixing solution-II (30% methanol (Wako), 10% acetic acid (Wako), 5% fixing agent (2D-Silver Stain Reagent II, COSMO BIO CO., LTD.), and 55% ultrapure water (BMS)). Then, pretreatment was carried out by shaking for 20 minutes in 40 mL of pretreatment solution (50% methanol (Wako), 5% pretreatment agent (2D-Silver Stain Reagent II, COSMO BIO CO., LTD.), and 45% ultrapure water (BMS)). The gel was washed for ten minutes with 40 mL of ultrapure water (BMS), stained for 30 minutes using 40 mL of silver staining solution (5% staining solution A (2D-Silver Stain Reagent II, COSMO BIO CO., LTD.), 5% staining solution B (2D-Silver Stain Reagent II, COSMO BIO CO., LTD.), and 90% ultrapure water (BMS)), then washed for five minutes using 40 mL of ultrapure water (BMS). The wash was repeated three times. The gel was developed for eight minutes using 40 mL of developing solution (5% developing stock solution (2D-Silver Stain Reagent II, COSMO BIO CO., LTD.) and 95% ultrapure water (BMS)), and 2 mL of stop solution (2D-Silver Stain Reagent II, COSMO BIO CO., LTD.)) was added to stop the development. Finally, the gel was washed for ten minutes using 40 mL of ultrapure water (BMS), and an image was scanned (see FIG. 20) using a scanner (GT-X900, EPSON).

Example 23

Native Polyacrylamide Gel Electrophoresis of MC-GPP

Figure 21:
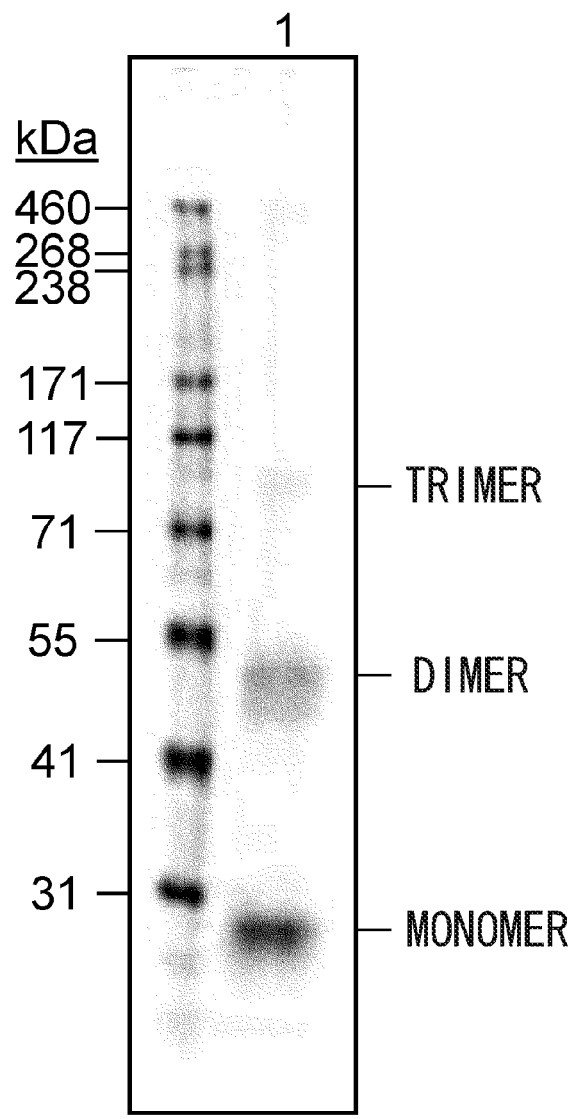
FIG. 21 shows in a photograph the analysis result of polyacrylamide gel electrophoresis under native conditions (no 2-mercaptoethanol and SDS added) of MC-GPP purified from the culture supernatant. Lane 1 is the purified MC-GPP, and the molecular weight and MC-GPP oligomers are indicated on the photograph.

Purified MC-GPP was analyzed by native polyacrylamide gel electrophoresis. Specifically, 10 µL of Native Sample Buffer (BIO-RAD) was added to 10 µL of purified MC-GPP. An electrophoresis buffer (Tris/Glycine/SDS, BIO-RAD) and Super Sep™ Ace 5% to 20% 17 well (Wako) were placed in an electrophoresis vessel (DPE-1020, DAIICHI PURE CHEMICALS CO., LTD), 15 µL of the prepared sample solutions were applied to Super Sep™ Ace 5% to 20% 17 well (Wako), and electrophoresis was carried out at 40 mA (My Run, COSMO BIO CO., LTD) for 55 minutes. Then, silver staining was carried out using 2D-Silver Stain Reagent II (COSMO BIO CO., LTD). First, the gel was fixed by shaking for 20 minutes in 40 mL of fixing solution-I (50% methanol (Wako), 10% acetic acid (Wako), and 40% water (BMS)). Next, the gel was fixed by shaking for 30 minutes in 40 mL of fixing solution-II (30% methanol (Wako), 10% acetic acid (Wako), 5% fixing agent (2D-Silver Stain Reagent II, COSMO BIO CO., LTD.), and 55% ultrapure water (BMS)). Pretreatment was carried out by shaking for 20 minutes in 40 mL of pretreatment solution (50% methanol (Wako), 5% pretreatment agent (2D-Silver Stain Reagent II, COSMO BIO CO., LTD.), and 45% ultrapure water (BMS)). The gel was washed for ten minutes with 40 mL of ultrapure water (BMS), stained for 30 minutes using 40 mL of silver staining solution (5% staining solution A (2D-Silver Stain Reagent II, COSMO BIO CO., LTD.), 5% staining solution B (2D-Silver Stain Reagent II, COSMO BIO CO., LTD.), and 90% ultrapure water (BMS)), then washed for five minutes using 40 mL of ultrapure water (BMS). The wash was repeated three times. The gel was developed for eight minutes using 40 mL of developing solution (5% developing stock solution (2D-Silver Stain Reagent II, COSMO BIO CO., LTD.) and 95% ultrapure water (BMS)), and 2 mL of stop solution (2D-Silver Stain Reagent II, COSMO BIO CO., LTD.)) was added to stop the development. Finally, the gel was washed for ten minutes using 40 mL of ultrapure water (BMS), and an image was scanned (see FIG. 21) using a scanner (GT-X900, EPSON).

Example 24

Western Blotting of MC-GPP Under Reducing Conditions

Figure 22:
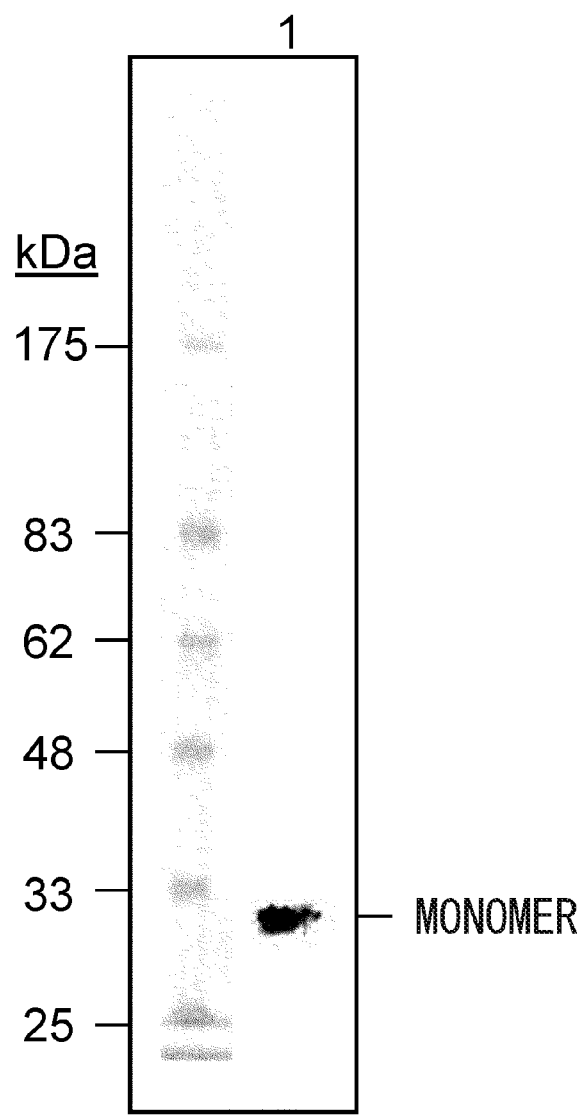
FIG. 22 shows in a photograph the result obtained by performing Western blotting under reducing conditions (2-mercaptoethanol added) of MC-GPP purified from the culture supernatant and reversing the contrast of the photograph of chemiluminescence detection. Lane 1 is the purified MC-GPP, and the molecular weight and MC-GPP oligomer are indicated on the photograph.

Since MC-GPP has a His-tag on its C-terminal side, anti-His antibodies can bind to it. Western blotting was carried out under reducing conditions by utilizing this property, and purified MC-GPP was detected and identified by chemiluminescence. Specifically, 10 µL of Laemmli Sample Buffer (BIO-RAD) containing 5% 2-mercaptoethanol (Wako) was added to 10 µL of purified MC-GPP for reduction by heating at 98° C. for five minutes (DTU-18, TAITEC). An electrophoresis buffer (Tris/Glycine/SDS, BIO-RAD) and Super Sep™ Ace 5% to 20% 17 well (Wako) were placed in an electrophoresis vessel (DPE-1020, DAIICHI PURE CHEMICALS CO., LTD), and 15 µL of the heat-treated sample solutions were applied to Super Sep™ Ace 5% to 20% 17 well (Wako), and electrophoresis was carried out at 40 mA (My Run, COSMO BIO CO., LTD) for 55 minutes. Then, the gel was removed from the glass plates, and soaked for five minutes while shaking (Wave-S1, TAITEC) in 10 mL of transfer buffer (Tris/Glycine Buffer (BIO-RAD) containing 30% methanol (Wako)). Immobilon-P Transfer Membrane (MILLIPORE) was soaked while shaking (Wave-S1, TAITEC) in 10 mL of methanol (Wako) for 15 seconds, 10 mL of ultrapure water (ELGA) for two minutes, and 10 mL of transfer buffer (Tris/Glycine Buffer (BIO-RAD) containing 30% methanol (Wako)) for five minutes. In a transfer apparatus (TRANS-BLO, SD SEMI-DRY TRANSFER CELL, BIO-RAD), transfer buffer (Tris/Glycine Buffer (BIO-RAD) containing 30% methanol (Wako))-soaked filter papers (Extra Thick Blot Paper Protean™ XL Size, BIO-RAD), Immobilon-P Transfer Membrane (MILLIPORE), gel, and filter papers (Extra Thick Blot Paper Protean™ XL Size, BIO-RAD) were laid in order from the minus side, a cover was placed, and electrophoresis was carried out at 80 mA (PowerPac HC™, BIO-RAD) for 90 minutes to transfer the separated proteins onto the Immobilon-P Transfer Membrane (MILLIPORE). After transfer, the Immobilon-P Transfer Membrane (MILLIPORE) was soaked in 10 mL of ImmunoBlock (Laboratory Products division of Dainippon Sumitomo Pharma Co., Ltd.) and blocked at 4° C. for 18 hours, then washed three times by shaking (Wave-S1, TAITEC) for five minutes in 10 mL of PBS (Wako) containing 0.05% Tween 20 (Polyoxyethylene (20) Sorbitan Monolaurate, Wako). 10 mL of a 6-His monoclonal antibody (COVANCE) diluted 1,000 times with PBS (Wako) containing 0.05% Tween 20 (Polyoxyethylene (20) Sorbitan Monolaurate, Wako) and the proteins on the membrane were reacted for one hour at room temperature while shaking (Wave-S1, TAITEC). After the unbound antibodies were removed, the membrane was washed three times by shaking (Wave-S1, TAITEC) for five minutes in 10 mL of PBS (Wako) containing 0.05% Tween 20 (Polyoxyethylene (20) Sorbitan Monolaurate, Wako). 10 mL of a goat anti-mouse IgG(H+L)HRP (Jackson ImmunoResearch) diluted 5,000 times in PBS (Wako) containing 0.05% Tween 20 (Polyoxyethylene (20) Sorbitan Monolaurate, Wako) was added, and reaction took place at room temperature while shaking for one hour (Wave-S1, TAITEC). After the unbound antibodies were removed, the membrane was washed three times by shaking (Wave-S1, TAITEC) for ten minutes in 24 mL of PBS (Wako) containing 0.05% Tween 20 (Polyoxyethylene (20) Sorbitan Monolaurate, Wako). 2 mL of Immobilon Western Chemiluminescent HRP Substrate (MILLIPORE) was added for chemiluminescence, and a 30-second photograph (see FIG. 22) was taken using Light-Capture ATTO Cooled CCD Camera System (ATTO) at its normal settings.

Example 25

Western Blotting of MC-GPP Under Non-reducing Conditions

Figure 23:
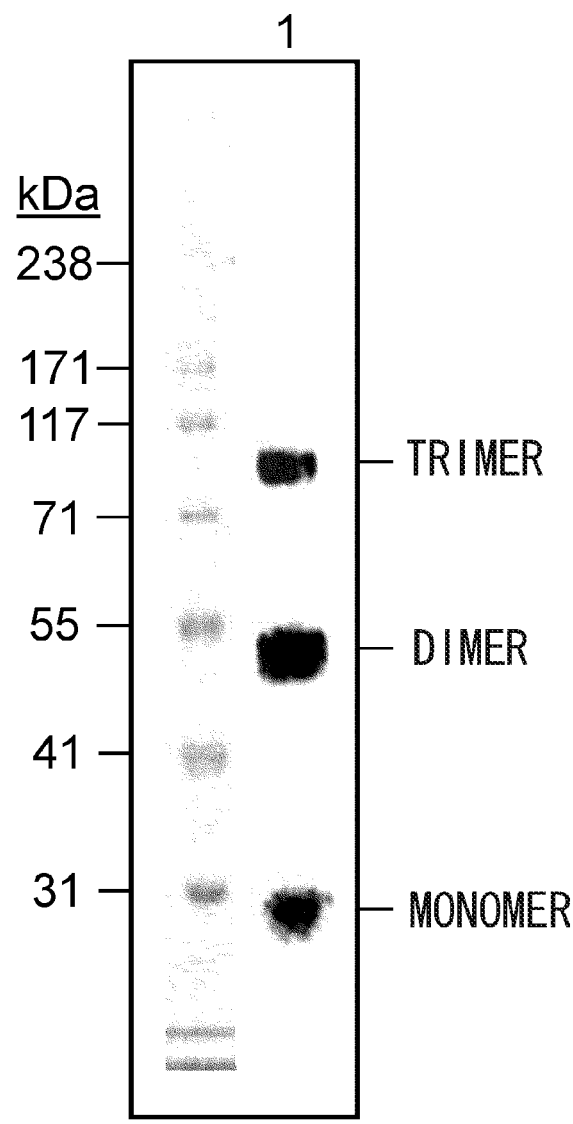
FIG. 23 shows in a photograph the result obtained by performing Western blotting under non-reducing conditions (no 2-mercaptoethanol added) of MC-GPP purified from the culture supernatant and reversing the contrast of the photograph of chemiluminescence detection. Lane 1 is the purified MC-GPP, and the molecular weight and MC-GPP oligomers are indicated on the photograph.

Since MC-GPP has a His-tag on its C-terminal side, anti-His antibodies can bind to it. Western blotting was carried out under non-reducing conditions by utilizing this property, and purified MC-GPP was detected and identified by chemiluminescence. Specifically, 10 μL of Laemmli Sample Buffer (BIO-RAD) was added to 10 μL of purified MC-GPP for heat treatment at 98° C. for five minutes (DTU-18, TAITEC). An electrophoresis buffer (Tris/Glycine/SDS, BIO-RAD) and Super Sep Ace 5% to 20% 17 well (Wako) were placed in an electrophoresis vessel (DPE-1020, DAIICHI PURE CHEMICALS CO., LTD), and 15 μL of the heat-treated sample solutions were applied to Super Sep™ Ace 5% to 20% 17 well (Wako), and electrophoresis was carried out at 40 mA (My Run, COSMO BIO CO., LTD) for 55 minutes. Then, the gel was removed from the glass plates, and soaked for five minutes while shaking (Wave-S1, TAITEC) in a transfer buffer (Tris/Glycine Buffer (BIO-RAD) containing 30% methanol (Wako)). Immobilon-P Transfer Membrane (MILLIPORE) was soaked while shaking (Wave-S1, TAITEC) in 10 mL of methanol (Wako) for 15 seconds, 10 mL of ultrapure water (ELGA) for two minutes, and 10 mL of transfer buffer (Tris/Glycine Buffer (BIO-RAD) containing 30% methanol (Wako)) for five minutes. In a transfer apparatus (TRANS-BLO, SD SEMI-DRY TRANSFER CELL, BIO-RAD), transfer buffer (Tris/Glycine Buffer (BIO-RAD) containing 30% methanol (Wako))-soaked filter papers (Extra Thick Blot Paper Protean™ XL Size, BIO-RAD), Immobilon-P Transfer Membrane (MILLIPORE), gel, and filter papers (Extra Thick Blot Paper Protean™ XL Size, BIO-RAD) were laid in order from the minus side, a cover was placed, and electrophoresis was carried out at 80 mA (PowerPac HC™, BIO-RAD) for 90 minutes to transfer the separated proteins onto the Immobilon-P Transfer Membrane (MILLIPORE). After transfer, the Immobilon-P Transfer Membrane (MILLIPORE) was soaked in 10 mL of ImmunoBlock (Laboratory Products division of Dainippon Sumitomo Pharma Co., Ltd.) and blocked at 4° C. for 18 hours, then washed three times by shaking (Wave-S1, TAITEC) for five minutes in 10 mL of PBS (Wako) containing 0.05% Tween20 (Polyoxyethylene (20) Sorbitan Monolaurate, Wako). 10 mL of a 6-His monoclonal antibody (COVANCE) diluted 1,000 times with PBS (Wako) containing 0.05% Tween 20 (Polyoxyethylene (20) Sorbitan Monolaurate, Wako) and the proteins on the membrane were reacted for one hour at room temperature while shaking (Wave-S1, TAITEC). After the unbound antibodies were removed, the membrane was washed three times by shaking (Wave-S1, TAITEC) for five minutes in 10 mL of PBS (Wako) containing 0.05% Tween 20 (Polyoxyethylene (20) Sorbitan Monolaurate, Wako). 10 mL of a goat anti-mouse IgG(H+L)HRP (Jackson ImmunoResearch) diluted 5,000 times in PBS (Wako) containing 0.05% Tween 20 (Polyoxyethylene (20) Sorbitan Monolaurate, Wako) was added, and reaction took place at room temperature while shaking for one hour (Wave-S1, TAITEC). After the unbound antibodies were removed, the membrane was washed three times by shaking (Wave-S1, TAITEC) for ten minutes in 24 mL of PBS (Wako) containing 0.05% Tween 20 (Polyoxyethylene (20) Sorbitan Monolaurate, Wako). 2 mL of Immobilon Western Chemiluminescent HRP Substrate (MILLIPORE) was added for chemiluminescence, and a 30-second photograph (see FIG. 23) was taken using Light-Capture ATTO Cooled CCD Camera System (ATTO) at its normal settings.

Example 26

Pepsin Digestion of MC-GPP and Naturally-occurring Human Atelocollagen

Figure 24:
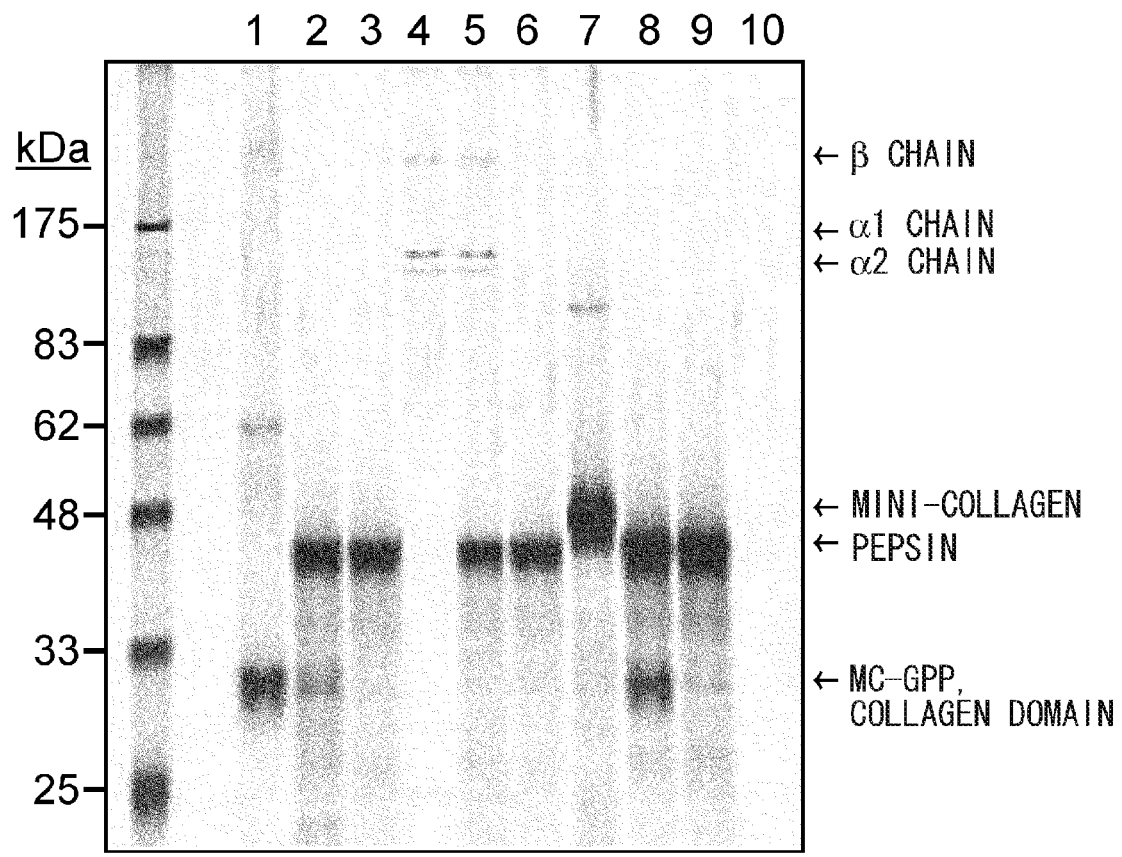
FIG. 24 shows in a photograph the analysis result of SDS polyacrylamide gel electrophoresis under reducing conditions (2-mercaptoethanol added) performed on MC-GPP, naturally-occurring human atelocollagen type I, and purified fibrous mini-collagen digested with pepsin under acidic conditions. Positions of the bands for MC-GPP, naturally-occurring human atelocollagen ($\alpha 1$, $\alpha 2$, $\beta$, and $\gamma$ chains), mini-collagen, the remaining collagen domain of mini-collagen or MC-GPP after digestion, and pepsin are indicated on the photograph. Lane 1: MC-GPP addition; lane 2: addition of pepsin-digested MC-GPP; lane 3: addition of pepsin alone (same amount as in lane 2); lane 4: addition of naturally-occurring human atelocollagen type I; lane 5: addition of pepsin-digested naturally-occurring human atelocollagen type I; lane 6: addition of pepsin alone (same amount as in lane 5); lane 7: addition of purified fibrous mini-collagen; lane 8: addition of pepsin-digested purified fibrous mini-collagen; lane 9: addition of pepsin alone (same amount as in lane 8); and lane 10: no addition of MC-GPP, naturally-occurring human atelocollagen type I, mini-collagen, and pepsin.
Figure 25:
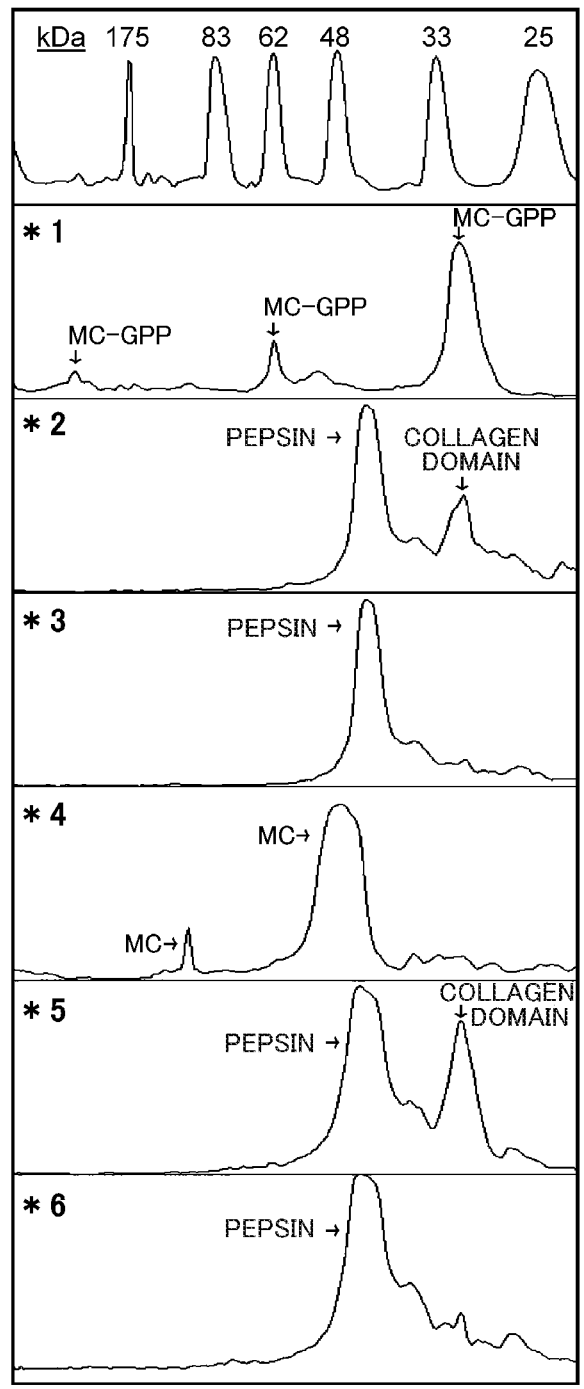
FIG. 25 is a diagram obtained after digesting MC-GPP and purified fibrous mini-collagen with pepsin under acidic conditions and analyzing using ImageJ the bands from images of SDS polyacrylamide gel electrophoresis performed under reducing conditions (2-mercaptoethanol added). *1 is MC-GPP, *2 is pepsin-digested MC-GPP, 3* is pepsin alone (same amount as in *2), *4 is purified fibrous mini-collagen, *5 is pepsin-digested purified fibrous mini-collagen, and *6 is pepsin alone (same amount as in *5). The marker bands and their molecular weights are analyzed as shown in the chart.

Collagen that forms a triple helix structure is resistant against cleavage by pepsin. Therefore, purified MC-GPP, naturally-occurring human atelocollagen type I (Collagen, Type I, Acid Soluble, From Human Skin, SIGMA-ALDRICH), and purified fibrous mini-collagen (Example 7) were digested with pepsin under acidic conditions, and resistance against cleavage by pepsin was verified from SDS polyacrylamide electrophoresis images. More specifically, 3 μL of 0.3 M hydrochloric acid solution was added to 10 μL each of purified MC-GPP (0.028 mg/mL), naturally-occurring human atelocollagen type I (Collagen, Type I, Acid Soluble, From Human Skin, SIGMA-ALDRICH) (0.1 mg/mL), or fibrous mini-collagen (Example 7) (0.1 mg/mL) to adjust the pH to 2, 3 μL of pepsin (Pepsin, From Porcine Stomach Mucosa, 3370 units/mg protein; SIGMA-ALDRICH) solution (the amount of pepsin is three times that of each protein when converted into moles) was added, and pepsin digestion was carried out at 20° C. (2720 Thermal cycler, Applied Biosystems) for two hours. Here, preparations of each sample with no pepsin added, preparations of pepsin (Pepsin, From Porcine Stomach Mucosa, 3370 units/mg protein; SIGMA-ALDRICH) alone (same amount as the amount used to digest each sample), and preparations containing neither sample nor pepsin were prepared as controls. 10 mM acetic acid solution was added instead of the pepsin solution or sample, and incubation was carried out at 20° C. for two hours. 1 μL of 1 M Tris (2-Amino-2-hydroxymethyl-1,3-propanediol (Tris aminomethane); Wako) solution was added to stop the reaction, and collagen was refibrillized irreversibly by incubation at 4° C. for 18 hours. 17 μL of Laemmli Sample Buffer (BIO-RAD) containing 5% 2-mercaptoethanol (Wako) was added for reduction by heating (DTU-18, TAITEC) at 98° C. for five minutes. An electrophoresis buffer (Tris/Glycine/SDS, BIO-RAD) and Super Sep™ Ace 10% to 20% 17 well (Wako) were placed in an electrophoresis vessel (DPE-1020, DAIICHI PURE CHEMICALS CO., LTD), and 18 μL of the heat-treated sample solutions were applied to Super Sep™ Ace 10% to 20% 17 well (Wako), and electrophoresis was carried out at 40 mA (My Run, COSMO BIO CO., LTD) for 55 minutes. Then, silver staining was carried out using 2D-Silver Stain Reagent II (COSMO BIO CO., LTD). First the gel was fixed by shaking for 20 minutes in 40 mL of fixing solution-I (50% methanol (Wako), 10% acetic acid (Wako), and 40% water (BMS)). Next, the gel was fixed by shaking for 30 minutes in 40 mL of fixing solution-II (30% methanol (Wako), 10% acetic acid (Wako), 5% fixing agent (2D-Silver Stain Reagent II, COSMO BIO CO., LTD.), and 55% ultrapure water (BMS)). Pretreatment was carried out by shaking for 20 minutes in 40 mL of pretreatment solution (50% methanol (Wako), 5% pretreatment agent (2D-Silver Stain Reagent II, COSMO BIO CO., LTD.), and 45% ultrapure water (BMS)). The gel was washed for ten minutes with 40 mL of ultrapure water (BMS), stained for 30 minutes using 40 mL of silver staining solution (5% staining solution A (2D-Silver Stain Reagent II, COSMO BIO CO., LTD.), 5% staining solution B (2D-Silver Stain Reagent II, COSMO BIO CO., LTD.), and 90% ultrapure water (BMS)), then washed for five minutes using 40 mL of ultrapure water (BMS). The wash was repeated three times. The gel was developed for eight minutes using 40 mL of developing solution (5% developing stock solution (2D-Silver Stain Reagent II, COSMO BIO CO., LTD.) and 95% ultrapure water (BMS)), and 2 mL of stop solution (2D-Silver Stain Reagent II, COSMO BIO CO., LTD.)) was added to stop the development. Finally, the gel was washed for ten minutes using 40 mL of ultrapure water (BMS), and an image was scanned (FIG. 24) using a scanner (GT-X900, EPSON). The bands in the lanes to which MC-GPP, pepsin-digested MC-GPP, an equivalent amount of pepsin only to that used to digest MC-GPP, purified fibrous mini-collagen (Example 7), pepsin-digested fibrous mini-collagen (Example 7), and an equivalent amount of pepsin only to that used to digest fibrous mini-collagen (Example 7) were applied were analyzed using ImageJ (see FIG. 25).

As a result, naturally-occurring human atelocollagen type I was not cleaved by pepsin digestion. Purified fibrous mini-collagen showed a band near 50 kDa, but regions other than the collagen domain were cleaved and eliminated by pepsin digestion such that a band for the collagen domain was observed around 30 kDa. Also with MC-GPP, bands other than that of the collagen domain were eliminated such that a band for the collagen domain was observed near 30 kDa. The above revealed that MC-GPP is resistant against pepsin cleavage and is correctly folded into a triple helix structure, and suggested that the presence of the cysteine-rich domain of SP-D leads to formation of a triple helix structure of the collagen portion.

Industrial Applicability

Using mammalian cells as host, the present invention can provide advanced human collagen analogs that have a triple helix structure similar to that of naturally occurring ones, which can be more easily handled than the naturally-occurring ones, expression vectors that enable production thereof, and human collagen analog-producing cells.

The production methods of the present invention can be applied not only to collagen, but also to proteins that have a triple helix structure, such as collectin.

Since the collagen analogs of the present invention have lower molecular weights than those of naturally-occurring collagens, they are easily purified and easily handled. It is considered that these novel collagen analogs having a triple helix structure have properties that are different from those of known collagens, and their applications as novel biomaterials are expected.

The invention claimed is:

1. A recombinant protein having a triple helix structure, which comprises a protein encoded by a polynucleotide comprising (i) to (v) below in order from the amino terminus:
(i) a signal peptide domain gene of human collectin;
(ii) a cysteine-rich domain gene of human collectin;
(iii) a collagen domain gene of human collagen;
(iv) a neck domain gene of human collectin; and
(v) a carbohydrate recognition domain gene of human collectin.

2. The recombinant protein having a triple helix structure of claim 1, wherein the signal peptide domain gene of human collectin is a signal peptide domain gene of human surfactant protein D (SP-D) and a polynucleotide comprising the nucleotide sequence of SEQ ID NO: 4.

3. The recombinant protein having a triple helix structure of claim 1, wherein the cysteine-rich domain gene of human collectin is a cysteine-rich domain gene of human surfactant protein D (SP-D) and a polynucleotide comprising the nucleotide sequence of SEQ ID NO: 5.

4. The recombinant protein having a triple helix structure of claim 1, wherein the neck domain gene of human collectin is a neck domain gene of human mannan-binding lectin (MBL) and a polynucleotide comprising the nucleotide sequence of SEQ ID NO: 6.

5. The recombinant protein having a triple helix structure of claim 1, wherein the carbohydrate recognition domain gene of human collectin is a carbohydrate recognition domain gene of human mannan-binding lectin (MBL) and a polynucleotide comprising the nucleotide sequence of SEQ ID NO: 7.

6. The recombinant protein having a triple helix structure of claim 1, wherein the collagen domain gene of human collagen comprises at least one or more types of collagen domain genes of α-chain human collagens.

7. The recombinant protein having a triple helix structure of claim 1, wherein the collagen domain gene of human collagen is a collagen domain gene of a human type I collagen comprising an α-chain human collagen.

8. The recombinant protein having a triple helix structure of claim 6 or 7, wherein the collagen domain gene of an α-chain human collagen is a polynucleotide comprising the nucleotide sequence of SEQ ID NO: 8.

9. The recombinant protein having a triple helix structure of claim 1, which comprises a protein comprising the amino acid sequence of SEQ ID NO: 1.

10. The recombinant protein having a triple helix structure of claim 1, wherein the polynucleotide is a polynucleotide comprising the nucleotide sequence of SEQ ID NO: 3.

11. A method for producing a protein having a triple helix structure, wherein the method comprises the steps of:
(a) introducing into a vector a polynucleotide comprising (i) to (v) below in order from the amino terminus:
(i) a signal peptide domain gene of human collectin;
(ii) a cysteine-rich domain gene of human collectin;
(iii) a collagen domain gene of human collagen;
(iv) a neck domain gene of human collectin; and
(v) a carbohydrate recognition domain gene of human collectin;
(b) transforming a host cell by gene introduction using the vector; and
(c) culturing or breeding the transformant, and collecting a protein having a triple helix structure from the cell or its culture supernatant.

12. The method of claim 11, wherein the signal peptide domain gene of human collectin is a signal peptide domain gene of human surfactant protein D (SP-D) and a polynucleotide comprising the nucleotide sequence of SEQ ID NO: 4.

13. The method of claim 11, wherein the cysteine-rich domain gene of human collectin is a cysteine-rich domain gene of human surfactant protein D (SP-D) and a polynucleotide comprising the nucleotide sequence of SEQ ID NO: 5.

14. The method of claim 11, wherein the neck domain gene of human collectin is a neck domain gene of human mannan-binding lectin (MBL) and a polynucleotide comprising the nucleotide sequence of SEQ ID NO: 6.

15. The method of claim 11, wherein the carbohydrate recognition domain gene of human collectin is a carbohydrate recognition domain gene of human mannan-binding lectin (MBL) and a polynucleotide comprising the nucleotide sequence of SEQ ID NO: 7.

16. The method of claim 11, wherein the collagen domain gene of human collagen comprises at least one or more types of collagen domain genes of α-chain human collagens.

17. The method of claim 11, wherein the collagen domain gene of human collagen is a collagen domain gene of a human type I collagen comprising an α-chain human collagen.

18. The method of claim 16 or 17, wherein the collagen domain gene of an α-chain human collagen is a polynucleotide comprising the nucleotide sequence of SEQ ID NO: 8.

19. The method of claim 11, wherein the vector used in step (a) is pNC1 of SEQ ID NO: 2.

20. The method of claim 11, wherein the vector used in step (a) is pDC6/CF of SEQ ID NO: 9.

* * * * *

UNITED STATES PATENT AND TRADEMARK OFFICE
CERTIFICATE OF CORRECTION

| | | |
|---|---|---|
| PATENT NO. | : 8,470,555 B2 | Page 1 of 1 |
| APPLICATION NO. | : 13/141138 | |
| DATED | : June 25, 2013 | |
| INVENTOR(S) | : Suzuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 212 days.

Signed and Sealed this
Twenty-seventh Day of January, 2015

Michelle K. Lee
*Deputy Director of the United States Patent and Trademark Office*